(12) United States Patent
Lee et al.

(10) Patent No.: US 8,030,096 B2
(45) Date of Patent: *Oct. 4, 2011

(54) WATER-SOLUBLE RHODAMINE DYES CONJUGATES

(75) Inventors: Linda G. Lee, Palo Alto, CA (US);
Ronald Graham, Carlsbad, CA (US);
Lily Lu, Foster City, CA (US); Elana E. Swartzman, Alameda, CA (US);
William E. Werner, San Carlos, CA (US)

(73) Assignee: Applied Biosystems LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/855,649

(22) Filed: Aug. 12, 2010

(65) Prior Publication Data

US 2011/0081688 A1 Apr. 7, 2011

Related U.S. Application Data

(60) Continuation of application No. 12/402,634, filed on Mar. 12, 2009, now Pat. No. 7,795,042, which is a continuation of application No. 11/059,035, filed on Feb. 14, 2005, now Pat. No. 7,504,496, which is a continuation of application No. 10/007,253, filed on Oct. 24, 2001, now abandoned, which is a division of application No. 09/661,206, filed on Sep. 14, 2000, now Pat. No. 6,372,907, which is a division of application No. 09/433,093, filed on Nov. 3, 1999, now Pat. No. 6,191,278.

(51) Int. Cl.
*G01N 33/53* (2006.01)
*C12Q 1/68* (2006.01)
*C07H 21/02* (2006.01)
*C07H 15/00* (2006.01)
*C07K 2/00* (2006.01)

(52) U.S. Cl. ............... 436/800; 435/6; 435/7.1; 435/7.2; 536/4.1; 536/23.1; 536/24.3; 536/25.3; 536/26.6; 530/300; 530/350

(58) Field of Classification Search .................. 436/800; 530/300, 350; 435/6, 7.1, 7.2; 536/4.1, 23.1, 536/24.3, 25.3, 26.6
See application file for complete search history.

(56) References Cited

U.S. PATENT DOCUMENTS

| | | |
|---|---|---|
| 5,126,218 A | 6/1992 | Clarke |
| 5,366,860 A | 11/1994 | Bergot et al. |

(Continued)

FOREIGN PATENT DOCUMENTS

WO 9736960 10/1997

(Continued)

OTHER PUBLICATIONS

Gee et al., Novel Derivation of Protein Thiols with Fluorinated Fluoresceins, Tetrahedron Letters, 37(44):7905-7908 (1996).

(Continued)

*Primary Examiner* — Jezia Riley

(57) ABSTRACT

The present invention provides novel, water-soluble, red-emitting fluorescent rhodamine dyes and red-emitting fluorescent energy-transfer dye pairs, as well as labeled conjugates comprising the same and methods for their use. The dyes, energy-transfer dye pairs and labeled conjugates are useful in a variety of aqueous-based applications, particularly in assays involving staining of cells, protein binding, and/or analysis of nucleic acids, such as hybridization assays and nucleic acid sequencing.

47 Claims, 4 Drawing Sheets

U.S. PATENT DOCUMENTS

Figure 1:
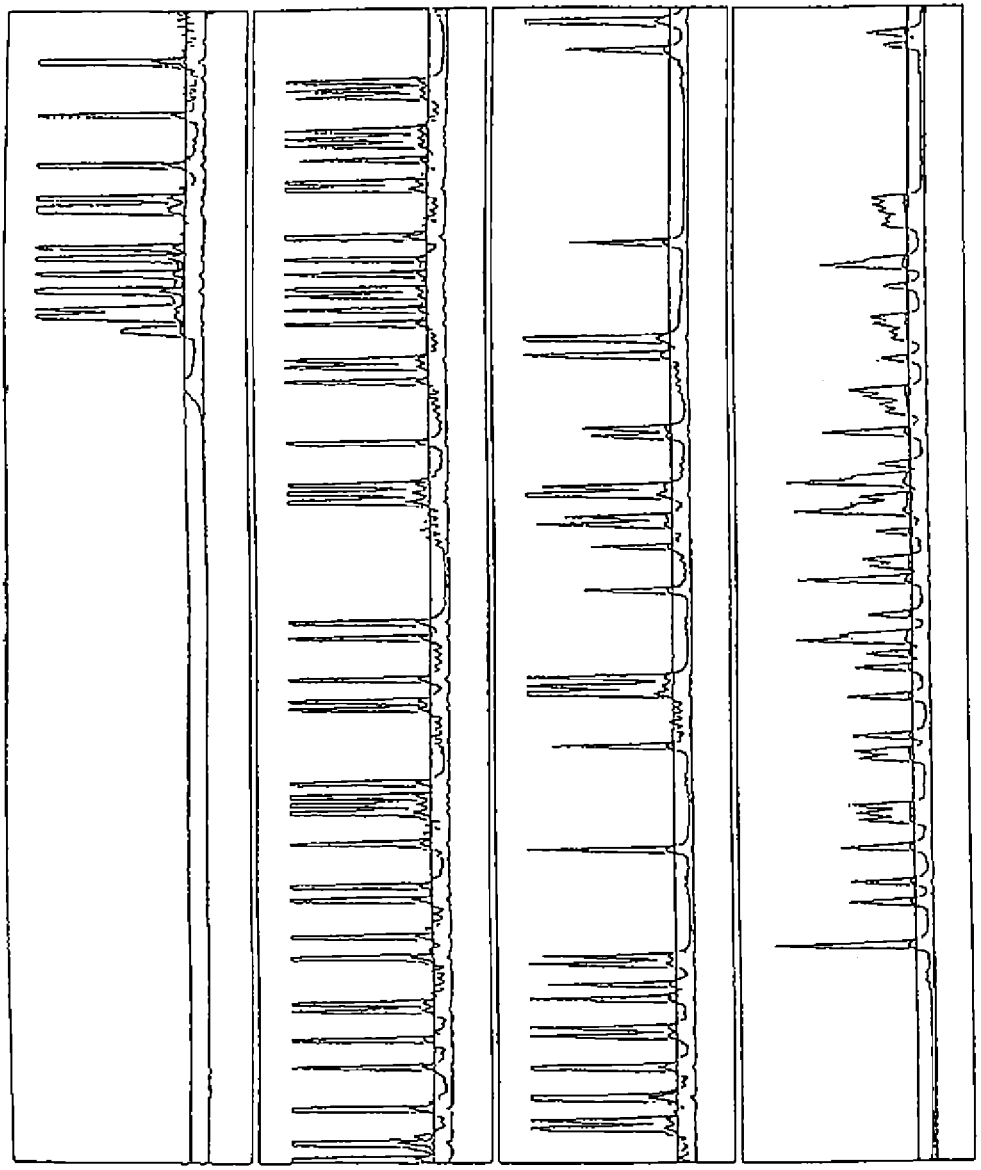

| | | | |
|---|---|---|---|
| 5,654,419 | A | 8/1997 | Mathies et al. |
| 5,654,442 | A | 8/1997 | Menchen |
| 5,750,409 | A | 5/1998 | Herrmann et al. |
| 5,800,996 | A | 9/1998 | Lee et al. |
| 5,840,999 | A | 11/1998 | Benson et al. |
| 5,847,162 | A | 12/1998 | Lee et al. |
| 5,863,727 | A | 1/1999 | Lee et al. |
| 5,936,087 | A | 8/1999 | Benson et al. |
| 6,017,712 | A | 1/2000 | Lee et al. |
| 6,080,852 | A | 6/2000 | Lee et al. |
| 6,191,278 | B1 | 2/2001 | Lee et al. |
| 6,372,907 | B1 | 4/2002 | Lee et al. |
| 6,649,769 | B2 | 11/2003 | Lee et al. |
| 7,504,496 | B2 | 3/2009 | Lee et al. |
| 7,795,042 | B2 * | 9/2010 | Lee et al. .................... 435/7.92 |

FOREIGN PATENT DOCUMENTS

| | | |
|---|---|---|
| WO | 9739064 | 10/1997 |
| WO | 9915517 | 4/1999 |
| WO | 9927020 | 6/1999 |

OTHER PUBLICATIONS

Koch et al., Nucleophillic Reactions of Pyridines and Imidazoles with Vinyl and Aromatic Halides, Journal of Organic Chemistry, 58:1409-1414 (1993).

Lee et al., DNA Sequencing with Dye-Labeled Terminators and T7 DNA Polymerase: Effect of Dyes and dNTPs on Incorporation of Dye-Terminators and Probability Analysis of Termination Fragments, Nucleic Acids Res., 20 (10):2471-2483 (1992).

Weiss, et al., First Ever Per(onio) Substitution of Benzene: The Role of Counterion, Agnew. Chem, Int, Ed. Engl., 34 (12):1319-1321 (1995).

* cited by examiner

SEQUENCE LISTING

<160> NUMBER OF SEQ ID NOS: 1

<210> SEQ ID NO 1
<211> LENGTH: 459
<212> TYPE: DNA
<213> ORGANISM: Homosapien
<220> FEATURE:
<221> NAME/KEY: misc_feature
<222> LOCATION: 4, 32, 36, 41, 62, 90, 93, 143, 164, 249, 371, 393, 397
<223> OTHER INFORMATION: n is any nucleotide of a, t, c or g

<400> SEQUENCE: 1

```
ggtncccggg gatcctctag agtcgacctg cnggcntgca ngcttgagta ttctatagtg      60
tncctaaata gcttggcgta atcatggtcn tangctgttt cctgtgtcaa attgttatcc     120
gctcacaatt cccacacata cangccggaa gcataaagtg taangcctgg ggtgcctaat     180
gagtgagcta actcacatta attgcgttgc gctcactgcc cgctttccag tcggaaacct     240
gtcgtgccng ctgcataatg aatcggccac gcgcgggaga ggcggtttgc gtattgggcg     300
ctcttccgct tcctcgctac tgactcgctg cgctcggtcg ttcggctgcg gcgagcggaa     360
tcagctcact naaggcggaa tacggtatcc acnaatnggg atacgcagaa agaacatgta     420
gcaaaggcca gcaaaggcca gaaccgaaaa aggccgcgt                            459
```

WATER-SOLUBLE RHODAMINE DYES CONJUGATES

This application is a continuation of application Ser. No. 12/402,634, filed on Mar. 12, 2009, which is a continuation of application Ser. No. 11/059,035, filed on Feb. 14, 2005, now U.S. Pat. No. 7,504,496 issued on Mar. 17, 2009, which is a continuation of application Ser. No. 10/007,253, filed on Oct. 24, 2001, which is a division of application Ser. No. 09/661,206, filed on Sep. 14, 2000, now U.S. Pat. No. 6,372,907, issued Apr. 16, 2002, which is a division of application Ser. No. 09/433,093, filed on Nov. 3, 1999, now U.S. Pat. No. 6,191,278, issued Feb. 20, 2001, all of which are incorporated herein by reference in their entireties.

1. FIELD OF THE INVENTION

The present invention relates generally to fluorescent dye compounds that are useful as molecular probes. In particular, the present invention relates to fluorescent rhodamine dye compounds that are photostable and highly water-soluble.

2. BACKGROUND OF THE INVENTION

The non-radioactive detection of nucleic acids utilizing fluorescent labels is an important technology in modern molecular biology. By eliminating the need for radioactive labels, safety is enhanced and the environmental impact and costs associated with reagent disposal is greatly reduced. Examples of methods utilizing such non-radioactive fluorescent detection include automated DNA sequencing, oligonucleotide hybridization methods, detection of polymerase-chain-reaction products, immunoassays, and the like.

In many applications it is advantageous to employ multiple spectrally distinguishable fluorescent labels in order to achieve independent detection of a plurality of spatially overlapping analytes, i.e., multiplex fluorescent detection. Examples of methods utilizing multiplex fluorescent detection include single-tube multiplex DNA probe assays, PCR, single nucleotide polymorphisms and multi-color automated DNA sequencing. The number of reaction vessels may be reduced thereby simplifying experimental protocols and facilitating the production of application-specific reagent kits. In the case of multi-color automated DNA sequencing, multiplex fluorescent detection allows for the analysis of multiple nucleotide bases in a single electrophoresis lane thereby increasing throughput over single-color methods and reducing uncertainties associated with inter-lane electrophoretic mobility variations.

Assembling a set of multiple spectrally distinguishable fluorescent labels useful for multiplex fluorescent detection is problematic. Multiplex fluorescent detection imposes at least six severe constraints on the selection of component fluorescent labels, particularly for applications requiring a single excitation light source, an electrophoretic separation, and/or treatment with enzymes, e.g., automated DNA sequencing. First, it is difficult to find a set of structurally similar dyes whose emission spectra are spectrally resolved, since the typical emission band half-width for organic fluorescent dyes is about 40-80 nanometers (nm). Second, even if dyes with non-overlapping emission spectra are identified, the set may still not be suitable if the respective fluorescent quantum efficiencies are too low. Third, when several fluorescent dyes are used concurrently, simultaneous excitation becomes difficult because the absorption bands of the dyes are usually widely separated. Fourth, the charge, molecular size, and conformation of the dyes must not adversely affect the electrophoretic mobilities of the analyte. Fifth, the fluorescent dyes must be compatible with the chemistry used to create or manipulate the analyte, e.g., DNA synthesis solvents and reagents, buffers, polymerase enzymes, ligase enzymes, and the like. Sixth, the dye must have sufficient photostability to withstand laser excitation.

Currently available multiple dye sets suitable for use in four-color automated DNA sequencing applications require blue or blue-green laser light to adequately excite fluorescence emissions from all of the dyes making up the set, e.g., argon-ion lasers. As lower cost red lasers become available, a need develops for fluorescent dye compounds and their nucleic acid conjugates which satisfy the above constraints and are excitable by laser light having a wavelength above about 500 nm.

3. SUMMARY OF THE INVENTION

These and other objects are furnished by the present invention, which in one aspect provides water-soluble, photostable rhodamine dye compounds that can be used as labels in a variety of biological and non-biological assays. Generally, the rhodamine dye compounds of the invention comprise a rhodamine-type parent xanthene ring substituted at the xanthene C-9 carbon with a substituted phenyl ring. The substituted phenyl ring contains three to five substituents including: an ortho carboxyl or sulfonate group; one or more aminopyridinium ("Pyr$^+$") groups; and one alkylthio, arylthio or heteroarylthio group. The alkylthio, arylthio or heteroarylthio group is believed to be positioned para to the carboxyl or sulfonate group, with the remaining positions being substituted with Pyr$^+$ groups.

The aminopyridinium groups are attached to the phenyl ring at the pyridinium ring nitrogen and may be substituted or unsubstituted at the pyridinium ring carbons with one or more of a wide variety of the same or different substituents. The substituents may be virtually any group. However, electron-withdrawing groups (e.g., —NO$_2$, —F, —Cl, —CN, —CF$_3$, etc.) should not be attached directly to the pyridinium ring carbons, as these substituents may adversely affect the synthesis of the rhodamine dyes. Electron-withdrawing groups may be included on a substituent as long as it is spaced away from the pyridinium ring so as to not adversely affect the synthesis of the dyes. Thus, typical pyridinium ring carbon substituents include, but are not limited to —R, —OR, —SR, —NRR, —S(O)$_2$O$^-$, —S(O)$_2$OH, —S(O)$_2$R, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each R is independently hydrogen, (C$_1$-C$_6$) alkyl, or heteroalkyl, (C$_5$-C$_{14}$) aryl or heteroaryl. The R groups may be further substituted with one or more of the same or different substituents, which are typically selected from the group consisting of —X, —R', =O, —OR', —SR', =S, —NR'R', =NR', —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R', —C(O)R', —C(O)X, —C(S)R', —C(S)X, —C(O)OR', —C(O)O$^-$, —C(S)OR', —C(O)SR', —C(S)SR', —C(O)NR'R', —C(S)NR'R' and —C(NR)NR'R', where each X is independently a halogen (preferably —F or —Cl) and each R' is independently hydrogen, (C$_1$-C$_6$) alkyl or heteroalkyl, (C$_5$-C$_{14}$) aryl or heteroaryl. Preferably, the pyridinium ring carbons are unsubstituted. When substituted, the most preferred substituents are the same or different (C$_1$-C$_6$) alkyls.

The amino group of the aminopyridinium groups is located at the 4-position of the pyridinium ring. The amino group may be a primary, secondary or tertiary amino group, but is typically a tertiary amino. The nitrogen substituents are typically $(C_1-C_6)$ alkyl groups or heteroalkyl groups, and may be the same or different. Alternatively, the nitrogen is substituted with an alkyldiyl or heteroalkyldiyl bridge having from 2 to 5 backbone atoms such that the substituents and the nitrogen atom taken together form a ring structure, which may be saturated or unsaturated, but is preferably saturated. The bridge substituent may be branched or straight-chain, but is preferably straight-chain, e.g., ethano, propano, butano, etc. The ring structure may contain, in addition to the nitrogen atom of the aminopyridinium, one or more heteroatoms, which are typically selected from the group consisting of O, S and N. When the nitrogen atom is not included in a ring structure, the amino group is preferably dimethylamino. When the nitrogen atom is included in a ring structure, the ring is preferably a morpholino or piperazine ring. Particularly preferred $Pyr^+$ groups are 4-(dimethylamino)pyridinium, 4-(morpholino) pyridinium, and 1-methyl-4-piperazinylpyridinium.

The alkylthio, arylthio or heteroarylthio group is attached to the phenyl ring via the sulfur atom and may also be substituted with one or more of the same or different substituents. The nature of the substituents will depend upon whether the group is an alkylthio, arylthio or heteroarylthio. The alkyl chain of an alkylthio group may be substituted with virtually any substituent, including, but not limited to, —X, —R, =O, —OR, —SR, =S, —NRR, =NR, —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F or —Cl) and each R is independently hydrogen, $(C_1-C_6)$ alkyl or heteroalkyl, $(C_5-C_{14})$ aryl or heteroaryl. The R groups may be further substituted with one or more of the same or different substituents, which are typically selected from the group consisting of —X, —R', =O, —OR', —SR', =S, —NR'R', =NR', —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R', —C(O)R', —C(O)X, —C(S)R', —C(S)X, —C(O)OR', —C(O)O$^-$, —C(S)OR', —C(O)SR', —C(S)SR', —C(O)NR'R', —C(S)NR'R' and —C(NR)NR'R', where each X is independently a halogen (preferably —F or —Cl) and each R' is independently hydrogen, $(C_1-C_6)$ alkyl or heteroalkyl, $(C_5-C_{14})$ aryl or heteroaryl.

Due to synthetic constraints, when the group is an arylthio or heteroarylthio, the aryl or heteroaryl rings should not be directly substituted with halogens, although halogens may be included in the substituent (e.g., a haloalkyl). Thus, when the group is an arylthio or a heteroarylthio, typical substituents include any of the above-listed alkylthio substituents, with the exception of halogen.

The rhodamine dyes of the invention may include a linker L that can be used to conjugate the dyes, preferably by way of covalent attachment, to other compounds or substances, such as peptides, proteins, antibodies, nucleoside/tides, polynucleotides, polymers, particles, etc. The identity of linker L will depend upon the nature of the desired conjugation. For example, the conjugation may be: (i) mediated by ionic interactions, in which case linker L is a charged group; (ii) mediated by hydrophobic interactions, in which case L is a hydrophobic moiety, (iii) mediated by covalent attachment, in which case L is a reactive functional group ($R_x$) that is either capable of forming a covalent linkage with another complementary functional group ($F_x$) or is capable of being activated so as to form a covalent linkage with complementary functional group $F_x$; or (iv) mediated through the use of pairs of specific binding molecules, such as biotin and avidin/streptavidin, in which case linker L is one member of the pair, e.g., biotin.

Linker L is attached to the rhodamine dyes of the invention at the rhodamine-type parent xanthene ring and/or it is included as a substituent on the alkylthio, arylthio or heteroarylthio group substituting the fully substituted phenyl ring. When linker L is attached to the rhodamine-type parent xanthene ring, it is typically attached to a xanthene nitrogen or at the xanthene C4 carbon. The rhodamine dyes may have multiple linking moieties, but preferably have only a single linking moiety.

Depending upon the particular application, linker L may be attached directly to the rhodamine dye, or indirectly through one or more intervening atoms that serve as a spacer. Linker L can be hydrophobic or hydrophilic, long or short, rigid, semirigid or flexible, depending upon the particular application. When L is positioned at the alkylthio, arylthio or heteroarylthio group, it is preferably attached directly to the molecule. In this latter embodiment, L is a bond.

The new, fully substituted phenyl rings described herein can be used to replace the "bottom ring" or "bottom substituent," i.e., the substituent attached to the xanthene C9 carbon, of virtually any rhodamine dye that is known in the art or that will be later developed. Thus, the new, fully substituted phenyl rings described herein can be covalently attached to the C-9 position of virtually any rhodamine-type parent xanthene ring that is now known or that will be later developed to yield a rhodamine dye without longer absorption and emission maxima and with greater water-solubility. As the new bottom rings do not deleteriously affect the photostability properties that are characteristic of rhodamine dyes, the new dyes are also highly photostable. Exemplary rhodamine-type parent xanthene rings that can comprise the rhodamine dyes of the invention include, by way of example and not limitation, the xanthene rings ("top rings") of the rhodamine dyes described in U.S. Pat. No. 5,936,087; U.S. Pat. No. 5,750,409; U.S. Pat. No. 5,366,860; U.S. Pat. No. 5,231,191; U.S. Pat. No. 5,840,999; U.S. Pat. No. 5,847,162; U.S. application Ser. No. 09/038,191, filed Mar. 10, 1998; U.S. application Ser. No. 09/277,793, filed Mar. 27, 1999; U.S. application Ser. No. 09/325,243, filed Jun. 3, 1999; PCT Publication WO 97/36960; PCT Publication WO 99/27020; Sauer et al., 1995, J. Fluorescence 5(3):247-261; Arden-Jacob, 1993, *Neue Lanwellige Xanthen-Farbstoffe für Fluoreszenzsonden und Farbstoff Laser*, Verlag Shaker, Germany, and Lee et al., 1992, Nucl. Acids Res. 20(10):2471-2483. Preferred rhodamine-type parent xanthene rings are fluorescent.

In another aspect, the invention provides labeled conjugates comprising a rhodamine dye according to the invention and another molecule or substance. The rhodamine dye is conjugated to the other molecule or substance, typically via covalent attachment, through linker L, as previously described. Once conjugated, the rhodamine dye provides a convenient fluorescent label for subsequent detection. The rhodamine dyes of the invention can be used to fluorescently label a wide variety of molecules and substances, including but not limited to, amino acids, peptides, proteins, antibodies, enzymes, receptors, nucleosides/tides, nucleoside/tide analogs, polynucleotides, polynucleotide analogs, nucleic acids, carbohydrates, lipids, steroids, hormones, vitamins, drugs, metabolites, toxins, organic polymers, etc. The dyes can also be used to label particles such as solid phase synthesis substrates, nanoparticles, microspheres or liposomes. In embodiments involving nanoparticles, microspheres and/or liposomes, the due need not include a linking moiety. It can be incorporated into the various particles during their formation.

The molecule or substance may be labeled with one or more rhodamine dyes of the invention, which may be the same or different.

In one embodiment, a rhodamine dye of the invention is covalently conjugated to another dye compound to form an energy-transfer dye pair. The energy-transfer dye pair can be further conjugated to other molecules or substances, as described above, to provide an energy-transfer label. The energy-transfer dye pair generally comprises a donor dye (DD), an acceptor dye (AD), and a linkage linking the donor and acceptor dyes. The donor dye is capable of absorbing light at a first wavelength and emitting excitation energy in response. The acceptor dye is capable of absorbing the excitation energy emitted by the donor dye and fluorescing at a second wavelength in response thereto. While in many instances the emission wavelength of the donor dye and the excitation wavelength of the acceptor dye will overlap, such overlap is not required. The acceptor dye need only fluoresce in response to the donor dye absorbing light, regardless of the mechanism of action. The linkage serves to facilitate efficient energy transfer between the donor and acceptor dyes. According to this aspect of the invention, at least one of the donor and acceptor dyes is a rhodamine dye according to the invention. Preferably, the acceptor dye is a rhodamine dye according to the invention and the donor dye is a xanthene dye, most typically a fluorescein dye. The exact nature or identity of the donor dye will depend upon the excitation and emission properties of the rhodamine acceptor dye, and will be apparent to those having skill in the art. When covalently conjugated to enzymatically-incorporatable nucleotides, such as dideoxynucleotide 5'-triphosphates, i.e. "terminators", such energy-transfer dyes are ideally suited for use in sequencing nucleic acids.

Since the rhodamine dyes of the invention may comprise virtually any rhodamine-type parent xanthene ring, the dyes cover a broad range of the visible spectrum, ranging from green to red. Thus, both dyes of an energy-transfer dye pair may be rhodamine dyes of the invention. In this embodiment, one dye of the invention acts as the donor and another as the acceptor, depending upon their spectral properties.

In another embodiment, a rhodamine dye of the invention, or an energy-transfer dye pair including a rhodamine dye of the invention, is covalently conjugated to a nucleoside/tide, nucleoside/tide analog, polynucleotide or polynucleotide analog to form a labeled conjugate therewith. The dye or dye pair is typically conjugated to the nucleobase moiety of the respective nucleoside/tide, polynucleotide or analog, but may be conjugated to other portions of the molecule, such as the 5'-terminus, 3'-terminus and/or the phosphate ester internucleoside linkage.

In one preferred embodiment, the labeled conjugate is a labeled polynucleotide or polynucleotide analog that can be used as a primer for generating labeled primer extensions products via template-directed enzymatic synthesis reactions. In another preferred embodiment, the labeled conjugate is a labeled terminator. When used in conjunction with enzymatically-extendable nucleotides or nucleotide or analogs, appropriate polymerizing enzymes and a primed template nucleic acid, such labeled terminators can be used to generate a series of labeled primer extension products via template-directed enzymatic synthesis for applications such as nucleic acid sequencing.

In a final aspect, the invention provides methods of using the rhodamine dyes or energy-transfer dye pairs of the invention to sequence a target nucleic acid. The method generally comprises forming a series of differently-sized primer extension products labeled with a rhodamine dye or energy-transfer dye pair of the invention, separating the series of differently-sized labeled extension products, typically based on size, and detecting the separated labeled extension products based on the fluorescence of the label. The sequence of the target nucleic acid is then assembled according to known techniques.

The series of differently-sized labeled extension products can be conveniently generated by enzymatically extending a primer-target hybrid according to well-known methods. For example, the series of labeled extension products can be obtained using a primer labeled with a rhodamine dye or dye pair of the invention and enzymatically extending the labeled primer-target hybrid in the presence of a polymerase, a mixture of enzymatically-extendable nucleotides or nucleotide analogs capable of supporting continuous primer extension (e.g., dATP, dGTP, dCTP and dUTP or dTTP) and at least one, typically unlabeled, terminator that terminates primer extension upon incorporation (e.g., a ddNTP). Alternatively, the series of labeled extension products can be obtained using an unlabeled primer and enzymatically extending the unlabeled primer-target hybrid in the presence of a polymerase, a mixture of enzymatically-extendable nucleotides or nucleotide analogs capable of supporting continuous primer extension and at least one terminator labeled with a rhodamine dye or energy-transfer dye pair of the invention. In either embodiment, the polymerase serves to extend the primer with enzymatically-extendable nucleotides or nucleotide analogs until a terminator is incorporated, which terminates the extension reaction. Once terminated, the series of labeled extension products are separated, typically based on size, and the separated labeled extension products detected based on the fluorescence of the labels.

In a particularly advantageous embodiment of this method, a mixture of four different terminators are used in a single extension reaction. Each different terminator is capable of terminating primer extension at a different template nucleotide, e.g., a mixture of 7-deaza-ddATP, ddCTP, 7-deaza-ddGTP and ddTTP or ddUTP, and is labeled with a different, spectrally-resolvable fluorophore, at least one of which is a rhodamine dye or energy-transfer dye pair according to the invention. According to this embodiment, an unlabeled primer-target nucleic acid hybrid is enzymatically extended in the presence of a polymerase, a mixture of enzymatically-extendable nucleotides or nucleotide analogs capable of supporting continuous primer extension and a mixture of the four different labeled terminators. Following separation based on size, a series of separated labeled extension products is obtained in which the emission properties (i.e., color) of each separated extension product reveals the identity of its 3'-terminal nucleotide. In a particularly preferred embodiment, all of the labeled terminators are excitable using a single light source.

Alternatively, terminators may be used in the absence of enzymatically-extendable nucleotides. In this instance, the primer is extended by only a single base. Again, the primer may be labeled, or, alternatively, one or more of the terminators may be labeled. Preferably, a mixture of four different labeled terminators is used, as described above. These "mini sequencing" embodiments are particularly useful for identifying polymorphisms in chromosomal DNA or cDNA.

4. BRIEF DESCRIPTION OF THE DRAWINGS

FIG. 1 provides single color sequencing data obtained with plasmid pGEM, an unlabeled sequencing primer and the labeled terminator 6-FAM-196-7-deaza-ddATP on an ABI PRISM Model 310 sequencer (PE Biosystems, Foster City, Calif.).

Figure 2:
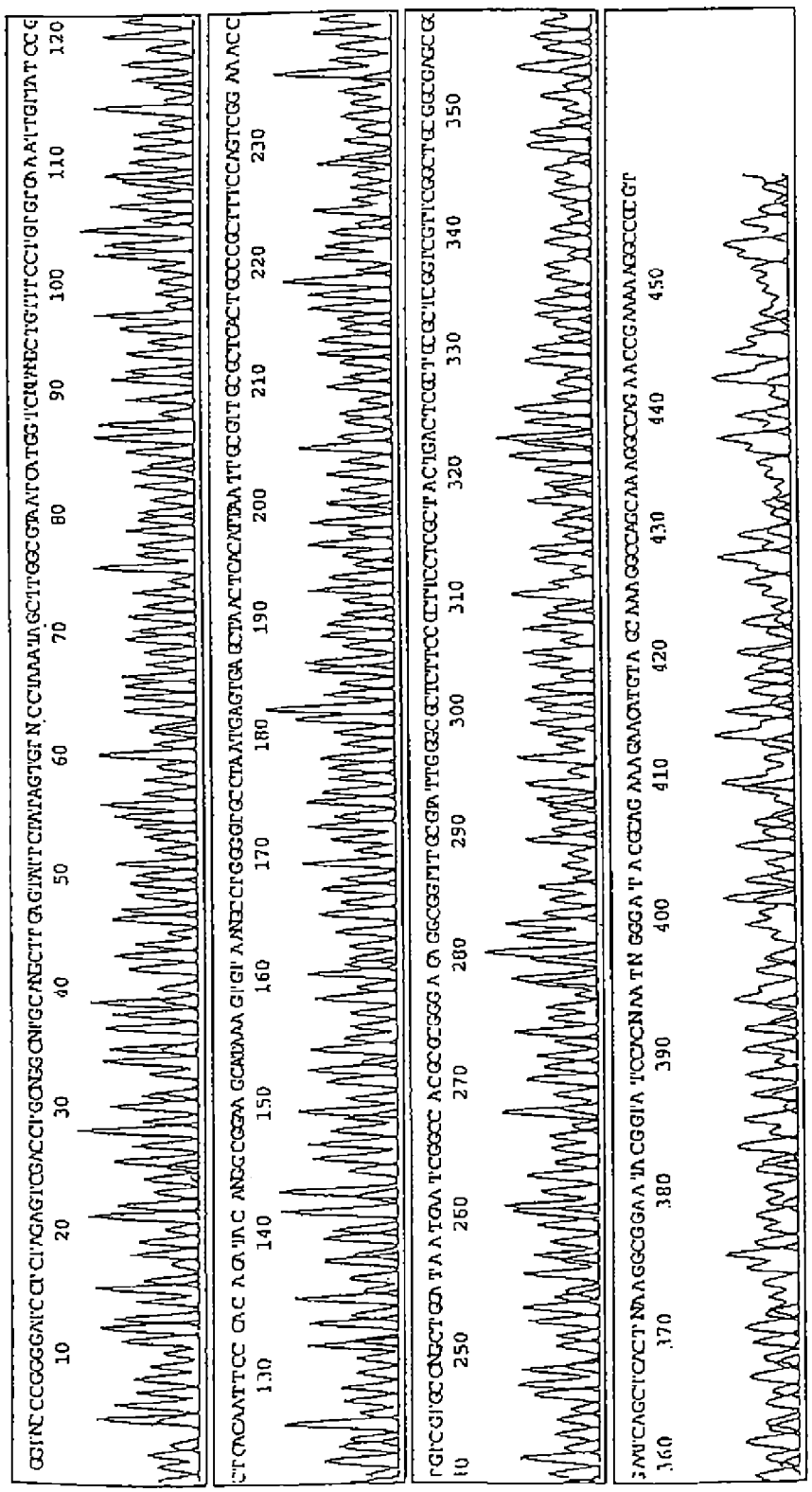

FIG. 2 provides four-color sequencing data obtained with plasmid pGEM1, an unlabeled sequencing primer and a mixture of four, spectrally resolvable, 3'-fluoro, labeled terminators: 6-FAM-196-7-deaza-ddATP; 5-FAM-dR110-7-deaza-ddGTP; 6-FAM-dION-ddTTP; and 6-FAM-dROX-ddCTP on an ABI PRISM Model 310 sequencer (PE Biosystems, Foster City, Calif.).

Figure 3:
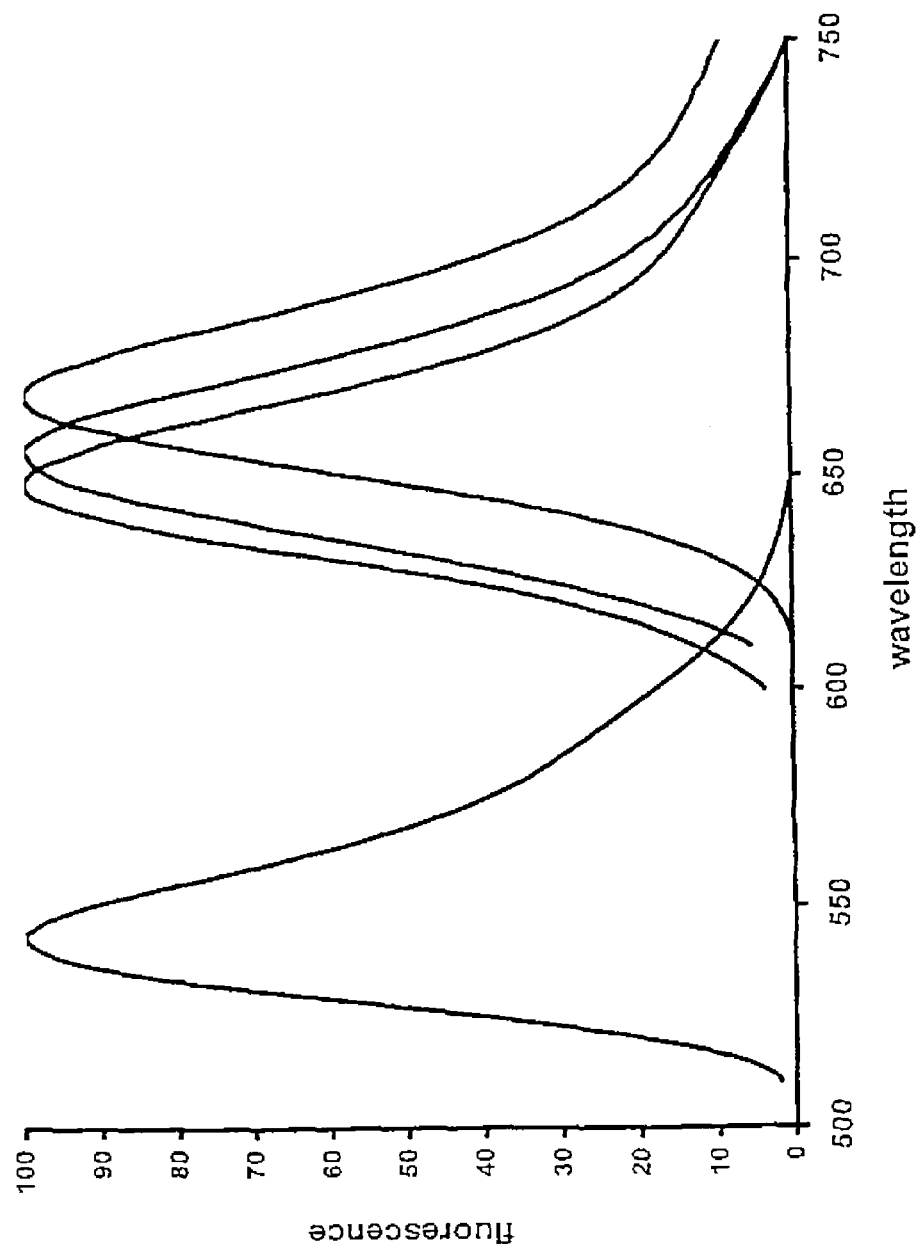

FIG. 3 provides the fluorescence emission spectra ($H_2O$) of four dyes with emission maxima from left to right: 236 (Emax=545 nm), 190 (Emax=650 nm), 196 (Emax=661 nm), 232 (Emax=665 nm). The ordinate axis is fluorescence units and the abscissa axis is emission wavelength in nm.

Figure 4:
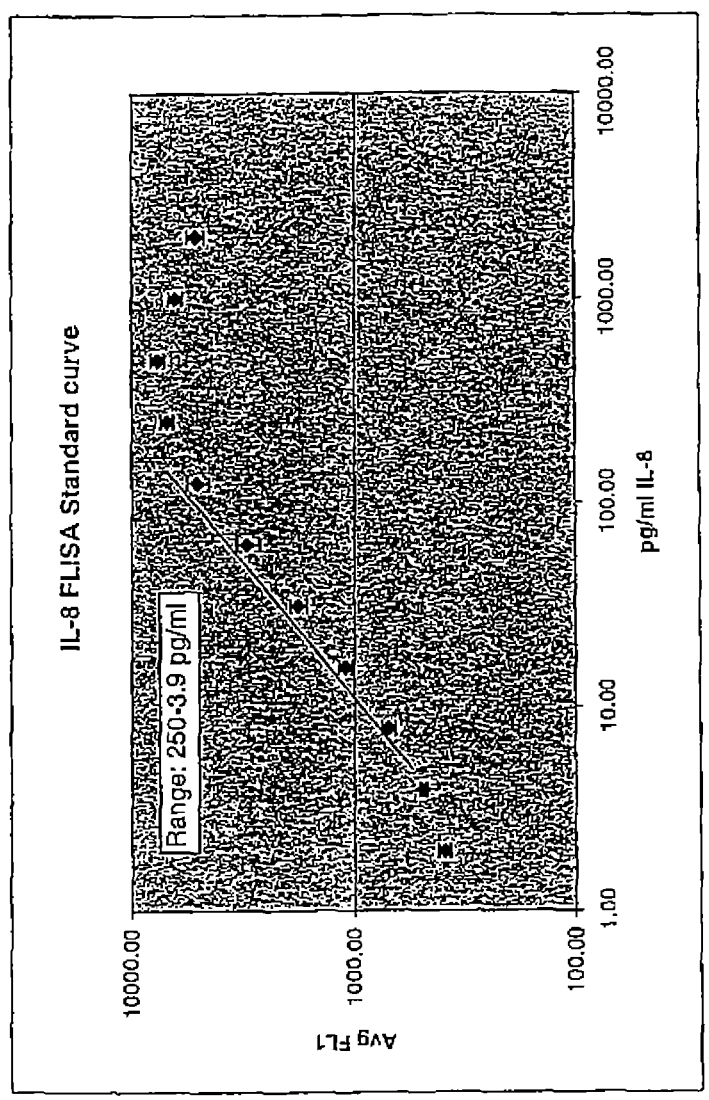

FIG. 4 is a plot of a standard curve of the log v. log graph of the average fluorescence intensity in detection at FL1 (650-685 nm) vs. pg/ml of the IL-8 peptide by a fluorescence-linked immunosorbent assay.

5. DETAILED DESCRIPTION OF THE INVENTION

5.1 Abbreviations

The abbreviations used throughout the specification to refer to certain nucleobases, nucleosides and/or nucleotides are those commonly employed in the art and are as indicated below:

| Expression | Abbreviation |
|---|---|
| adenine | A |
| 7-deazaadenine | 7-deaza-A |
| $N^6$-$\Delta^2$-isopentenyladenine | 6iA |
| $N^6$-$\Delta^2$-isopentenyl-2-methylthioadenine | 2ms6iA |
| cytosine | C |
| guanine | G |
| 6-thioguanine | 6sG |
| 7-deazaguanine | 7-deaza-G |
| $N^2$-dimethylguanine | 2dmG |
| 7-methylguanine | 7mG |
| thymine | T |
| 4-thiothymine | 4sT |
| uracil | U |
| dihydrouracil | D |
| 4-thiouracil | 4sU |
| base Y | Y |
| ribonucleoside-5'-triphosphate | NTP |
| adenosine-5'-triphosphate | ATP |
| 7-deazaadenosine-5'-triphosphate | 7-deaza-ATP |
| cytidine-5'-triphosphate | CTP |
| guanosine-5'-triphosphate | GTP |
| 7-deazaguanosine-5'-triphosphate | 7-deaza-GTP |
| thymidine-5'-triphosphate | TTP |
| uridine-5'-triphosphate | UTP |
| 2'-deoxyribonucleoside-5'-triphosphate | dNTP |
| 2'-deoxyadenosine-5'-triphosphate | dATP |
| 2'-deoxy-7-deazaadenosine-5'-triphosphate | 7-deaza-dATP |
| 2'-deoxycytidine-5'-triphosphate | dCTP |
| 2'-deoxyguanosine-5'-triphosphate | dGTP |
| 2'-deoxy-7-deazaguanosine-5'-triphosphate | 7-deaza-dGTP |
| 2'-deoxythymidine-5'-triphosphate | dTTP |
| 2'-deoxyuridine-5'-triphosphate | dUTP |
| 2',3'-dideoxyribonucleoside-5'-triphosphate | ddNTP |
| 2',3'-dideoxyadenosine-5'-triphosphate | ddATP |
| 2',3'-dideoxy-7-deazaadenosine-5'-triphosphate | 7-deaza-ddATP |
| 2',3'-dideoxycytidine-5'-triphosphate | ddCTP |
| 2',3'-dideoxyguanosine-5'-triphosphate | ddGTP |
| 2',3'-dideoxy-7-deazaguanosine-5'-triphosphate | 7-deaza-ddGTP |
| 2',3'-dideoxythymidine-5'-triphosphate | ddTTP |
| 2',3'-dideoxyuridine-5'-triphosphate | ddUTP |

5.2 Definitions

In general, the terms used herein to describe the present invention rely on definitions as understood and used by those skilled in the art. In particular, chemical structures and substructures are described according to IUPAC recommendations ("Nomenclature of Organic Compounds: A Guide to IUPAC Recommendations 1993, R. Panico, W. H. Powell, and Jean-Claude Richer, Eds., Blackwell Science, Ltd., Oxford, U.K.). As used herein, the following terms are intended to have the following meanings:

"Spectrally Resolvable:" means, in reference to a set of fluorescent dyes and/or energy-transfer dye pairs (collectively referred to herein as "dyes" or "labels"), that the fluorescence emission bands of the respective dyes are sufficiently distinct, i.e., sufficiently non-overlapping, that the dyes, either alone or when conjugated to other molecules or substances, are distinguishable from one another on the basis of their fluorescence signals using standard photodetection systems such as photodetectors employing a series of band pass filters and photomultiplier tubes, charged-coupled devices (CCD), spectrographs, etc., as exemplified by the systems described in U.S. Pat. Nos. 4,230,558 and 4,811,218 or in Wheeless at al., 1985, *Flow Cytometry: Instrumentation and Data Analysis*, pp. 21-76, Academic Press, New York. Preferably, all of the dyes comprising a spectrally resolvable set of dyes are excitable by a single light source.

"Nucleobase:" refers to a substituted or unsubstituted nitrogen-containing parent heteroaromatic ring of a type that is commonly found in nucleic acids. Typically, but not necessarily, the nucleobase is capable of forming Watson-Crick and/or Hoogsteen hydrogen bonds with an appropriately complementary nucleobase. Exemplary nucleobases include, but are not limited to, purines such as 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. Additional exemplary nucleobases can be found in Fasman, 1989, *Practical Handbook of Biochemistry and Molecular Biology*, pp. 385-394, CRC Press, Boca Raton, Fla., and the references cited therein. Preferred nucleobases are purines, 7-deazapurines and pyrimidines. Particularly preferred nucleobases are the normal nucleobases, defined infra, and their common analogs, e.g., 2ms6iA, 6iA, 7-deaza-A, D, 2dmG, 7-deaza-G, 7mG, hypoxanthine, 4sT, 4sU and Y.

"Normal Nucleobase:" refers to a nucleobase that is naturally-occurring and encoding, i.e., adenine, cytosine, guanine, thymine or uracil.

"Nucleoside:" refers to a compound consisting of a nucleobase covalently linked, typically via a heteroaromatic ring nitrogen, to the C1' carbon of a pentose sugar. Typical pentose sugars include, but are not limited to, those pentoses in which one or more of the carbon atoms are each independently substituted with one or more of the same or different —R, —OR, —NRR or halogen groups, where each R is independently hydrogen, $(C_1-C_6)$ alkyl or $(C_5-C_{14})$ aryl. The pentose sugar may be saturated or unsaturated. Exemplary pentose sugars include, but are not limited to, ribose, 2'-deoxyribose, 2'-$(C_1-C_6)$alkylribose, 2'-$(C_1-C_6)$alkoxyribose, 2'-$(C_5-C_{14})$ aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-$(C_1-C_6)$alkylribose, 2'-deoxy-3'-$(C_1-C_6)$alkoxyribose and 2'-deoxy-3'-$(C_5-C_{14})$aryloxyribose.

When the nucleobase is a purine or a 7-deazapurine, the pentose sugar is attached to the N9-position of the nucleobase. When the nucleobase is a pyrimidine, the pentose sugar is attached to the N1-position of the nucleobase (see, e.g., Kornberg and Baker, 1992, *DNA Replication*, 2$^{nd}$ Ed., Freeman, San Francisco), except for pseudouridine, in which the pentose sugar is attached to the C5 position of the uracil nucleobase. Preferred nucleosides are those in which the nucleobase is a purine, a 7-deazapurine, a pyrimidine, a normal nucleobase or a common analog thereof and the pentose sugar is one of the exemplary pentose sugars listed above.

"Normal Nucleoside:" refers to a compound consisting of a normal nucleobase covalently linked via the N1 (C, T or U) or N9 (A or G) position of the nucleobase to the C1' carbon of ribose or 2'-deoxyribose.

"Nucleoside Analog:" refers to a nucleoside in which the pentose sugar is replaced with a pentose sugar analog. Exemplary pentose sugar analogs include, but are not limited to, substituted or unsubstituted furanoses having more or fewer than 5 ring atoms, e.g., erythroses and hexoses, and substituted or substituted 3-6 carbon acyclic sugars. One or more of the carbon atoms may be independently substituted with one or more of the same or different —R, —OR, —NRR or halogen groups, where each R is independently hydrogen, $(C_1-C_6)$ alkyl or $(C_5-C_{14})$ aryl.

"Nucleotide:" refers to a nucleoside in which one or more, typically one, of the pentose carbons is substituted with a phosphate ester having the formula:

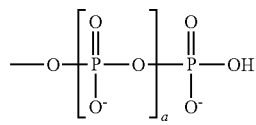

where a is an integer from 0 to 4. Preferably, a is 2 and the phosphate ester is attached to the 3'- or 5'-carbon of the pentose. Particularly preferred nucleotides are those which are enzymatically-extendable or enzymatically incorporatable (defined infra).

"Normal Nucleotide:" refers to a normal nucleoside in which the 3'- or 5'-carbon of the ribose or 2'-deoxyribose sugar is substituted with a phosphate ester having the formula:

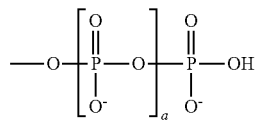

where a is an integer from 0 to 2. Preferred normal nucleotides are those in which a is 2 and the phosphate ester is attached to the 5'-carbon of the ribose (an NTP) or 2'-deoxyribose (a dNTP).

"Nucleotide Analog:" refers to a nucleotide in which the pentose sugar and/or one or more of the phosphate esters is replaced with its respective analog. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present.

Also included within the definition of "nucleotide analog" are nucleobase-containing molecules which can be polymerized into polynucleotide analogs in which the DNA/RNA phosphate ester and/or sugar phosphate ester backbone is replaced with a different type of linkage. Such polynucleotide analogs are described in more detail, infra.

"Enzymatically-Incorporatable Nucleotide or Nucleotide Analog:" refers to a nucleotide or nucleotide analog which is capable of acting as a substrate for a polymerizing enzyme in a template-directed nucleic acid synthesis reaction such that it is incorporated by the enzyme into a nascent polynucleotide or polynucleotide analog chain. Typical enzymatically-incorporatable nucleotides and nucleotide analogs are those in which the sugar is a pentose. Preferred enzymatically-incorporatable nucleotides are those in which the nucleobase is a purine, a 7-deazapurine, a pyrimidine, a normal nucleobase or a common analog thereof and the pentose sugar is a pentose-5'-triphosphate, such as NTPs, dNTPs and ddNTPs.

"Enzymatically-Extendable Nucleotide or Nucleotide Analog:" refers to an enzymatically-incorporatable nucleotide or nucleotide analog that, once incorporated into the nascent polynucleotide or polynucleotide analog chain, supports incorporation of further nucleotides or nucleotide analogs. Thus, enzymatically-extendable nucleotides or nucleotide analogs have a hydroxyl group that is capable of forming a covalent linkage with another, subsequent nucleotide or nucleotide analog. Typical enzymatically-extendable nucleotides and nucleotide analogs are those in which the sugar is a pentose. Preferred enzymatically-extendable nucleotides are those in which the nucleobase is a purine, a 7-deazapurine, a pyrimidine, a normal nucleobase or a common analog thereof and the pentose sugar is a 3'-hydroxypentose-5'-triphosphate, such as NTPs and dNTPs.

A mixture of enzymatically-extendable nucleotides or nucleotide analogs is said to support continuous primer extension when the mixture contains an enzymatically-extendable nucleotide or nucleotide analog complementary to each base of the template polynucleotide, e.g., a mixture of dATP, dGTP, dCTP and dUTP or dTTP.

"Terminator:" refers to an enzymatically-incorporatable nucleotide or nucleotide analog that, once incorporated into the nascent polynucleotide chain, terminates further chain extension. Typical terminators are those in which the nucleobase is a purine, a 7-deaza-purine, a pyrimidine, a normal nucleobase or a common analog thereof and the sugar moiety is a pentose which includes a 3'-substituent that blocks further synthesis, such as a ddNTP. Substituents that block further synthesis include, but are not limited to, amino, deoxy, halogen, alkoxy and aryloxy groups. Exemplary terminators include, but are not limited to, those in which the sugar-phosphate ester moiety is 3'-$(C_1-C_6)$alkylribose-5'-triphosphate, 2'-deoxy-3'-$(C_1-C_6)$alkylribose-5'-triphosphate, 2'-deoxy-3'-($C_1$-$C_6$)alkoxyribose-5'-triphosphate, 2'-deoxy-3'-($C_5$-$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate.

"Nucleoside/tide:" refers to a nucleoside and/or a nucleotide and/or a mixture thereof.

"Polynucleotide:" refers to a linear polymeric chain of nucleoside monomer units that are covalently connected to one another by phosphate ester internucleoside linkages. Unless stated otherwise, "polynucleotide" as used herein includes polymers of any length, including oligonucleotides, polynucleotides and nucleic acids as those terms are commonly used in the art. Where polynucleotides of specific size ranges are intended, the number of monomer units is specifically delineated. Thus, polynucleotides according to the invention can range in size from a few monomer units (e.g., 4 to 40), to several hundreds of monomer units, to several thousands of monomer units, or even more monomer units. Whenever a polynucleotide is represented by a sequence of letters, e.g. "ATGCCTG," it will be understood that the sequence is presented in the 5'→3' direction. 2'-Deoxyribopolynucleotides are preceded with the letter "d," e.g. "d(ATGCCTG)."

Polynucleotides may be comprised of a single type of sugar moiety, as in the case of RNA and DNA, or mixtures of different sugar moieties, as in the case of RNA/DNA chimeras. Preferred polynucleotides are ribopolynucleotides and 2'-deoxyribopolynucleotides according to the structural formulae below:

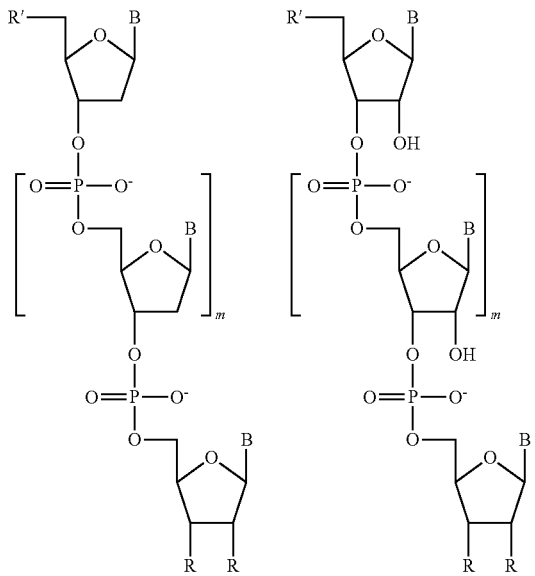

wherein:
each B is independently a nucleobase, preferably a purine, a 7-deazapurine, a pyrimidine, a normal nucleobase or a common analog thereof;
each m defines the length of the respective polynucleotide and can range from zero to thousands, to tens of thousands, or even more;
each R is independently selected from the group consisting of hydrogen, halogen, —R", —OR", and —NR"R", where each R" is independently ($C_1$-$C_6$) alkyl or ($C_5$-$C_{14}$) aryl, or two adjacent Rs are taken together to form a bond such that the ribose sugar is 2',3'-didehydroribose; and
each R' is independently hydroxyl or

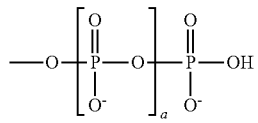

where a is zero, one or two.

In the preferred ribopolynucleotides and 2'-deoxyribopolynucleotides illustrated above, the nucleobases B are covalently attached to the C1' carbon of the sugar moiety as previously described.

"Polynucleotide Analog:" refers to a polynucleotide in which at least one nucleoside monomer unit is a nucleoside analog and/or at least one phosphate ester internucleoside linkage is a phosphate ester analog, as previously defined. Also included within the definition of polynucleotide analogs are polymers in which the phosphate ester and/or sugar phosphate ester internucleoside linkages are replaced with other types of linkages, such as N-(2-aminoethyl)-glycine amides and other amides (see, e.g., Nielsen et al., 1991, Science 254:1497-1500; WO 92/20702; U.S. Pat. No. 5,719,262; U.S. Pat. No. 5,698,685; morpholinos (see U.S. Pat. No. 5,698, 685; U.S. Pat. No. 5,378,841; U.S. Pat. No. 5,185,144); carbamates (see Stirchak & Summerton, 1987, J. Org. Chem. 52:4202); methylene(methylimino) (see Vasseur et al., 1992, J. Am. Chem. Soc. 114:4006); 3'-thioformacetals (see Jones et al., 1993, J. Org. Chem. 58:2983); sulfamates (see U.S. Pat. No. 5,470,967); and others (see, e.g., U.S. Pat. No. 5,817,781; Frier & Altman, 1997, Nucl. Acids Res. 25:4429 and the references cited therein).

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkenyl" and/or "alkynyl" is used, as defined below. In preferred embodiments, the alkyl groups are ($C_1$-$C_6$) alkyl.

"Alkanyl:" refers to a saturated branched, straight-chain or cyclic alkyl radical derived by the removal of one hydrogen atom from a single carbon atom of a parent alkane. Typical alkanyl groups include, but are not limited to, methanyl; ethenyl; propanyls such as propan-1-yl, propan-2-yl(isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are ($C_1$-$C_6$) alkanyl.

"Alkenyl:" refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is $(C_2-C_6)$ alkenyl.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc.; and the like. In preferred embodiments, the alkynyl group is $(C_2-C_6)$ alkynyl.

"Alkyldiyl:" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is $(C_1-C_6)$ alkyldiyl. Also preferred are saturated acyclic alkanyldiyl radicals in which the radical centers are at the terminal carbons, e.g., methandiyl (methano); ethan-1,2-diyl(ethano); propan-1,3-diyl(propano); butan-1,4-diyl(butano); and the like (also referred to as alkylenos, defined infra).

"Alkyleno:" refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In preferred embodiments, the alkyleno group is $(C_1-C_6)$ alkyleno.

"Heteroalkyl, Heteroalkanyl, Heteroalkenyl, Heteroalkanyl, Heteroalkyldiyl and Heteroalkyleno:" refer to alkyl, alkanyl, alkenyl, alkynyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, —O—O—, —S—S—, —O—S—, —NR'—, =N—N=, —N=N—, —N(O)N—, —N=N—NR'—, —PH—, —P(O)$_2$—, —O—P(O)$_2$—, —SH$_2$—, —S(O)$_2$—, —SnH$_2$— an the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

"Acyclic Heteroatomic Bridge:" refers to a divalent bridge in which the backbone atoms are exclusively heteroatoms. Typical acyclic heteroatomic bridges include, but are not limited to, any of the various heteroatomic groups listed above, either alone or in combinations.

"Parent Aromatic Ring System:" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octane, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is $(C_5-C_{14})$ aryl, with $(C_5-C_{10})$ being even more preferred. Particularly preferred aryls are phenyl and naphthyl.

"Aryldiyl:" refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryldiyl group is $(C_5-C_{14})$ aryldiyl, with $(C_5-C_{10})$ being even more preferred. The most preferred aryldiyl groups are divalent radicals derived from benzene and naphthalene, especially phena-1,4-diyl, naphtha-2,6-diyl and naphtha-2,7-diyl.

"Aryleno:" refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure:

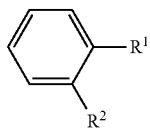

wherein:
R$^1$, when taken alone is hydrogen, or when taken together with R$^2$ is (C$_5$-C$_{14}$) aryleno; and
R$^2$, when taken alone is hydrogen, or when taken together with R$^1$ is (C$_5$-C$_{14}$) aryleno.

When R$^1$ and R$^2$ are each hydrogen, the resultant compound is benzene. When R$^1$ taken together with R$^2$ is C$_6$ aryleno (benzeno), the resultant compound is naphthalene. When R$^1$ taken together with R$^2$ is C$_{10}$ aryleno (naphthaleno), the resultant compound is anthracene or phenanthrene. Typical aryleno groups include, but are not limited to, aceanthryleno, acenaphthyleno, acephenanthyleno, anthraceno, azuleno, benzeno (benzo), chryseno, coroneno, fluorantheno, fluoreno, hexaceno, hexapheno, hexyleno, as-indaceno, s-indaceno, indeno, naphthalene (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2] benzo), [1,2]naphthaleno, [2,3]naphthaleno, etc. Thus, in the above example, when R$^1$ taken together with R$^2$ is [2,3]naphthaleno, the resultant compound is anthracene. When R$^1$ taken together with R$^2$ is [1,2]naphthaleno, the resultant compound is phenanthrene. In a preferred embodiment, the aryleno group is (C$_5$-C$_{14}$), with (C$_5$-C$_{10}$) being even more preferred.

"Arylaryl:" refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenylnaphthyl, binaphthyl, biphenyl-naphthyl, and the like. When the number of carbon atoms comprising an arylaryl group is specified, the numbers refer to the carbon atoms comprising each parent aromatic ring. For example, (C$_5$-C$_{14}$) arylaryl is an arylaryl group in which each aromatic ring comprises from 5 to 14 carbons, e.g., biphenyl, triphenyl, binaphthyl, phenylnaphthyl, etc. Preferably, each parent aromatic ring system of an arylaryl group is independently a (C$_5$-C$_{14}$) aromatic, more preferably a (C$_5$-C$_{10}$) aromatic. Also preferred are arylaryl groups in which all of the parent aromatic ring systems are identical, e.g., biphenyl, triphenyl, binaphthyl, trinaphthyl, etc.

"Biaryl:" refers to an arylaryl radical having two identical parent aromatic systems joined directly together by a single bond. Typical biaryl groups include, but are not limited to, biphenyl, binaphthyl, bianthracyl, and the like. Preferably, the aromatic ring systems are (C$_5$-C$_{14}$) aromatic rings, more preferably (C$_5$-C$_{10}$) aromatic rings. A particularly preferred biaryl group is biphenyl.

"Arylalkyl:" refers to an acyclic alkyl radical in which one of the hydrogen atoms bonded to a carbon atom, typically a terminal or spa carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C$_6$-C$_{20}$) arylalkyl, e.g., the alkanyl, alkenyl or alkynyl moiety of the arylalkyl group is (C$_1$-C$_6$) and the aryl moiety is (C$_5$-C$_{14}$). In particularly preferred embodiments the arylalkyl group is (C$_6$-C$_{13}$), e.g., the alkanyl, alkenyl or alkynyl moiety of the arylalkyl group is (C$_1$-C$_3$) and the aryl moiety is (C$_5$-C$_{10}$).

"Parent Heteroaromatic Ring System:" refers to a parent aromatic ring system in which one or more carbon atoms (and any necessary associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more rings are aromatic and one or more of the rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoine, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-14 membered heteroaryl, with 5-10 membered heteroaryl being particularly preferred. The most preferred heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

"Heteroaryldiyl:" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryldiyl group is 5-14 membered heteroaryldiyl, with 5-10 membered being particularly preferred. The most preferred heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

"Heteroaryleno:" refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure:

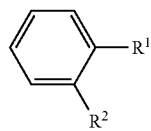

wherein:
$R^1$, when taken alone is hydrogen, or when taken together with $R^2$ is 5-14 membered heteroaryleno; and
$R^2$, when taken alone is hydrogen, or when taken together with $R^1$ is 5-14 membered heteroaryleno;

When $R^1$ and $R^2$ are each hydrogen, the resultant compound is benzene. When $R^1$ taken together with $R^2$ is a 6-membered heteroaryleno pyridino), the resultant compound is isoquinoline, quinoline or quinolizine. When $R^1$ taken together with $R^2$ is a 10-membered heteroaryleno (e.g., isoquinoline), the resultant compound is, e.g., acridine or phenanthridine. Typical heteroaryleno groups include, but are not limited to, acridino, carbazolo, β-carbolino, chromeno, cinnolino, furan, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, and the like. Where a specific connectivity is intended, the involved bridging atoms (of the heteroaryleno bridge) are denoted in brackets, e.g., [1,2]pyridino, [2,3]pyridino, [3,4]pyridino, etc. Thus, in the above example, when $R^1$ taken together with $R^2$ is [1,2]pyridino, the resultant compound is quinolizine. When $R^1$ taken together with $R^2$ is [2,3]pyridino, the resultant compound is quinoline. When $R^1$ taken together with $R^2$ is [3,4]pyridino, the resultant compound is isoquinoline. In preferred embodiments, the heteroaryleno group is 5-14 membered heteroaryleno, with 5-10 membered being even more preferred. The most preferred heteroaryleno radicals are those derived from parent heteroaromatic ring systems in which any ring heteroatoms are nitrogens, such as imidazolo, indolo, indazolo, isoindolo, naphthyridino, pteridino, isoquinolino, phthalazino, purino, pyrazolo, pyrazino, pyridazino, pyridino, pyrrolo, quinazolino, quinolino, etc.

"Heteroaryl-Heteroaryl:" refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. When the number of ring atoms are specified, the numbers refer to the number of atoms comprising each parent heteroaromatic ring systems. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. Preferably, each parent heteroaromatic ring system is independently a 5-14 membered heteroaromatic, more preferably a 5-10 membered heteroaromatic. Also preferred are heteroaryl-heteroaryl groups in which all of the parent heteroaromatic ring systems are identical. The most preferred heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

"Biheteroaryl:" refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-14 membered heteroaromatic rings, more preferably 5-10 membered heteroaromatic rings. The most preferred biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

"Heteroarylalkyl:" refers to an acyclic alkyl radical in which one of the hydrogen atoms bonded to a carbon atom, typically a terminal or sp³ carbon atom, is replaced with a heteroaryl radical. Where specific alkyl moieties are intended, the nomenclature heteroarylalkanyl, heteroarylakenyl and/or heterorylalkynyl is used. In preferred embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In particularly preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

"Substituted:" refers to a radical in which one or more hydrogen atoms are each independently replaced with the same or different substituent(s). Typical substituents include, but are not limited to, —X, —R, —O⁻, =O, —OR, —O—OR, —SR, —S⁻, =S, —NRR, =NR, perhalo ($C_1$-$C_6$) alkyl, —CX₃, —CF₃, —CN, —OCN, —SCN, —NCO, —NCS, —NO, —NO₂, =N₂, =N₂, —N₃, —S(O)₂O⁻, —S(O)₂OH, —S(O)₂R, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F or —Cl) and each R is independently hydrogen, alkyl, alkanyl, alkenyl, alkanyl, aryl, arylalkyl, arylaryl, heteroaryl, heteroarylalkyl or heteroaryl-heteroaryl, as defined herein. The actual substituent substituting any particular group will depend upon the identity of the group being substituted.

"Parent Xanthene Ring:" refers to a heteroaromatic ring system of a type typically found in the xanthene class of fluorescent dyes (which includes rhodamine and fluorescein dyes, defined infra), i.e., a heteroaromatic ring system having the general structure:

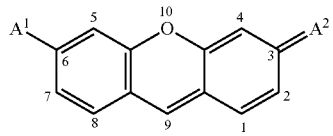

In the parent xanthene ring depicted above, A¹ is —OH or —NH₂ and A² is =O or =NH₂⁺. When A¹ is —OH and A² is =O, the parent xanthene ring is a fluorescein-type parent xanthene ring, which is defined in more detail, infra. When A¹ is —NH₂ and A² is =NH₂⁺, the parent xanthene ring is a rhodamine-type parent xanthene ring, which is defined in more detail, infra. When A¹ is —NH₂ and A² is =O, the parent xanthene ring is a rhodol-type parent xanthene ring. In the parent xanthene ring depicted above, one or both nitrogens of A¹ and A² (when present) and/or one or more of the carbon atoms at positions C1, C2, C4, C5, C7 and C8, can be independently substituted with a wide variety of the same or different substituents, as is well known in the art. Typical substituents include, but are not limited to, —X, —R, —OR, —SR, —NRR, perhalo ($C_1$-$C_6$) alkyl, —CX₃, —CF₃, —CN, —OCN, —SCN, —NCO, —NCS, —NO, —NO₂, —N₃, —S(O)₂O⁻, —S(O)₂OH, —S(O)₂R, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F or —Cl) and each R is independently hydrogen, ($C_1$-$C_6$) alkyl, ($C_1$-$C_6$) alkanyl, ($C_1$-$C_6$) alkenyl, ($C_1$-$C_6$) alkynyl, ($C_5$-$C_{20}$) aryl, ($C_6$-$C_{26}$) arylalkyl, ($C_5$-$C_{20}$) arylaryl, heteroaryl, 6-26 membered heteroarylalkyl or 5-20 membered heteroaryl-heteroaryl. Moreover, the C1 and C2 substituents and/or the C7 and C8 substituents can be taken together to form substituted or =substituted ($C_5$-$C_{20}$) aryleno bridges. Generally, substituents groups which do not tend to quench the fluorescence of the parent xanthene ring are preferred, but in some embodiments quenching substituents may be desirable. Substituents that tend to quench fluorescence of parent xanthene rings are electron-withdrawing groups, such as —NO₂, —F, —Br, —CN and —CF₃.

When A¹ is —NH₂ and/or A² is =NH₂⁺, the xanthene nitrogens can be included in bridges involving the same nitrogen atom or adjacent carbon atoms, e.g., ($C_1$-$C_{12}$) alkyldiyl, ($C_1$-$C_{12}$) alkyleno, 2-12 membered heteroalkyldiyl and/or 2-12 membered heteroalkyleno bridges.

Any of the substituents substituting carbons C1, C2, C4, C5, C7 or C8 and/or the xanthene nitrogen atoms (when present) can be further substituted with one or more of the same or different substituents, which are typically selected from the group consisting of —X, —R', =O, —OR', —SR', =S, —NR'R', =NR', —CX₃, —CN, —OCN, —SCN, —NCO, —NCS, —NO, —NO₂, =N₂, —N₃, —NHOH, —S(O)₂O⁻, —S(O)₂OH, —S(O)₂R', —P(O)(O⁻)₂, —P(O)(OH)₂, —C(O)R', —C(O)X, —C(S)R', —C(S)X, —C(O)OR', —C(O)O⁻, —C(S)OR', —C(O)SR', —C(S)SR', —C(O)NR'R', —C(S)NR'R' and —C(NR)NR'R', where each X is independently a halogen (preferably —F or —Cl) and each R' is independently hydrogen, ($C_1$-$C_6$) alkyl, 2-6 membered heteroalkyl, ($C_5$-$C_{14}$) aryl or heteroaryl.

Exemplary parent xanthene rings include, but are not limited to, rhodamine-type parent xanthene rings and fluorescein-type parent xanthene rings, each of which is defined in more detail, infra.

"Rhodamine-Type Parent Xanthene Ring:" refers to a parent xanthene ring in which A¹ is —NH, and A² is =NH₂⁺, i.e., a parent xanthene ring having the general structure:

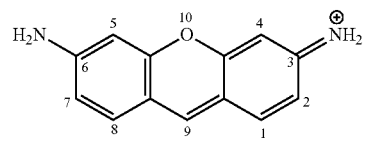

In the rhodamine-type parent xanthene ring depicted above, one or both nitrogens and/or one or more of the carbons at positions C1, C2, C4, C5, C7 or C8 can be independently substituted with a wide variety of the same or different substituents, as previously described for the parent xanthene rings. Exemplary rhodamine-type parent xanthene rings include, but are not limited to, the xanthene rings of the rhodamine dyes described in U.S. Pat. No. 5,936,087; U.S. Pat. No. 5,750,409; U.S. Pat. No. 5,366,860; U.S. Pat. No. 5,231,191; U.S. Pat. No. 5,840,999; U.S. Pat. No. 5,847,162; U.S. application Ser. No. 09/277,793, filed Mar. 27, 1999; PCT Publication WC) 97/36960; PCT Publication WO 99/27020; Sauer et al., 1995, J. Fluorescence 5(3):247-261; Arden-Jacob, 1993, *Neue Lanwellige Xanthen-Farbstoffe für Fluoreszenzsonden and Farbstoff Laser*, Verlag Shaker, Germany; and Lee et al., 1992, Nucl. Acids Res. 20(10):2471-2483. Also included within the definition of "rhodamine-type parent xanthene ring" are the extended-conjugation xanthene rings of the extended rhodamine dyes described in U.S. application Ser. No. 09/325,243, filed Jun. 3, 1999.

"Fluorescein-Type Parent Xanthene Ring:" refers to a parent xanthene ring in which $A^1$ is —OH and $A^2$ is =O, i.e., a parent xanthene ring having the structure:

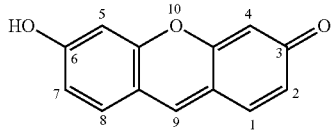

In the fluorescein-type parent xanthene ring depicted above, one or more of the carbons at positions C1, C2, C4, C5, C7 or C8 can be independently substituted with a wide variety of the same or different substituents, as previously described for the parent xanthene rings. Exemplary fluorescein-type parent xanthene rings include, but are not limited to, the xanthene rings of the fluorescein dyes described in U.S. Pat. No. 4,439,356; U.S. Pat. No. 4,481,136; U.S. Pat. No. 5,188,934; U.S. Pat. No. 5,654,442; U.S. Pat. No. 5,840,999; WO 99/16832; and EP 0 050 684. Also included within the definition of "fluorescein-type parent xanthene ring" are the extended xanthene rings of the fluorescein dyes described in U.S. Pat. No. 5,750,409 and U.S. Pat. No. 5,066,580.

"Xanthene Dye:" refers to a class of fluorescent dyes which consist of a parent xanthene ring substituted at the xanthene C-9 carbon with a substituted phenyl ring or other, typically acyclic, substituent. Common substituted phenyl rings found in xanthene dyes include, e.g., 2-carboxyphenyl, dihalo-2-carboxyphenyl, tetrahalo-2-carboxyphenyl, 2-ethoxycarbonylphenyl, dihalo-2-ethoxycarbonylphenyl and tetrahalo-2-ethoxycarbonylphenyl. Common acyclic substituents found in xanthene dyes include, e.g., carboxyethyl and perfluoroalkyl (e.g., trifluoromethyl, pentafluoroethyl and heptafluoropropyl). Typical xanthene dyes include the fluorescein dyes and the rhodamine dyes, which are described in more detail, infra.

"Rhodamine Dye:" refers to the subclass of xanthene dyes in which the xanthene ring is a rhodamine-type parent xanthene ring. Typical rhodamine dyes include, but are not limited to, rhodamine B, 5-carboxyrhodamine, rhodamine X (ROX), 4,7-dichlororhodamine X (dROX), rhodamine 6G (R6G), rhodamine 110 (R110), 4,7-dichlororhodamine 110 (dR110), tetramethyl rhodamine (TAMRA) and 4,7-dichloro-tetramethylrhodamine (dTAMRA). Additional typical rhodamine dyes can be found, for example, in U.S. Pat. No. 5,936,087; U.S. Pat. No. 5,750,409; U.S. Pat. No. 5,366,860; U.S. Pat. No. 5,231,191; U.S. Pat. No. 5,840,999; U.S. Pat. No. 5,847,162; U.S. application Ser. No. 09/038,191, filed Mar. 10, 1998; U.S. application Ser. No. 09/277,793, filed Mar. 27, 1999; U.S. application Ser. No. 09/325,243, filed Jun. 3, 1999; PCT Publication WO 97/36960; PCT Publication WO 99/27020; Sauer et al., 1995, J. Fluorescence 5(3): 247-261; Arden-Jacob, 1993, *Neue Lanwellige Xanthen-Farbstoffe für Fluoreszerasonden and Farbstoff Laser*, Verlag Shaker, Germany; and Lee et al., 1992, Nucl. Acids Res. 20(10):2471-2483.

"Fluorescein Dye:" refers to the subclass of xanthene dyes in which the parent xanthene ring is a fluorescein-type parent xanthene ring. Typical fluorescein dyes include, but are not limited to, 5-carboxyfluorescein (5-FAM), 6-carboxyfluorescein (6-FAM). Additional typical fluorescein dyes can be found, for example, in U.S. Pat. No. 5,750,409; U.S. Pat. No. 5,066,580; U.S. Pat. No. 4,439,356; U.S. Pat. No. 4,481,136; U.S. Pat. No. 5,188,934; U.S. Pat. No. 5,654,442; U.S. Pat. No. 5,840,999; PCT publication WO 99/16832; EP 0 050 684; and U.S. application Ser. No. 08/942,067, filed Oct. 1, 1997.

5.3 The Rhodamine Dye Compounds

5.3.1 The Compounds Per Se

The rhodamine dyes of the invention are generally rhodamine-type parent xanthene rings substituted at the xanthene C9 position with a new bottom ring. The new bottom ring is a phenyl group which bears five substituents: an ortho carboxyl or sulfonate group (or salts thereof); one to three aminopyridinium ($Pyr^+$) groups; and one alkylthio, arylthio or heteroarylthio group. The $Pyr^+$ groups, which may be the same or different, are typically the same and are attached to the new bottom ring via the pyridinium ring nitrogen. The alkylthio, arylthio or heteroarylthio group is attached to the new bottom ring via the sulfur atom. As previously described in the Summary section, the aminopyridinium and/or alkylthio, arylthio or heteroarylthio groups may be substituted or unsubstituted. The rhodamine dyes may also include an optional linking moiety, described in more detail, infra.

Currently available red-emitting fluorescent dyes, such as rhodamines and cyanines, suffer from undesirable water-solubility and/or photostability characteristics. For example, due to their hydrophobic nature, most commercially-available rhodamine dyes are somewhat insoluble in water. Red-emitting cyanine dyes such as Cy5, although water-soluble, are photo unstable. Thus, available red-emitting rhodamine and cyanine dyes are not well-suited for many aqueous-based biological applications, such as cell staining or nucleic acid sequencing.

By virtue or their new bottom rings, the rhodamine dyes of the invention overcome these limitations. While not intending to be bound by any particular theory, it is believed that the $Pyr^+$ groups substituting the new bottom ring render the dyes highly water-soluble. Quite importantly, rhodamine dyes substituted with these new bottom rings retain their characteristic photostability. Moreover, the new bottom ring tends to shift the emissions spectral properties of the dyes to the red by about 5-30 nm, as compared with corresponding rhodamines dyes comprising a conventional bottom ring. Thus, the rhodamine dyes of the invention are ideally suited for use as water-soluble laser dyes and in aqueous-based biological applications such as cell staining and nucleic acid sequencing. Quite significantly, when used to label terminators in nucleic acid sequencing applications, the new rhodamine dyes of the invention do not effect obscuring impurities which electrophoretically migrate in the range of DNA sequencing fragments. Obscuring impurities are commonly observed with conventionally-labeled terminators and are generally thought to be caused by unincorporated labelled-terminators. As a consequence, sequencing data obtained with terminators labeled with the new rhodamine dyes of the invention is typically much higher in quality than that obtained with conventional terminators. Sequencing reactions obtained with terminators labeled with the new rhodamine dyes of the present invention may require less sample purification, or "clean up" than those employing conventional terminators.

The rhodamine dyes of the invention are generally compounds according to structural formula (I):

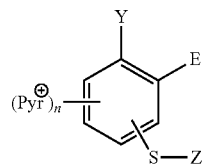

including any associated counterions, wherein:

E is carboxylic acid, sulfonic acid, or a salt thereof;

Y is a rhodamine-type parent xanthene ring connected to the illustrated fully substituted phenyl ring at the C-9 carbon;

each $Pyr^+$ is independently a substituted or unsubstituted aminopyridinium group connected to the illustrated phenyl ring via the pyridinium ring nitrogen;

S is sulfur, n is one, two, or three; and

Z a substituted or unsubstituted ($C_1$-$C_{12}$)alkyl, ($C_5$-$C_{14}$) aryl or heteroaryl.

The invention is based, in part, on the discovery that replacing the ring or substituent attached to the xanthene C-9 carbon of conventional rhodamine dyes with the new bottom rings described herein yields rhodamine dyes having superior water-solubility, photo stability and/or excitation and emission spectral properties. As a consequence, those of skill in the art will recognized that in the rhodamine dyes of structural formula (I), rhodamine-type parent xanthene ring Y can be derived from virtually any fluorescent rhodamine dye that is now known or that will be later developed. Exemplary rhodamine-type parent xanthene rings that can comprise Y include, but are not limited to, any of the substituted or unsubstituted xanthene rings of the rhodamine dyes described in U.S. Pat. No. 5,936,087; U.S. Pat. No. 5,750,409; U.S. Pat. No. 5,366,860; U.S. Pat. No. 5,231,191; U.S. Pat. No. 5,840,999; U.S. Pat. No. 5,847,162; U.S. application Ser. No. 09/038,191, filed Mar. 10, 1998; U.S. application Ser. No. 09/277,793, filed Mar. 27, 1999; U.S. application Ser. No. 09/325,243, filed Jun. 3, 1999; PCT Publication WO 97/36960; PCT Publication WO 99/27020; Sauer at al., 1995, J. Fluorescence 5(3):247-261; Arden-Jacob, 1993, *Neue Lanwellige Wanthen-Farbstoffe für Fluoreszenzsonden and Farbstoff Laser*, Verlag Shaker, Germany, and Lee et al., 1992, Nucl. Acids Res. 20(10):2471-2483, the disclosures of which are incorporated herein by reference.

While the dyes of structural formula (I) are useful in virtually any aqueous-based applications employing red-emitting fluorescent dyes, such as, for example, as water-soluble laser dyes, rhodamine-s according to structural formula (I) which incorporate one or more optional linking moieties are particularly useful, as they can be specifically and/or permanently conjugated to other compounds and/or substances so as to label the compounds or substances for subsequent detection. The linking moieties are attached to the rhodamine-type parent xanthene ring, either at a xanthene nitrogen, the xanthene C4 carbon, and/or the Z substituent. Thus, preferred rhodamine dyes of the invention are compounds according to structural formula (I) in which the C4 carbon atom of Y, one or both nitrogen atoms of Y and/or substituent Z are substituted with a linking moiety of the formula -L-, wherein L is a bond or linker. When the dye includes multiple linkers L, each may be the same or different.

The nature of linker L will depend upon the particular application, point of attachment and type of conjugation desired. Linker L may be attached directly to the dye, or it may be spaced away from the dye through one or more intervening atoms that serve as a linker. In the former embodiment, L represents a bond. In the latter embodiment, L represents a linker of more than one atom. The linker can be hydrophilic or hydrophobic, long or short, rigid, semirigid or flexible, depending upon the particular application. The linker can be optionally substituted with one or more substituents or one or more additional linking groups, which may be the same or different, thereby providing a "polyvalent" linking moiety capable of conjugating with multiple molecules or substances. Preferably, however, linker L does not include such additional substituents or linking groups.

A wide variety of linkers L comprised of stable bonds are known in the art, and include by way of example and not limitation, alkyldiyls, substituted alkyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted atylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, substituted heteroaryl-heteroalkyldiyls, and the like. Thus, linker L may include single, double, triple or aromatic carbon-carbon bonds, nitrogen-nitrogen bonds, carbon-nitrogen, carbon-oxygen bonds and/or carbon-sulfur bonds, and may therefore include functionalities such as carbonyls, ethers, thioethers, carboxamides, sulfonamides, ureas, urethanes, hydrazines, etc. In one embodiment, linker L has from 1-20 non-hydrogen atoms selected from the group consisting of C, N, O, and S and is composed of any combination of ether, thioether, amine, ester, carboxamide, sulfonamides, hydrazide, aromatic and heteroaromatic bonds.

Choosing a linker having properties suitable for a particular application is within the capabilities of those having skill in the art. For example, where a rigid linker is desired, L may be a rigid polypeptide such as polyproline, a rigid polyunsaturated alkyldiyl or an aryldiyl, biaryldiyl, arylarydiyl, arylalkyldiyl, heteroaryldiyl, biheteroaryldiyl, heteroarylalkyldiyl, heteroaryl-heteroaryldiyl, etc. Where a flexible linker is desired, L may be a flexible polypeptide such as polyglycine or a flexible saturated alkanyldiyl or heteroalkanyldiyl. Hydrophilic linkers may be, for example, polyalcohols or polyethers such as polyalkyleneglycols. Hydrophobic linkers may be, for example, alkyldiyls or aryldiyls.

Linkers suitable for use in most biological applications include ($C_1$-$C_{12}$)alkyldiyls, particularly alkanylenos such as methano (—$CH_2$—), ethano (—$CH_2$—$CH_2$—), propano (—$CH_2$—$CH_2$—$CH_2$), butano (—$CH_2$—$CH_2$—$CH_2$—$CH_2$—), pentano (—$CH_2$—$CH_2$—$CH_2$—$CH_2$—$CH_2$) and hexano (—$CH_2$—$CH_2$—$CH_2$—$CH_2$—$CH_2$—$CH_2$—); ($C_5$-$C_{20}$) aryldiyls, particularly phena-1,3-diyl

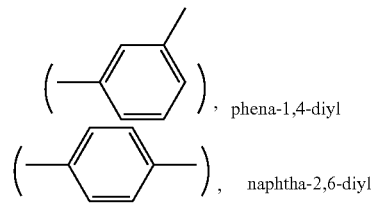

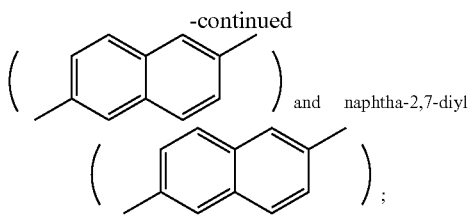 and naphtha-2,7-diyl;

and ($C_6$-$C_{26}$) arylalkyldiyls, particularly those having the structural formula —$(CHO_2)_i$-φ- or —$(CH_2)_i$-Ψ-, where each i is independently an integer from 1 to 6, φ is phenyldiyl (especially phena-1,3-diyl or phena-1,4-diyl) and Ψ is naphthyldiyl (especially naphtha-2,6-diyl or naphtha-2,7-diyl). Rigid linkers that are suitable for attaching the dyes of the invention to one another or to other dyes to create energy-transfer dye pairs (described in more detail, infra) include —$(CH_2)_i$—NR"—C(O)-φ and —$(CH_2)_i$—NR"—C(O)-Ψ, where i, R", φ and Ψ are as previously defined. Particularly preferred are those linkers in which i is 1. Analogs of all of these linkers L containing one or more heteroatomic groups, particularly those selected from the group consisting of O, S, N and NR", where R" is hydrogen or ($C_1$-$C_6$) alkyl, can also be conveniently used to space linkers from the rhodamine dyes of the invention. Linkers L tailored to specific applications are discussed in more detail, infra.

Rhodamine dyes including a linking moiety can be conjugated to a variety of different molecules and substances using a plethora of different conjugation means. For example, the conjugation can be mediated via hydrophobic interactions, ionic attraction, through the use of pairs of specific binding molecules such as biotin and avidin/streptavidin or through covalent attachment. When conjugation via hydrophobic interactions is desired, linker L is a hydrophobic moiety that is capable of forming hydrophobic interactions with a hydrophobic moiety on the molecule or substance to be conjugated. Typical hydrophobic moieties include, but are not limited to, unsubstituted and substituted aryl, arylalkyl, arylaryl, heteroaryl, heteroarylaklyl and heteroaryl-heteroaryl groups. When the hydrophobic moiety is substituted, the substituents are preferably nonpolar, more preferably hydrophobic. Suitable hydrophobic moieties for forming non-covalent conjugates will be apparent to those of skill in the art.

When conjugation via ionic attraction is desired, L is a charged moiety having a net charge of a polarity opposite to a net charge on the molecule or substance to be conjugated. Typical charged moieties include, by way of example and not limitation, quaternary ammoniums, carboxylates and sulfonates, including salts thereof. A variety of cyclic quaternary ammoniums that are suitable for use in linkers are described in U.S. Pat. No. 5,863,753 (see, e.g., Cols. 8-9), The disclosure of which is incorporated herein by reference.

When conjugation via pairs of specific binding molecules such as biotin and avidin/streptavidin is desired, L will constitute one member of the binding pair. The molecule or substance to be conjugated will bear the other member of the binding pair. Where one of the members of the specific binding pair is a small molecule, such as biotin or a hormone, that member preferably comprises L. A variety of biotins capable of being covalently linked to reactive functional groups such as amines are commercially available (e.g., Molecular Probes, Eugene, Oreg.). These biotins can be incorporated into the dyes of the invention to yield biotin-labeled dyes suitable for non-covalent conjugation to a variety of avidin/streptavidin-labeled molecules or substances.

Preferably, L is capable of mediating conjugation via covalent attachment. In this preferred embodiment, L bears a reactive functional group ($R_x$). Covalent conjugates are obtained by reacting a rhodamine dye of the invention including a reactive group $R_x$ with a molecule or substance that contains, or is modified to contain, one or more functional groups $F_x$ that are complementary to reactive group $R_x$.

The exact identities of $R_x$ and $F_x$ will depend upon the nature of the desired covalent linkage and the chemistry used to form the covalent linkage. Generally, reactive group $R_x$ is a functional group that is capable of reacting with a complementary functional group $F_x$ under specified reaction conditions to form a covalent linkage. However, those of skill in the art will recognize that a variety of functional groups that are typically unreactive under certain reaction conditions can be activated to become reactive. Groups that can be activated to become reactive include, e.g., carboxylic acids and esters, including salts thereof. Such groups are referred to herein as "activatable precursors" and are specifically intended to be included within the expression "reactive group."

Pairs of reactive groups $R_x$ and complementary groups $F_x$ suitable for forming covalent linkages with one another under a variety of different reaction conditions are well-known. Any of these complementary pairs of groups can be used to covalently conjugate the rhodamine dyes of the invention to other compounds or substances. In one convenient embodiment, reactive group $R_x$ and complementary functional group $F_x$ comprise complementary electrophiles and nucleophiles (or their respective activatable precursors). In another convenient embodiment, reactive group $R_x$ is a photoactivatable group that becomes chemically reactive only after illumination with light of an appropriate wavelength and complementary functional group $F_x$ is a group capable forming a covalent linkage with the chemically reactive species. Such photoactivatable groups can be conveniently used to photo cross-link the rhodamine dyes of the invention to other molecules and/or substances.

As understood in the art, "activated esters" generally have the formula —C(O)Ω, where Ω is a good leaving group. Exemplary good leaving groups include, by way of example and not limitation: oxysuccinimidyl; N-succinimidyl; oxysulfosuccinimidyl; 1-oxybenzotriazolyl; and —$OR^a$, where $R^a$ is selected from the group consisting of ($C_4$-$C_{20}$) cycloalkyl (e.g., cyclohexyl), heterocycloalkyl, ($C_5$-$C_{20}$) aryl, ($C_5$-$C_{20}$) aryl substituted with one or more of the same or different electron-withdrawing groups (e.g., $NO_2$, —F, —Cl, —CN, —$CF_3$, etc.), heteroaryl, and heteroaryl substituted with one or more of the same or different electron-withdrawing groups, n-dialkylaminoalkyls (e.g., 3-dimethylaminopropyl) and N-morpholinomethyl, or $R^a$ is used to form an anhydride of the formula —$OCOR^b$ or —$OCNR^bNHR^c$, where $R^b$ and $R^c$ are each independently selected form the group consisting of ($C_1$-$C_6$) alkyl, ($C_1$-$C_6$) perhaloalkyl, ($C_1$-$C_6$) perfluoroalkyl and ($C_1$-$C_6$) alkoxy. A preferred activated ester is NHS ester.

Exemplary photoactivatable groups suitable for conjugation via light-activated cross-linking include, but are not limited to, azido (—$N_3$), 4-azido-phenyl and 2-nitro-4-azidophenyl. Conjugation using photoactivatable groups typically involves illuminating a mixture comprising the photoactivatable dyes and the molecule or substance to be conjugated, followed by separation of unreacted dyes and byproducts.

As will be recognized by those of skill in the art, reactive group $R_x$ can comprise any electrophilic, nucleophilic or photoactivatable groups. The selection of reactive group $R_x$ used to covalently conjugate the rhodamine dyes of the invention to the other molecule or substance typically depends upon the identity of the complementary functional group $F_x$ on the molecule or substance to be conjugated. The types of complementary functional groups typically present on molecules or substances to be conjugated include, but are not limited to, amines, thiols, alcohols, phenols, aldehydes, ketones, phosphates, imidazoles, hydrazines, hydroxylamines, mono- and disubstituted amines, halides, epoxides, sulfonate esters, carboxylic acids or carboxylates, or a combination of these groups. A single type of complementary functional group may be available on the molecule or substance (which is typical for polysaccharides), or a variety of different complementary functional groups may be available (e.g. amines, thiols, alcohols, phenols), which is typical for proteins. The molecule or substance may be conjugated to more than one rhodamine dye, which may be the same or different. Although some selectivity can be obtained by carefully controlling the reaction conditions, selectivity of conjugation is best obtained by appropriate choice of reactive group in light of the available complementary functional group(s) $F_x$. In instances where the molecule or substance to be conjugated does not contain available complementary functional group(s) $F_x$, it can be modified to contain such groups using any of a variety of standard techniques.

In a preferred embodiment, reactive group $R_x$ is a group that reacts with, or that can be readily activated to react with, an amine, a thiol or an alcohol. In a particularly preferred embodiment, one of reactive group $R_x$ or complementary functional group $F_r$ is a carboxylic acid (or a salt thereof) or an activated ester, most preferably a N-hydroxysuccinimidyl (NHS) ester, and the other is an amine, preferably a primary amine. The NHS ester may be conveniently obtained by reacting a rhodamine dye of the invention including a carboxylic acid reactive group $R_x$ with N-hydroxysuccinimide in the presence of an activating agent (e.g., dicyclohexylcarbodiimide) according to known methods.

For a discussion of the various reactive groups $R_x$ and respective complementary functional groups $F_x$ that can be conveniently used to covalently conjugate the rhodamine dyes of the invention to a variety of biological and other molecules or substances, as well as reaction conditions under which the conjugation reactions can be carried out, see Haugland, 1996, *Molecular Probes Handbook of Fluorescent Probes and Research Chemicals*, Molecular Probes, Inc.; Brinkley, 1992, Bioconjugate Chem. 3:2 and Garman, 1997, *Non-Radioactive Labelling: A Practical Approach*, Academic Press, London, as well as the references cited in all of the above.

In one illustrative embodiment, rhodamine dyes of the invention which are capable of being covalently conjugated to other compounds and/or substances are compounds according to structural formula (Ia):

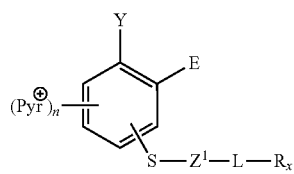

including any associated counter ions, wherein:
E, Y, Pyr$^+$ and S are as previously defined for structural formula (I);
Z$^1$ is a substituted or unsubstituted (C$_1$-C$_{12}$) alkyldiyl, (C$_5$-C$_{14}$) or heteroaryldiyl;

L is a bond or a linker as previously described;
R$_x$ is a reactive group as previously described; and
n is one, two, or three.

In another illustrative embodiment, rhodamine dyes of the invention which are capable of being covalently conjugated to other compounds and/or substances are compounds according to structural formula (Ib):

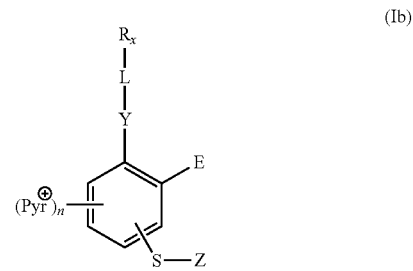

including any associated counterions, wherein:
E, Y, Pyr$^+$, S and Z are as previously defined for structural formula (I);
L and R$_x$ are as previously defined for structural formula (Ia), where L is connected to the C4 carbon atom or a nitrogen atom of Y; and
n is one, two, or three.

While not intending to be bound by any particular theory, it is believed that the Pyr$^+$ groups on the new bottom rings in the compounds of structural formulae (I), (Ia) and (Ib) account for the water-solubility of the rhodamine dyes of the invention.

As will be illustrated more thoroughly below, the Pyr$^+$ groups are introduced into the rhodamine dyes of the invention by displacing fluorine atoms of the corresponding tetrafluororhodamine precursor with the desired aminopyridine reactant, e.g. Scheme (I), using a reaction similar to that described in Weiss, R. et al, 1995, Angew. Chem. Int. Ed. Engl. 34:1319-21; and Koch, A. et al, 1993, Jour. Org. Chem. 58:1409-14. As a consequence, unless mixtures of different aminopyridine reactants are used in the displacement reaction, all of the Pyr$^+$ groups on the new bottom phenyl rings are identical. According to the reaction, the Pyr$^+$ groups are attached to the new bottom phenyl ring via the pyridinium ring nitrogen.

The pyridinium ring carbons may be independently substituted with a wide variety of the same or different substituents. The desired substituents are introduced as substituents on the aminopyridine reactants. These carbons may be substituted with virtually any group, with one caveat: in order to avoid deleteriously affecting the displacement reaction, the pyridine ring carbons should not be directly substituted with electron-withdrawing groups, e.g., —F, —Cl, —CF$_3$, —NO$_2$, —CN, —N$_3$, etc. However, such electron-withdrawing groups can be included on the substituents, as long as it is not attached directly to a pyridine ring carbon. For example, while a pyridine ring carbon should not be directly substituted with —F, —Cl or —CF$_3$, it may be substituted with other, less electronegative or electron-withdrawing, haloalkyls (e.g., —CH$_2$—CH$_2$F). Identifying substituents which are suitably non-electron-withdrawing is within the capabilities of those having skill in the art. Typical groups useful for substituting the pyridinium ring carbons include, but are not limited to, —R, —OR, —SR, —NRR, —S(O)$_2$O$^-$, —S(O)$_2$OH, —S(O)$_2$R, —C(O)R, —C(O)X, —C(S)R, —C(S)X, —C(O)OR, —C(O)O$^-$, —C(S)OR, —C(O)SR, —C(S)SR, —C(O)

NRR, —C(S)NRR and —C(NR)NRR, where each R is independently hydrogen, ($C_1$-$C_6$) alkyl or heteroalkyl, ($C_5$-$C_{14}$) aryl or heteroaryl. The R groups may be further substituted with one or more of the same or different substituents, which are typically selected from the group consisting of —X, —R', =O, —OR', —SR', =S, —NR'R', =NR', —$CX_3$, —CN, —OCN, —SCN, —NCO, —NCS, —NO, —$NO_2$, =$N_2$, —$N_3$, —S(O)$_2$O', —S(O)$_2$OH, —S(O)$_2$R', —C(O)R', —C(O)X, —C(S)R', —C(S)X, —C(O)OR', —C(O)O⁻, —C(S)OR', —C(O)SR', —C(S)SR', —C(O)NR'R', —C(S)NR'R' and —C(NR)NR'R', where each X is independently a halogen (preferably —F or —Cl) and each R' is independently hydrogen, ($C_1$-$C_6$) alkyl, 2-6 membered heteroalkyl, ($C_5$-$C_{14}$) aryl or heteroaryl. Preferably, the pyridinium ring carbons are unsubstituted. When substituted, the most preferred substituents are the same or different ($C_1$-$C_6$) alkyls. Preferably, the pyridinium carbons are unsubstituted. When substituted, the substituents are preferably the same or different ($C_1$-$C_6$) alkyls.

The amino groups of the Pyr⁺ substituents may be a primary, secondary or tertiary amino group, but is typically a tertiary amino. The nitrogen substituents, R, are typically the same or different ($C_1$-$C_6$) alkyl or heteroalkyl. The alkyl or heteroalkyl can be further substituted with one or more of the same or different groups, as previously described for R, above.

Alternatively, the nitrogen atom may be included in a ring structure having from 2 to 5 ring atoms. The ring may contain, in addition to the amino nitrogen atom, one or more of the same or different heteroatoms, which are typically selected from the group consisting of O, S and N. The ring atoms can be further substituted with any of the previously described substituent groups. Preferably, the amino group is dimethylamino or morpholino.

In the compounds of structural formulae (I), (Ia) and (Ib), the Z or substituent may also be substituted or unsubstituted, but is preferably unsubstituted. When Z is an alkyl or $Z^1$ is an aryldiyl, virtually any group can be used to substitute Z or $Z^1$. Typical substituents include, but are not limited to, —X, —R, =O, —OR, —SR, =S, —NRR, =NR, —$CX_3$, —CN, —OCN, —SCN, —NCO, —NCS, —NO, —$NO_2$, =$N_2$, —$N_3$, —S(O)$_2$O⁻, —S(O)$_2$OH, —S(O)$_2$R, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F or —Cl) and each R is independently hydrogen, ($C_1$-$C_6$) alkyl, 2-6 membered heteroalkyl, ($C_5$-$C_{14}$) aryl or heteroaryl. The R groups may be further substituted with one or more of the same or different substituents, which are typically selected from the group consisting of —X, —R', =O, —OR', —SR', =S, —NR'R', =NR', —$CX_3$, —CN, —OCN, —SCN, —NCO, —NCS, —NO, —$NO_2$, =$N_2$, —$N_3$, —S(O)$_2$O⁻, —S(O)$_2$OH, —S(O)$_2$R', —C(O)R', —C(O)X, —C(S)R', —C(S)X, —C(O)OR', —C(O)O⁻, —C(S)OR', —C(O)SR', —C(S)SR', —C(O)NR'R', —C(S)NRR' and —C(NR)NR'R', where each X is independently a halogen (preferably —F or —Cl) and each R' is independently hydrogen, ($C_1$-$C_6$) alkyl, 2-6 membered heteroalkyl, ($C_5$-$C_{14}$) aryl or heteroaryl.

However, referring to Scheme (I), it has been observed that the displacement reaction does not proceed efficiently with arylthio and heteroarylthio compounds 108 that are substituted at the aromatic ring atoms with halogen groups. Thus, when Z is an aryl or heteroaryl and/or Z' is an aryldiyl or heteroaryldiyl, the aromatic ring atoms should not be substituted directly with halogens. However, as described above for the pyridinium ring carbon substituents, the halogens can be included in a substituent (e.g., a haloalkyl), so long as the substituent is not electronegative to disrupt the displacement reaction. Thus, with the exception of halogen, groups to substitute aryl, heteroaryl, aryldiyl and heteroaryldiyl Z and $Z^1$ groups are typically any of the groups described above for when Z is an alkyl or $Z^1$ is an alkyldiyl.

The rhodamine dyes of the invention will now be more fully described by reference to various preferred embodiments. In one preferred embodiment, the rhodamine dyes of the invention are compounds according to structural formulae (I), (Ia) and (Ib) in which each Pyr⁺ is the same and has the structure:

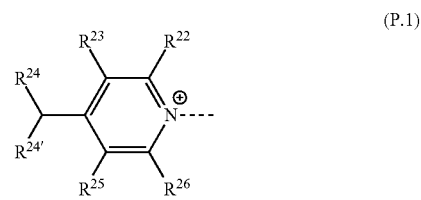

(P.1)

including any associated counter ions, wherein:
$R^{22}$ is selected from the group consisting of hydrogen and ($C_1$-$C_6$) alkyl;
$R^{23}$ is selected from the group consisting of hydrogen and ($C_1$-$C_6$) alkyl;
$R^{24}$, when taken alone, is selected from the group consisting of ($C_1$-$C_6$) alkyl, or when taken together with $R^{26}$ is ($C_4$-$C_{10}$) alkyldiyl, ($C_4$-$C_6$) alkyleno, heteroalkyldiyl or heteroalkyleno;
$R^{24'}$, when taken alone, is selected from the group consisting of ($C_1$-$C_6$) alkyl, or when taken together with $R^{24}$ is ($C_4$-$C_{10}$) alkyldiyl, ($C_4$-$C_6$) alkyleno, heteroalkyldiyl or heteroalkyleno;
$R^{25}$ is selected from the group consisting of hydrogen and ($C_1$-$C_6$) alkyl; and
$R^{26}$ is selected from the group consisting of hydrogen and ($C_1$-$C_6$) alkyl.

In the Pyr⁺ substituents of structural formula (P.1), the dashed line at the pyridinium ring nitrogen indicates the point of attachment to the phenyl ring in the compounds of structural formulae (I), (Ia) and/or (D). Preferred Pyr⁺ substituents according to structural formula (P.1) are those in which $R^{22}$, $R^{23}$, $R^{25}$ and $R^{26}$ are each hydrogen and/or in which $R^{24}$ and $R^{24'}$, when taken alone, are each the same ($C_1$-$C_6$) alkyl or, when taken together are a 4-6 membered heteroalkyleno having a single oxygen heteroatom. Particularly preferred Pyr⁺ substituents according to structural formula (P.1) are 4-(dimethylamino)pyridinium and 4-(morpholino)pyridinium.

In another preferred embodiment, the rhodamine dyes of the invention are compounds according to structural formulae (I) and (Ib) in which Z is selected from the group consisting of ($C_1$-$C_{12}$) alkyl, ($C_1$-$C_{12}$) alkyl substituted with one or more of the same or different $W^1$ groups; ($C_5$-$C_{14}$) aryl, ($C_5$-$C_{14}$) aryl substituted with one or more of the same or different $W^2$ groups, 5-14 membered heteroaryl or heteroaryl independently substituted with one or more of the same or different $W^2$ groups, wherein:
each $W^1$ is independently selected from the group consisting of —X, —R, =O, —OR, —SR, =S, —NRR, =NR, —$CX_3$, —CN, —OCN, —SCN, —NCO, —NCS, —NO, —$NO_2$, =$N_2$, —$N_3$, —S(O)$_2$O⁻, —S(O)$_2$OH, —S(O)$_2$R, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F or —Cl) and each R is independently hydrogen or $(C_1-C_6)$ alkyl; and each $W^2$ is independently selected from the group consisting of —R, —OR, —SR, —NRR, —$CX_3$, —CN, —OCN, —SCN, —NCO, —NCS, —NO, —$NO_2$, —$N_3$, —$S(O)_2O^-$—, —$S(O)_2OH$, —$S(O)_2R$, —C(O)R, —C(O)X, —C(S)R, —C(S)X, —C(O)OR, —$C(O)O^-$, —C(S)OR, —C(O)SR, —C(S)SR, —C(O)NRR, —C(S)NRR and —C(NR)NRR, R is as previously defined for $W^1$.

Preferably, Z is unsubstituted. However, when Z is a substituted $(C_5-C_{14})$ aryl or a substituted heteroaryl, the most preferred substituents are those that are not electron-withdrawing. The most preferred heteroaryl groups, whether substituted or unsubstituted, are those in which any heteroatoms are nitrogens. Especially preferred amongst these preferred heteroaryls are pyridinyl and purinyl. The most preferred aryl groups, whether substituted or unsubstituted are phenyl and naphthyl.

In another preferred embodiment, the rhodamine dyes of the invention are compounds according to structural formula (Ia) in which $Z^1$ is selected from the group consisting of $(C_1-C_{12})$ alkyldiyl, $(C_1-C_{12})$ alkyldiyl substituted with one or more of the same or different $W^1$ groups; $(C_5-C_{14})$ aryldiyl, $(C_5-C_{14})$ aryldiyl substituted with one or more of the same or different $W^2$ groups, 5-14 membered heteroaryldiyl or heteroaryldiyl independently substituted with one or more of the same or different $W^2$ groups, wherein $W^1$ and $W^2$ are as defined above.

Preferably, $Z^1$ is unsubstituted. However, when $Z^1$ is a substituted $(C_5-C_{14})$ aryldiyl or a substituted heteroaryldiyl, the most preferred substituents are those that are not electron-withdrawing. The most preferred heteroaryldiyl groups, whether substituted or unsubstituted, are those in which any heteroatoms are nitrogens. Especially preferred amongst these preferred heteroaryldiyls are pyridindiyl and purindiyl. The most preferred aryldiyl groups, whether substituted or unsubstituted are phendiyl and naphthadiyl, especially phena-1,3-diyl, phena-1,4-diyl, naphtha-2,6-diyl and naphtha-2,7-diyl.

In yet another preferred embodiment, the rhodamine dyes of the invention are compounds according to structural formula (Ia) in which rhodamine-type parent xanthene ring is a compound according to structural formula (Y-1):

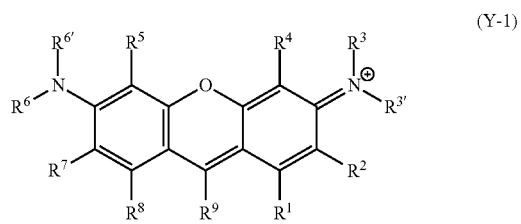

(Y-1)

including any associated counterions, wherein:
$R^1$ and $R^2$ are each independently selected from the group consisting of hydrogen and $(C_1-C_6)$ alkyl;
$R^3$, when taken alone, is selected from the group consisting of hydrogen, $(C_1-C_6)$ alkyl, $(C_5-C_{14})$ aryl and $(C_5-C_{14})$ arylaryl, or when taken together with $R^{3'}$ is $(C_4-C_6)$ alkyldiyl or $(C_4-C_6)$ alkyleno, or when taken together with $R^2$ or $R^4$ is $(C_2-C_6)$ alkyldiyl or $(C_2-C_6)$ alkyleno;
$R^{3'}$, when taken alone, is selected from the group consisting of hydrogen, $(C_1-C_6)$ alkyl, $(C_5-C_{14})$ aryl and $(C_5-C_{14})$ arylaryl, or when taken together with $R^3$ is $(C_4-C_6)$ alkyldiyl or $(C_4-C_6)$ alkyleno, or when taken together with $R^2$ or $R^4$ is $(C_2-C_6)$ alkyldiyl or $(C_2-C_6)$ alkyleno;

$R^4$, when taken alone, is selected from the group consisting of hydrogen and $(C_1-C_6)$ alkyl, or when taken together with $R^3$ or $R^{3'}$ is $(C_2-C_6)$ alkyldiyl or $(C_2-C_6)$ alkyleno;

$R^5$, when taken alone, is selected from the group consisting of hydrogen and $(C_1-C_6)$ alkyl, or when taken together with $R^6$ or $R^{6'}$ is $(C_2-C_6)$ alkyldiyl or $(C_2-C_6)$ alkyleno;

$R^6$, when taken alone, is selected from the group consisting of hydrogen, $(C_1-C_6)$ alkyl, $(C_5-C_{14})$ aryl and $(C_5-C_{14})$ arylaryl, or when taken together with $R^{6'}$ is $(C_4-C_6)$ alkyldiyl or $(C_4-C_6)$ alkyleno, or when taken together with $R^5$ or $R^7$ is $(C_2-C_6)$ alkyldiyl or $(C_2-C_6)$ alkyleno;

$R^{6'}$, when taken alone, is selected from the group consisting of hydrogen, $(C_1-C_6)$ alkyl, $(C_5-C_{14})$ aryl and $(C_5-C_{14})$ arylaryl, or when taken together with $R^6$ is $(C_4-C_6)$ alkyldiyl or $(C_4-C_6)$ alkyleno, or when taken together with $R^5$ or $R^7$ is $(C_2-C_6)$ alkyldiyl or $(C_2-C_6)$ alkyleno;

$R^7$, when taken alone, is selected from the group consisting of hydrogen and $(C_1-C_6)$ alkyl, or when taken together with $R^6$ or $R^{6'}$ is $(C_2-C_6)$ alkyldiyl or $(C_2-C_6)$ alkyleno;

$R^8$, when taken alone, is selected from the group consisting of hydrogen and $(C_1-C_6)$ alkyl; and $R^9$ indicates the point of attachment to phenyl bottom ring.

In another preferred embodiment, the rhodamine dyes of the invention are compounds according to structural formula (Ia) in which rhodamine-type parent xanthene ring is a compound according to structural formula (Y-2), (Y-3) or (Y-4):

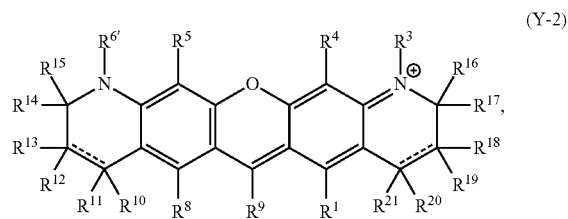

(Y-2)

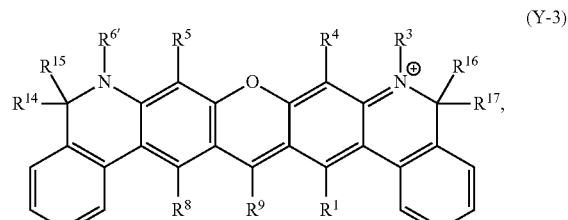

(Y-3)

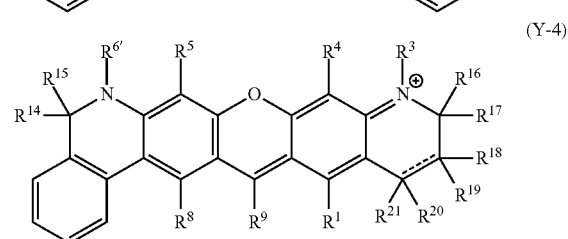

(Y-4)

including any associated counterions, wherein:
$R^1$, $R^3$, $R^4$, $R^5$, $R^{6'}$, $R^8$ and $R^9$ are as previously defined for structural formula (Y-1); and
$R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are each independently selected from the group consisting of hydrogen and $(C_1-C_6)$ alkyl, or $R^{10}$, $R^{11}$, $R^{12}$ and $R^{13}$ taken together are $(C_5-C_{14})$ aryleno or $(C_5-C_{14})$ aryleno substituted with one or more of the same or different $(C_1-C_6)$ alkyl, or $R^{18}$, $R^{19}$, $R^{20}$ and $R^{21}$ taken together are $(C_5-C_{14})$ aryleno or $(C_5-C_{14})$ aryleno substituted with one or more of the same or different $(C_1-C_6)$ alkyl.

The dashed bonds in structural formulae (Y-2) and (Y-4) indicate bonds which can each, independently of one another, be a single or a double bond. When these bonds are double bonds, one of $R^{10}$ or $R^{11}$ and one of $R^{12}$ or $R^{13}$ are taken together to form a bond and one of $R^{18}$ or $R^{19}$ and one of $R^{20}$ or $R^{21}$ are taken together to form a bond. When these bond are single bonds, the $R^{10}$, $R^{11}$, $R^{12}$, $R^{13}$, $R^{18}$, $R^{19}$, $R^{20}$ and $R^{21}$ substituents are as defined above.

In still another preferred embodiment, the rhodamine dyes of the invention are compounds according to structural formula (Ib) in which rhodamine-type parent xanthene ring Y is selected from the group consisting of (Y-1), (Y-2), (Y-3) and (Y-4), where $R^1$, $R^2$, $R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are as previously defined, and either $R^{3'}$ or $R^4$ indicates the point of attachment of substituent L. When substituent L is attached to $R^{3'}$, $R^4$ is as previously defined. When substitutent L is attached to $R^4$, $R^{3'}$ is as previously defined.

In still another preferred embodiment, the rhodamine dyes of the invention are compounds according to structural formulae (Ia) and (Ib) in which Y is selected from the group consisting of (Y-1), (Y-2), (Y-3) and (Y-4), and further in which:
- any alkyl groups are alkanyls selected from the group consisting of methanyl, ethanyl and propanyl;
- any aryl groups are phenyl or naphthyl;
- any arylaryl groups are biphenyl;
- any alkyldiyl or alkyleno bridges formed by taking $R^2$ together with $R^3$ or $R^{3'}$ are alkanyldiyls or alkanos, especially those selected from the group consisting of ethano, propano, 1,1-dimethylethano, 1,1-dimethylpropano and 1,1,3-trimethylpropano;
- any alkyldiyl or alkyleno bridges formed by taking $R^3$ together with $R^{3'}$ are alkanyldiyl or alcano, especially butano;
- any alkyldiyl or alkyleno bridges formed by taking $R^4$ together with and $R^3$ or $R^{3'}$ are alkanyldiyls or alkanos, especially those selected from the group consisting of ethano, propano, 1,1-dimethylethano, 1,1-dimethylpropano and 1,1,3-trimethylpropano;
- any alkyldiyl or alkyleno bridges formed by taking $R^5$ together with $R^6$ or $R^{6'}$ are alkanyldiyls or alkanos, especially those selected from the group consisting of ethano, propano, 1,1-dimethylethano, 1,1-dimethylpropano and 1,1,3-trimethylpropano;
- any alkyldiyl or alkyleno bridges formed by taking $R^6$ together with $R^{6'}$ are alkanyldiyl or alkano, especially butano;
- any alkyldiyl or alkyleno bridges formed by taking $R^7$ together with $R^6$ or $R^{6'}$ are alkanyldiyls or alkanos, especially those selected from the group consisting of ethano, propano, 1,1-dimethylethano, 1,1-dimethylpropano and 1,1,3-trimethylpropano;
- any aryleno bridges formed by taking $R^{10}$, $R^{11}$, $R^{12}$ and $R^{13}$ together are benzo; and
- any aryleno bridges formed by taking $R^{18}$, $R^{19}$, $R^{20}$ and $R^{21}$ together are benzo.

In yet another preferred embodiment, the rhodamine dyes of the invention are compounds according to structural formula (Ia) in which rhodamine-type parent xanthene ring Y is selected from the following group of compounds, where $R^9$ is as previously defined for structural formula (Y-1):

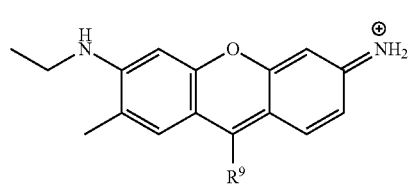
(Y-20a)

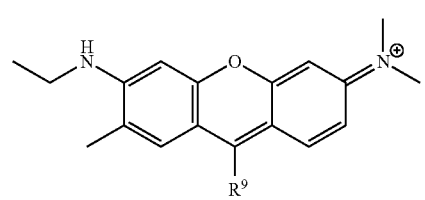
(Y-21a)

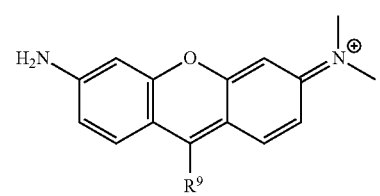
(Y-22a)

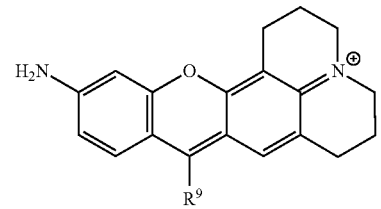
(Y-23a)

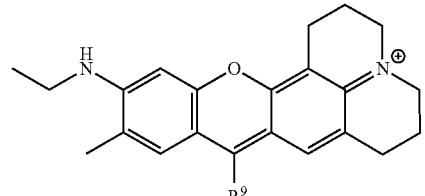
(Y-24a)

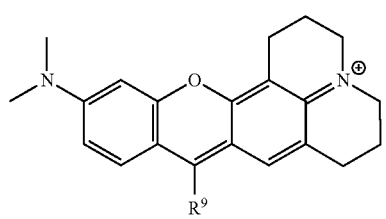
(Y-25a)

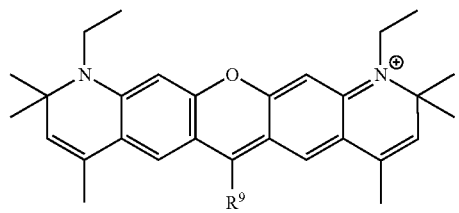
(Y-31a)

(Y-34a)
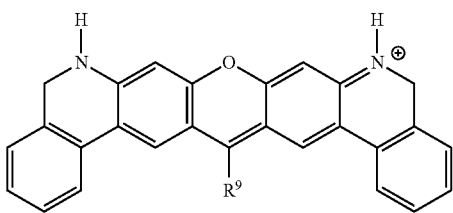

(Y-35a)
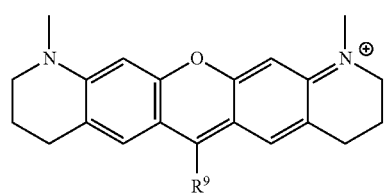

(Y-36a)
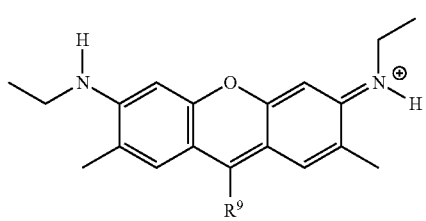

(Y-39a)
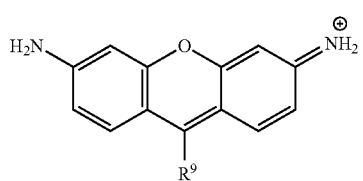

(Y-41a)
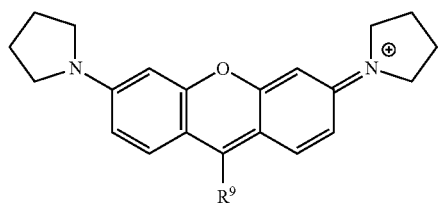

(Y-42a)
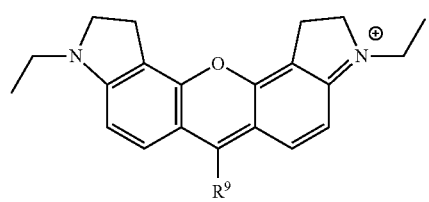

(Y-43a)
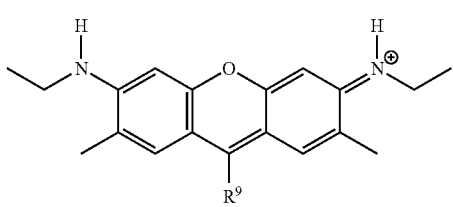

(Y-44a)
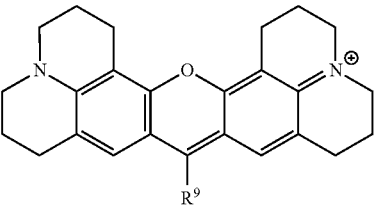

(Y-45a)
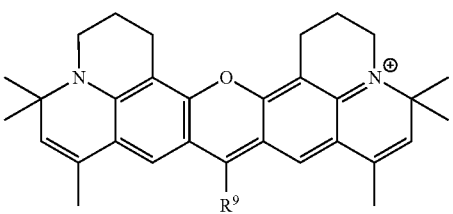

(Y-46a)
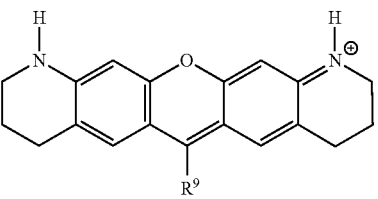

In yet another preferred embodiment, the rhodamine dyes of the invention are compounds according to structural formula (Ia) in which:

Y is selected from the group consisting of (Y-1), (Y-2), (Y-3), (Y-4), (Y-20a), (Y-21a), (Y-22a), (Y-23a), (Y-24a), (Y-25a), (Y-31a), (Y-34a), (Y-35a), (Y-36a), (Y-39a), (Y-41a), (Y-42a), (Y-43a), (Y-44a), (Y-45a), and (Y-46a);

$Z^1$ is selected from the group consisting of ($C_1$-$C_{12}$) alkyleno, ($C_1$-$C_{12}$) alkano, ($C_5$-$C_{10}$) aryldiyl, phenyldiyl, phena-1,4-diyl, naphthadiyl, naphtha-2,6-diyl and heteroaryldiyl, pyridindiyl and purindiyl.

In yet another preferred embodiment, the rhodamine dyes of the invention are compounds according to structural formula (Ia) in which:

L is a bond; and

Y is selected from the group consisting of (Y-1), (Y-2), (Y-3), (Y-4), (Y-20a), (Y-21a), (Y-22a), (Y-23a), (Y-24a), (Y-25a), (Y-31a), (Y-34a), (Y-35a), (Y-36a), (Y-39a), (Y-41a), (Y-42a), (Y-43a), (Y-44a), (Y-45a), and (Y-46a);

In still another preferred embodiment, the rhodamine dyes of the invention are compounds according to structural formula (Ia) in which:

$R_x$ is any of the electrophilic or nucleophilic groups; and

Y is selected from the group consisting of (Y-1), (Y-2), (Y-3), (Y-4), (Y-20a), (Y-21a), (Y-22a), (Y-23a), (Y-24a), (Y-25a), (Y-31a), (Y-34a), (Y-35a), (Y-36a), (Y-39a), (Y-41a), (Y-42a), (Y-43a), (Y-44a), (Y-45a), and (Y-46a);

In yet another preferred embodiment, the rhodamine dyes of the invention are compounds according to structural formula (Ib) in which Y is selected from the group consisting of (Y-1), (Y-2), (Y-3), (Y-4), (Y-20a), (Y-21a), (Y-22a), (Y-23a), (Y-24a), (Y-25a), (Y-31a), (Y-34a), (Y-35a), (Y-36a), (Y-39a), (Y-41a), (Y-43a) and (Y-46a), where substituent L is attached to the xanthene C4 carbon. In structures (Y-23a), (Y-24a) and (Y-25a), the C4 carbon in the illustrated tautomer is bridged to the xanthene nitrogen. Those of skill in the art will recognize that due to tautomerism, the carbons labeled C4 and C5 (in the definition of rhodamine-type parent xanthene ring) are essentially equivalent. Thus, in the illustrated structures of compounds (Y-23a), (Y-24a) and (Y-25a), substituent L is bonded to the C5 carbon. Particularly preferred compounds according to this aspect of the invention are those compounds in which:

Z is selected from the group consisting of ($C_1$-$C_{12}$) alkyl, ($C_1$-$C_{12}$) alkanyl, ($C_5$-$C_{10}$) aryl, phenyl, naphthyl, naphth-1-yl, naphth-2-yl, pyridyl and purinyl; and/or L is selected from the group consisting of ($C_1$-$C_6$) alkyldiyl, ($C_1$-$C_6$) alkano, ($C_5$-$C_{20}$) aryldiyl, phenyldiyl, phena-1,4-diyl, naphthyldiyl, naphtha-2,6-diyl, naphtha-2,7-diyl, ($C_6$-$C_{26}$) arylalkyldiyl-$(CH_2)_i$-φ-, —$(CH_2)_i$-Ψ-, —$(CH_2)_i$—NHR"—C(O)-φ- and —$(CH_2)_i$—NHR"—C(O)-Ψ-, where each i is independently an integer from 1 to 6, R" is hydrogen or ($C_1$-$C_6$) alkyl, φ is ($C_5$-$C_{20}$) aryldiyl, phenyldiyl or phena-1,4-diyl and Ψ is naphthyldiyl, naphtha-2,6-diyl or naphtha-2,7-diyl; and/or $R_x$ is any electrophilic or nucleophilic group.

In yet another preferred embodiment, the rhodamine dyes of the invention are compounds according to structural formula (Ib) in which Y is selected from the group consisting of (Y-1), (Y-2), (Y-3), (Y-4), where substituent L is attached to $R^3$, or one of the following group of compounds, where $R^9$ is as previously defined for structural formula (Y-1) and the dashed line at the nitrogen atom indicates the point of attachment of substituent L:

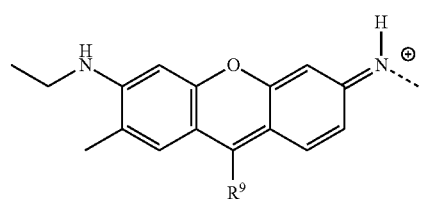

(Y-20b)

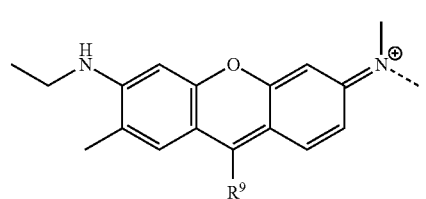

(Y-21b)

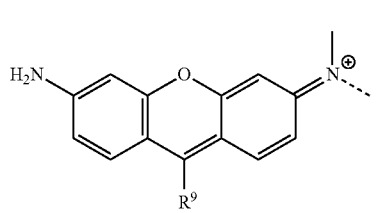

(Y-22b)

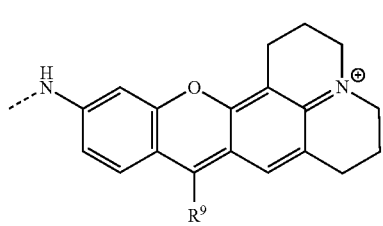

(Y-23b)

-continued

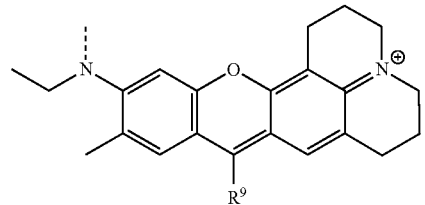

(Y-24b)

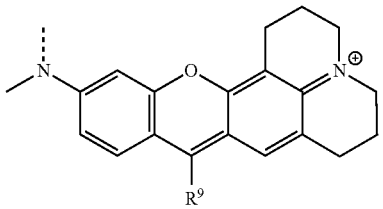

(Y-25b)

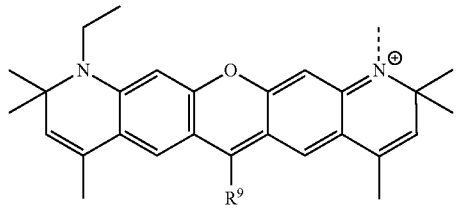

(Y-31b)

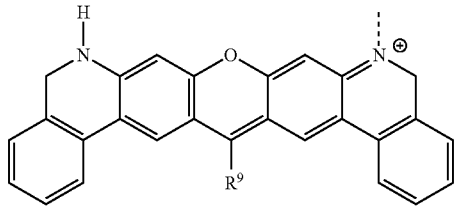

(Y-34b)

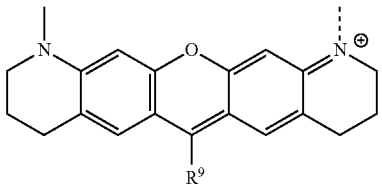

(Y-35b)

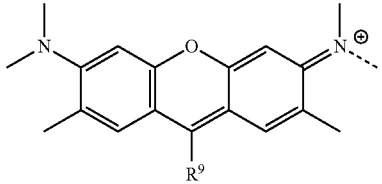

(Y-36b)

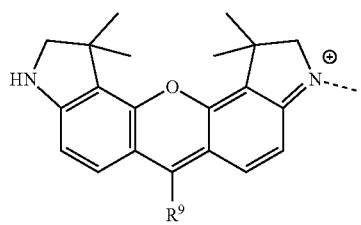

(Y-37b)

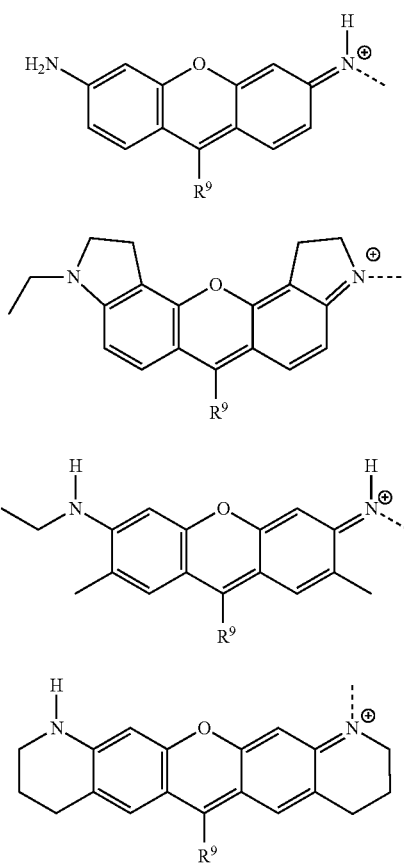

(Y-39b)

(Y-42b)

(Y-43b)

(Y-46b)

In still another preferred embodiment, the rhodamine dyes of the invention are compounds according to structural formula (Ib) in which:

Y is selected from the group consisting of (Y-1), (Y-2), (Y-3), (Y-4), (Y-20b), (Y-21b), (Y-22b), (Y-23b), (Y-24b), (Y-25b), (Y-31b), (Y-34b), (Y-35b), (Y-36b), (Y-39b), (Y-42b), (Y-43b), and (Y-46b); and Z is selected from the group consisting of ($C_1$-$C_{12}$) alkyl, ($C_1$-$C_{12}$) alkanyl, ($C_5$-$C_{10}$) aryl, phenyl, naphthyl, naphth-1-yl, naphth-2-yl, pyridyl and purinyl, where in structures (Y-1) through (Y-4) L is attached to $R^{3'}$.

L is selected from the group consisting of ($C_1$-$C_6$) alkyldiyl, ($C_1$-$C_6$) alkano, ($C_5$-$C_{20}$) aryldiyl, phenyldiyl, phena-1,4-diyl, naphthyldiyl, naphtha-2,6-diyl, naphtha-2,7-diyl, ($C_6$-$C_{26}$) arylalkyldiyl —($CH_2$)$_i$-φ-, —($CH_2$)$_i$-Ψ-, —($CH_2$)$_i$—NR''—C(O)-φ- and —($CH_2$)$_i$—NR''—C(O)-Ψ-, where each i is independently an integer from 1 to 6, R'' is hydrogen or ($C_1$-$C_6$) alkyl, φ is ($C_5$-$C_{20}$) aryldiyl, phenyldiyl or phena-1,4-diyl and Ψ is naphthyldiyl, naphtha-2,6-diyl or naphtha-2,7-diyl, and where in structures (Y-1) through (Y-4), L is attached to $R^{3'}$.

$R_x$ is any electrophilic or nucleophilic group.

In still another preferred embodiment, the rhodamine dyes of the invention are compounds according to structural formulae (I), (Ia) and (Ib), including any of their respective previously-described preferred embodiments, in which E is a carboxyl or a salt thereof.

In the rhodamine dyes of the invention, aside from substituent E, the exact positions of the various substituents substituting the new bottom ring, i.e., the $Pyr^+$ and —S—$Z^1$-L-$R_x$ substituents illustrated in structural formula (Ia) and the $Pyr^+$ and —S—Z substituents illustrated in structural formula (Ib) in the dyes of the present invention may be unknown. However, it has been confirmed by nuclear magnetic resonance (NMR) that the bottom ring contains one, two, or three $Pyr^+$ substituents. Based upon the starting materials used to synthesize the rhodamine dyes of the invention and the nature of the synthesis reactions (discussed in more detail in Section 5.3.2, infra), it is believed that the various rhodamine dyes according to structural formula (I) have the regiochemistry depicted in structural formula (Ic) (illustrated with $Pyr^+$=4-(dimethylamino)pyridinium and E=—$CO_2$H):

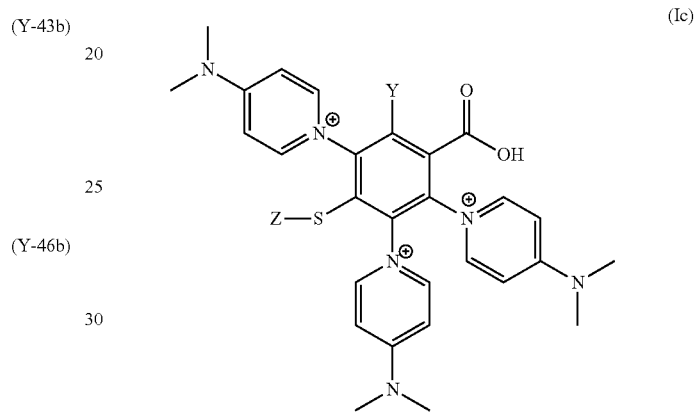

(Ic)

It will be understood, however, that the Applicants do not intend to be bound by any particular structural representation, and that the invention is intended to encompass the rhodamine dyes that are obtained by the synthetic methods described herein, regardless of their specific regiochemistry.

In addition to the above-described structural isomerism about the new bottom ring, those of skill in the art will appreciate that many of the compounds encompassed by formulae (I), (Ia) and/or (Ib) as described herein, as well as many of the energy-transfer dye pairs and other conjugates described infra, may exhibit the phenomena of tautomerism, conformational isomerism, geometric isomerism and/or stereoisomerism. As the formulae drawings within this specification can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein.

Moreover, as the compounds of the invention may bear one or more positive charges or negative charges, depending upon their physical state, they may be in the form of a salts or may have counterions associated therewith. The identity(ies) of any associated counterions is typically dictated by the synthesis and/or isolation methods by which the compounds are obtained. Typical counterions include, but are not limited to, halides, acetate, trifluoroacetate, etc. and mixtures thereof. It will be understood that the identity(ies) of any associated counterions is not a critical feature of the invention, and that the invention encompasses any type of associated counterion.

Moreover, as the compounds can exists in a variety of different forms, the invention is intended to encompass not only forms that are in association with counterions (e.g., dry salts), but also forms that are not in association with counterions (e.g., aqueous solutions).

5.3.2 Methods of Synthesis

The rhodamine dyes of the invention, and in particular rhodamine dyes according to structural formula (Ia) in which each Pyr⁺ is 4-(dimethylamino)pyridinium can be readily synthesized from corresponding tetrafluoro-rhodamine starting materials according to Scheme I, below. Although a specific regiochemistry is depicted in Scheme I, it will be understood that the structural representations are illustrative only. In Scheme I, Y, S, L, $Z^1$ and $R_x$ are as previously defined for structural formula (Ia). E is illustratively a carboxyl, but could be a sulfonate.

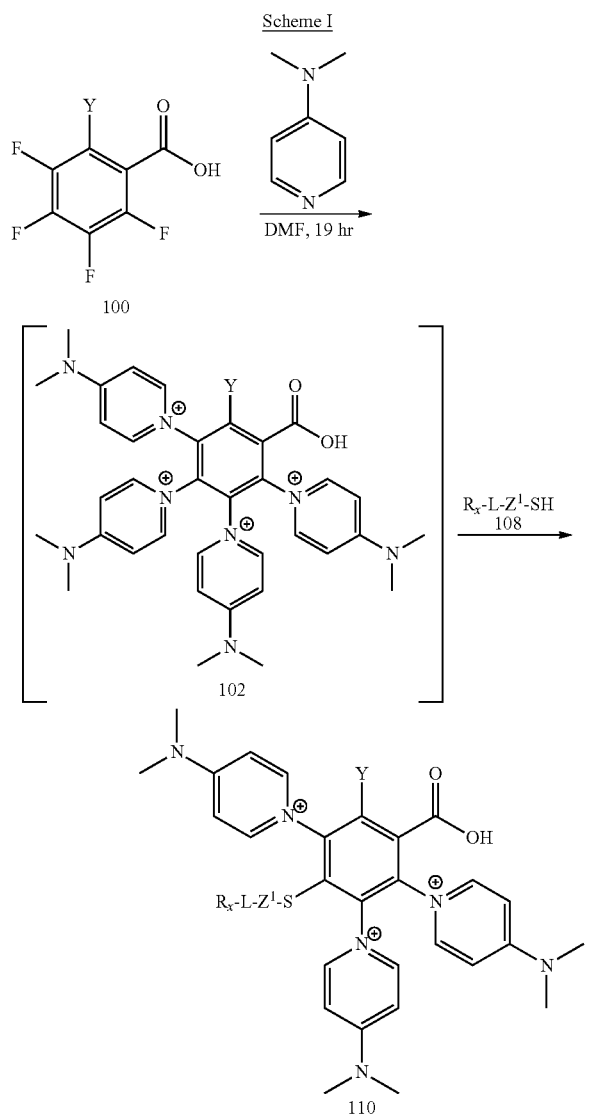

Referring to Scheme I, 4-(dimethyl)aminopyridine is added to a solution of tetrafluoro-rhodamine 100. The reaction is followed by thin-layer chromatography (TLC). The compound will depend upon the identity of rhodamine-type parent xanthene ring Y. Once the reaction has gone to completion, thiol 108 is added to the mixture and the reaction monitored with TLC. Dye 110 is purified by reverse phase chromatography or other standard methods. Compounds in which Pyr⁺ is other than 4-(dimethylamino)pyridinium are prepared in an analogous manner from the appropriate aminopyridine starting material. Compounds having non-identical Pyr⁺ groups may be prepared using a mixture of the appropriate aminopyridines.

Compounds according to structural formula (Ib) are synthesized in a similar manner from the appropriate tetrafluoro-rhodamine derivative 101 (illustrated below) using thiol Z—SH (106), where Z is as defined in structural formula (Ib), to displace a DMAP⁺ group:

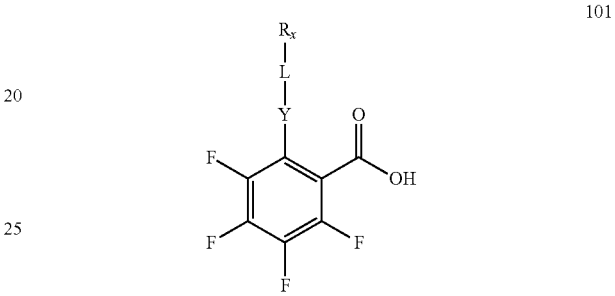

In derivative 101, Y, L and $R_x$ are as previously defined for structural formula (Ib). When linking moiety -L-$R_x$ is attached at a xanthene nitrogen, tetrafluoro-rhodamine 101 is prepared as illustrated in Scheme I. When linking moiety is attached at the xanthene C4 position, tetrafluoro-rhodamine 101 is prepared from a substituted monomer 118 ($R^4$=CH₂X or L-$R_x$). The full range of rhodamine dyes described herein can be synthesized by routine modification of these methods. Where necessary, any reactive functionalities on linker L, e.g. reactive functional group $R_x$ can be protected using known groups and methods (see, e.g., Greene & Wuts, *Protective Groups in Organic Chemistry*, 1991, 2$^{nd}$ Edition, John Wiley & Sons, NY). Dyes in which $R_x$ is a carboxylic acid or a salt thereof are particularly advantageous, as the carboxyl group does not require protection during synthesis.

The appropriate tetrafluoro-rhodamine starting materials can be produced in the usual manner for the synthesis of rhodamines by condensing 1 mol of an appropriate 3-aminophenol derivative with 1 mol of tetrafluorophthalic anhydride 114 (Aldrich Chemical Co, St. Louis, Mo.) according to known techniques (see, e.g., U.S. Pat. No. 5,750,409; Römpps' *Chemie Lexicon*, 8$^{th}$ Edition, pp. 3580). The appropriate 3-aminophenol starting materials are either commercially available or can be readily obtained using standard synthesis methods. A representative synthesis for preparing tetrafluororhodamine starting material 100 in which rhodamine-type parent xanthene ring Y is a compound according to structural formula (Y-1) (compound 120) is outlined in Scheme II.

Scheme II

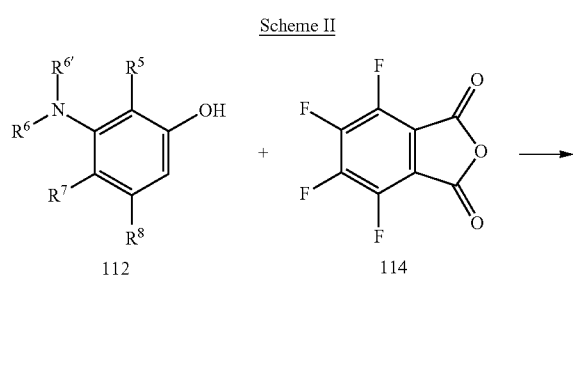

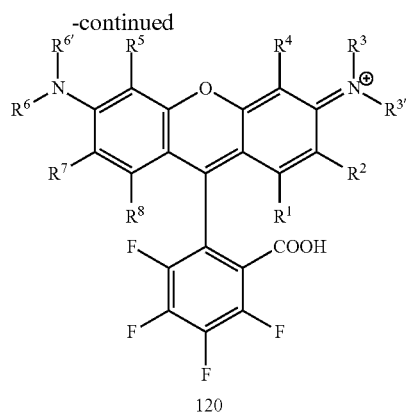

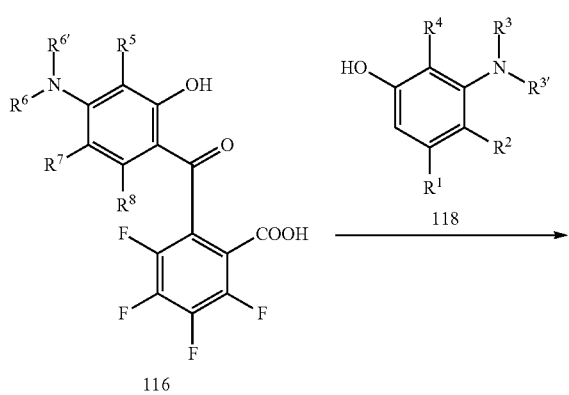

In Scheme II, the various R" substituents are as previously defined for structural formula (Y-1). According to Scheme II, 1 mol of 3-aminophenol derivative 112 is refluxed with 1 mol of tetrafluorophthalic anhydride 114 (Aldrich) to yield intermediate 116. Intermediate 116 is refluxed with 3-aminophenol derivative 118 to yield tetrafluoro-rhodamine 120. Depending upon the identity of rhodamine-type parent xanthene ring Y, the tetrafluoro-rhodamine 120 is isolated by reverse phase or normal phase column chromatography.

An analogous method for synthesizing tetrafluoro-rhodamine 100 in which rhodamine-type parent xanthene ring Y is a compound according to structural formula (Y-2) is illustrated in Scheme III:

Scheme III

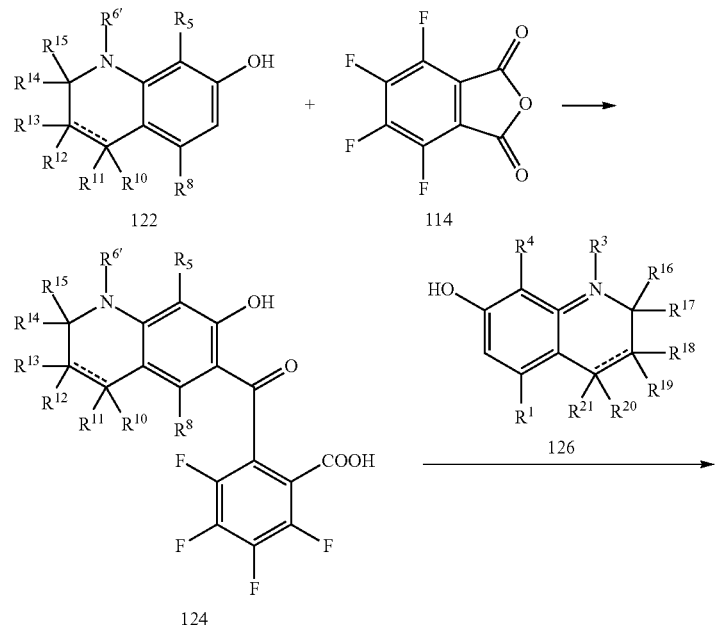

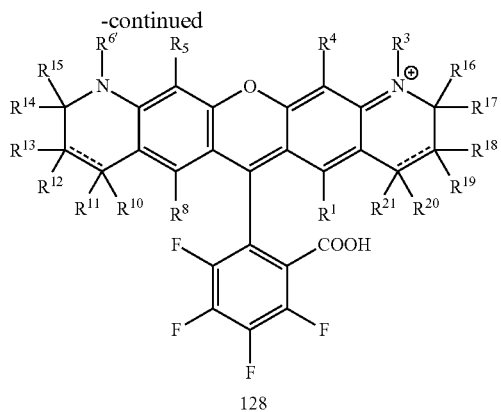

128

In Scheme III, the various R" substituents are as previously defined for structural formula (Y-2). Dyes according to structural formula (Ia) in which the rhodamine-type parent xanthene ring is a compound according to structural formula (Y-3) or (Y-4) are prepared in an analogous manner from the appropriate starting materials.

Methods of preparing tetrafluoro-rhodamine derivative 101 in which Y is a compound according to structural formula (Y-1) or (Y-2) in which the linking moiety is attached to the xanthene nitrogen (i.e., at position $R^{3'}$) are illustrated in Schemes IIb and IIIb, respectively:

Scheme (IIb)

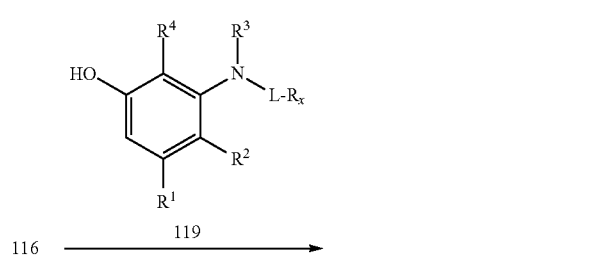

116 →119→

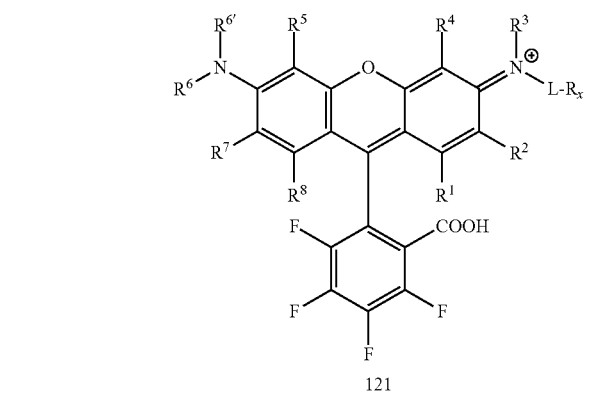

121

Scheme IIIb

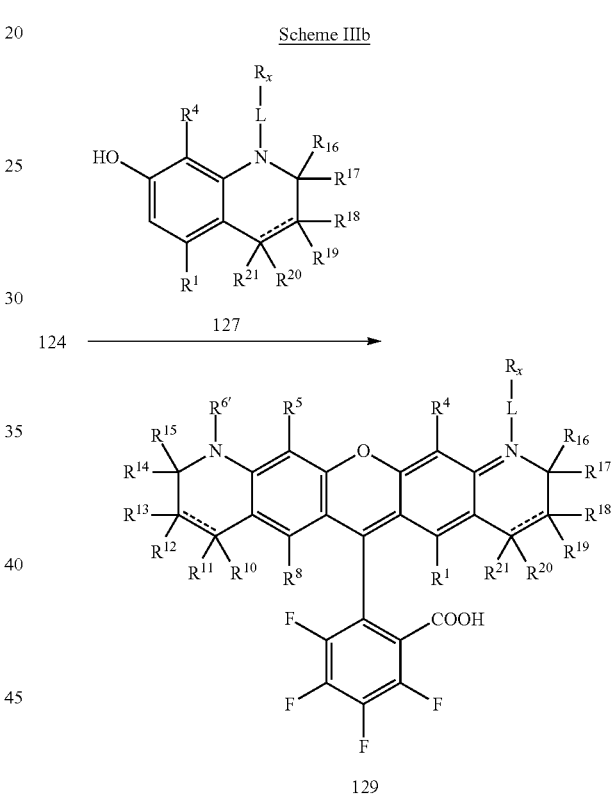

124 →127→

129

The various aminophenol starting materials are either commercially available or can be prepared using routine methods. Exemplary syntheses are provided in the Examples section. The full scope of the rhodamine compounds described herein can be readily synthesized by routine modification of any of these methods.

5.4 Energy Transfer Dye Pairs

In another aspect, the present invention provides energy-transfer dye pairs incorporating the new rhodamine dyes of the invention. Generally, the energy-transfer dye pairs of the present invention comprise three main elements: (i) a donor dye (DD) which absorbs light at a first wavelength and emits excitation energy in response; (ii) an acceptor dye (AD) which is capable of absorbing the excitation energy emitted by the donor dye and emitting light at a second wavelength in response; and (iii) a linkage linking the donor dye to the acceptor dye, the linkage being effective to facilitate efficient energy-transfer between the donor and acceptor dyes. In the energy-transfer dye pairs of the invention, at least one of the donor or acceptor dyes, typically the acceptor dye, is a new rhodamine dye of the invention. The donor and acceptor dyes can be linked together in a variety of different configurations, depending upon the identities of the dyes. A thorough discussion of the various structures, synthesis and use of certain energy-transfer dye pairs which may aid an understanding of the energy-transfer dye pairs of the invention is provided in U.S. Pat. No. 5,800,996; U.S. Pat. No. 5,863,727; and U.S. Pat. No. 5,654,419, the disclosures of which are incorporated herein by reference in their entireties.

The energy-transfer dye pairs of the invention are typically obtained as illustrated in Scheme V:

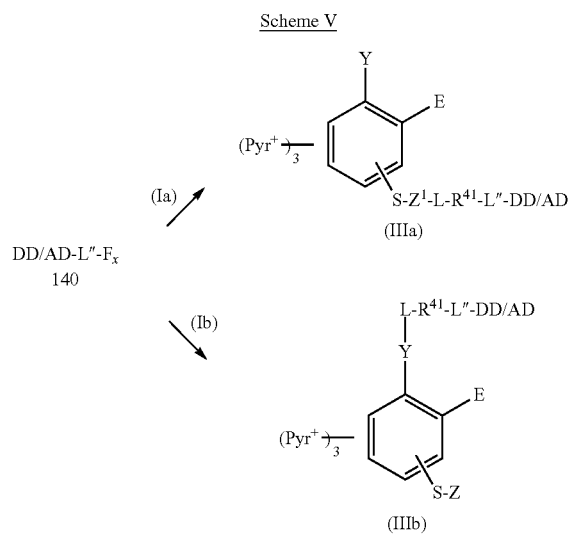

In Scheme V, a dye 140 which includes an optional linker L" and a complementary functional group $F_x$ is condensed with a rhodamine dye of the invention according to structural formula (Ia) or (Ib) to yield energy-transfer dye pairs according to structural formulae (IIa) and (IIb), respectfully, where for example three pyridinium rings are present.

During the condensation, reactive group $R_x$ and complementary functional group $F_x$ react to form covalent linkage $R^{41}$. Thus, it will be recognized by those of skill in the art that reactive group $R_x$ and complementary functional group $F_x$ can each constitute respective members of the various pairs of complementary groups described in Section 5.3.1, such as various pairs of complementary electrophiles and nucleophiles. Preferably, one of $R_x$ or $F_x$ is an amine, thiol or hydroxyl group, most preferably an amine group, and the other one of $R_x$ or $F_x$ is a group capable of reacting with an amine, thiol or hydroxyl, most preferably a carboxylic acid or a salt, ester or activated ester thereof. Thus, a particularly preferred covalent linkage $R^{41}$ is an amide of the formula —C(O)NR$^{45}$—, where R$^{45}$ is hydrogen or ($C_1$-$C_6$) alkyl.

In the energy-transfer dye pairs according to structural formulae (IIa) and (IIb), DD/AD represents either a donor dye or an acceptor dye. Whether DD/AD constitutes a donor or acceptor will depend on the respective excitation and emission properties of DD/AD and Y. Typically, DD/AD is a dye belonging to the xanthene (including fluorescein and rhodamine dyes), cyanine, phthalocyanine or squaraine classes of dyes. Alternatively, DD/AD can be a dye of the invention, preferably a dye according to structural formula (Ia) or (Ib). The only requirement is that dye DD/AD either be capable of absorbing excitation energy emitted from Y or be capable of emitting excitation energy absorbable by Y. Preferably, in addition to complementary functional group $F_x$, DD/AD includes a linking moiety or linking group as previously described for conjugating the energy-transfer dye pairs of the invention to other compounds or substances. L" represents a bond or a linker analogous to the previously described linkers L that, when included in an energy-transfer dye pair according to structural formula (IIa) or (IIb), facilitates efficient energy transfer between the acceptor and donor chromophores. The identity of L" and its point of attachment to DD/AD will depend, in part, upon the identity of DD/AD. Structures of these various classes of AD/DD dyes, as well as suitable linkers L" and points of attachment to these various classes of AD/DD dyes are described in U.S. Pat. No. 5,863,727, the disclosure of which is incorporated herein by reference. When DD/AD is a cyanine dye, L" is preferably an amide, and is attached to the quaternary nitrogen. When DD/AD is a phthalocyanine dye, L" is preferably a sulfonamide, and is attached to the aromatic carbon skeleton. When DD/AD is a squaraine dye, L" is preferably an amide, and is attached to the quaternary nitrogen. When DD/AD is a rhodamine dye, L" is preferably an amide, and is attached to C4 or R$^9$. When DD/AD is a fluorescein dye, U is preferably an amide, and is attached to C4 or R$^9$.

Most preferably, DD/AD is a donor dye which emits excitation energy absorbable by Y. Preferred donor dyes are xanthene dyes, especially those which include a linking moiety or linking group on their bottom rings. Preferred amongst the xanthene dyes are the fluorescein dyes. Fluorescein dyes suitable for use as donor dyes include, but are not limited to, the 4,7-dichlorofluoresceins described in U.S. Pat. No. 5,188,934, the extended fluoresceins described in U.S. Pat. No. 5,775,409, 5-carboxyfluorescein (5-FAM), 6-carboxyfluorescein (6-FAM), 5-(and 6)-carboxyfluorescein (5,6-FAM), NAN, Cl-FLAN and TET. Linker L" is typically attached to the xanthene C4 position of these preferred fluorescein donor dye. The actual choice of donor dye will depend upon the emission and excitation properties of DA/AD and Y, and will be apparent to those of skill in the art. In preferred fluorescein donor dyes that include a 5-, 6- or 5-(and 6)-carboxyl, the carboxyl group (or an activated ester thereof) can be used to covalently conjugate the energy-transfer dye pairs of the invention to other compounds or substances.

The energy-transfer dyes of the invention are more fully described below with reference to Various preferred embodiments. Referring to Scheme V, one group of preferred energy-transfer dye pairs according to structural formulae (IIa) and (IIb) are obtained when the compounds according to structural formulae (Ia) and (Ib) are any of their previously-described preferred embodiments and compound 140 has the structure:

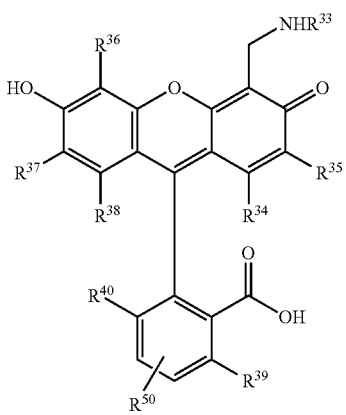

including any counter ions, wherein:
$R^{33}$ is hydrogen a

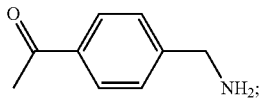

$R^{34}$, when taken alone, is hydrogen, or when taken together with $R^{35}$ is benzo;
$R^{35}$, when taken alone, is hydrogen, fluoro, chloro, hydroxyl or carboxyl, or when taken together with $R^{34}$ is benzo;
$R^{36}$ is hydrogen, fluoro or chloro;
$R^{37}$, when taken alone, is hydrogen, fluoro, chloro, hydroxyl or carboxyl, or when taken together with $R^{38}$ is benzo;
$R^{38}$, when taken alone, is hydrogen, or when taken together with $R^{37}$ is Benzo;
$R^{39}$ is hydrogen or chloro;
$R^{40}$ is hydrogen or chloro; and
$R^{50}$ is carboxyl, or a salt, ester or activated ester thereof. Preferred compound 140 can be the pure 5-isomer, the pure 6-isomer or a mixture of 5-(and 6)-isomers. Particularly preferred compounds 140 are those in which $R^{34}$, $R^{35}$, $R^{36}$, $R^{37}$, $R^{38}$, $R^{39}$ and $R^{40}$ are each hydrogen.

In another preferred embodiment, the energy-transfer dye pairs of the invention are compounds according to structural formula (IIa) in which:
Y is a compound according to structural formula (Y-1), (Y-2), (Y-3), (Y-4), (Y-20a), (Y-21a), (Y-22a), (Y-23a), (Y-24a), (Y-25a), (Y-31a), (Y-34a), (Y-35a), (Y-36a), (Y-39a), (Y-41a), (Y-42a), (Y-43a), (Y-44a), (Y-45a), or (Y-46a);
DD/AD is a fluorescein dye having a 5- or 6-carboxyl group or a salt, ester or activated ester thereof, particularly a fluorescein dye selected from the group consisting of 5-carboxyfluorescein (5-FAM), 6-carboxyfluorescein (6-FAM), 5-(and -6)-carboxyfluorescein, NAN, Cl-FLAN and TET;
L is a bond, $(C_1-C_6)$ alkyldiyl or $(C_1-C_3)$ alkano, preferably a bond;
$Z^1$ is $(C_1-C_6)$alkyldiyl, $(C_5-C_{14})$aryl or heteroaryl;
$R^{41}$ is —C(O)—$R^{42}$—, where $R^2$ is O, S or NH and is bonded to L"; and/or
L" is —$R^{41}$—$Z^3$—C(O)—$R^{44}$—$R^{45}$—, wherein $R^{43}$ is $(C_1-C_6)$ alkyldiyl, preferably $(C_1-C_3)$ alkano, and is bonded to $R^{42}$; $Z^3$ is 5-6 membered cyclic alkenyldiyl or heteroalkenyldiyl, $(C_5-C_{14})$ aryldiyl or heteroaryldiyl; $R^{44}$ is O, S or NH; and $R^{45}$ is $(C_1-C_6)$ alkyldiyl, preferably $(C_1-C_3)$ alkano, and is bonded to the xanthene C4 carbon of DD/AD.

Particularly preferred amongst the above-described energy-transfer dye pairs are those compounds in which:
L is a bond;
$Z^1$ and $Z^3$ are each independently selected from the group consisting of phenyldiyl, phena-1,4-diyl, naphthyldiyl, naphtha-2,6-diyl and naphtha-3,6-diyl;
$R^{42}$ is NH;
$R^{43}$ is methano;
$R^{44}$ is NH; and/or
$R^{45}$ is methano.

In another preferred embodiment, the energy-transfer dye pairs of the invention are compounds according to structural formula (IIb) in which:
E is carboxyl or a salt thereof,
Y is a compound according to structural formula (Y-1), (Y-2), (Y-3) or (Y-4), where L is attached at position $R^{3'}$, or is a compound according to structural formula (Y-20b), (Y-21b), (Y-22b), (Y-23b), (Y-24b), (Y-25b), (Y-31b), (Y-34b), (Y-35b), (Y-36b), (Y-39b), (Y-41b), (Y-42b), (Y-43b), or (Y-46b);
DD/AD is a fluorescein dye having a 5- or 6-carboxyl group or a salt, an ester or an activated ester thereof, particularly a fluorescein dye selected from the group consisting of 5-carboxyfluorescein (5-FAM), 6-carboxyfluorescein (6-FAM), 5-(and -6)-carboxyfluorescein, NAN, Cl-FLAN and TET;
Z is $(C_1-C_6)$ alkyl, $(C_1-C_6)$ alkanyl, $(C_5-C_{14})$ aryl or heteroaryl;
L is or —$CH_2$-φ-, or —$CH_2$-Ψ-, where φ is phenyldiyl and Ψ is naphthyldiyl and the methylene is attached to Y;
$R^{41}$ is —C(O)—$R^{42}$—, where $R^{42}$ is O, S or NH; and/or
L" is —$R^{43}$—$Z^3$—C(O)—$R^{44}$—$R^{43}$—, wherein $R^{43}$ is $(C_1-C_6)$ alkyldiyl, preferably $(C_1-C_3)$ alkano, and is bonded to $R^{42}$; $Z^3$ is 5-6 membered cyclic alkenyldiyl or heteroalkenyldiyl, $(C_5-C_{14})$ aryldiyl or heteroaryldiyl; $R^{44}$ is O, S or NH; and $R^{45}$ is $(C_1-C_6)$ alkyldiyl, preferably $(C_1-C_3)$ alkano, and is bonded to the xanthene C4 carbon of DD/AD.

Particularly preferred amongst the above-described energy-transfer dye pairs are those compounds in which:
L is methano;
Z is selected from the group consisting of phenyl, naphthyl, naphth-1-yl and naphth-2-yl;
$Z^3$ is selected from the group consisting of phenyldiyl, phen-1,4-diyl, naphthyldiyl, naphth-2,6-diyl and naphth-3,6-diyl;
$R^{42}$ is NH;
$R^{43}$ is methano;
$R^{44}$ is NH; and/or
$R^{45}$ is methano.

5.4.1 Synthesis of the Energy-Transfer Dye Pairs

Methods for synthesizing the various energy-transfer dyes of the invention are illustrated in Scheme V, supra. Conditions for carrying out the reactions are described in U.S. Pat. No. 5,863,727, including Compound 140. Syntheses of exemplary energy-transfer dye pairs are described in the Examples section. All of the energy-transfer dye pairs of the invention can be obtained by routine modification of any of these methods.

5.5 Conjugates Incorporating Dyes and Energy-Transfer Dye Pairs

In another aspect, the present invention comprises molecules and/or substances or conjugated with the rhodamine dyes and/or energy-transfer dye pairs of the invention. The conjugates can comprise virtually any molecule or substance to which the dyes or energy-transfer dye pairs of the invention can be conjugated, including by way of example and not limitation, peptides, polypeptides, proteins, saccharides, polysaccharides, nucleosides, nucleotides, polynucleotides, lipids, solid synthesis supports, organic and inorganic polymers, and combinations and assemblages thereof, such as chromosomes, nuclei, living cells (e.g., bacteria or other microorganisms, mammalian cells, tissues, etc.), and the like. The dyes or energy-transfer dye pairs are conjugated with the reagent via a linking moiety by a variety of means, including hydrophobic attraction, ionic attraction, covalent attachment or with the aid of pairs of specific binding molecules, as previously described. Preferably, the dyes are conjugated via covalent attachment.

Conjugation typically results from mixing a dye or dye pair including an optional linking moiety with and the molecule or substance to be conjugated in a suitable solvent in which both are soluble, using methods well-known in the art, followed by separation of the conjugate from any unconjugated starting materials or unwanted by-products. The dye or dye pair conjugate can be stored dry or in solution for later use.

5.5.1 Nucleoside/Tide Conjugates

A preferred class of conjugates include nucleosides/tides and nucleoside/tide analogs that are labeled with the rhodamine dyes or energy-transfer dye pairs of the invention. Such labeled nucleosides/tides are particularly useful for labeling polynucleotides formed by enzymatic synthesis, e.g., labeled nucleotide triphosphates used in the context of template-directed primer extension, PCR amplification, Sanger-type polynucleotide sequencing, and/or nick-translation reactions. Labeled nucleoside/tides and/or nucleoside/tide analog conjugates are generally obtained by condensing a nucleoside/tide or nucleoside/tide analog (NUC) modified to contain a linking moiety (-L'-$F_x$) with a rhodamine dye according to structural formula (Ia) or (Ib) to yield a dye-labeled nucleoside/tide or nucleoside/tide analog according to structural formula (IIIa) or (IIIb), respectively. Energy-transfer dye pair-labeled nucleosides/tides and/or nucleoside/tide analogs are obtained in an similar manner with energy-transfer dye compounds according to structural formulae (IIa) and (IIb) in which the DD/AD dye includes an optional linking moiety of the formula -$L^3$-$R_x$, where is a bond or linker similar to previously-described linker L (compounds (IIa.1) and (IIb.1), respectively). These reactions are illustrated in Schemes VIa and VIb:

Scheme VIa

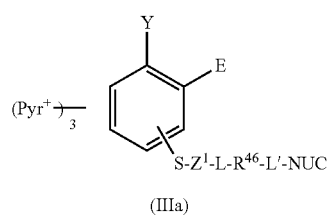

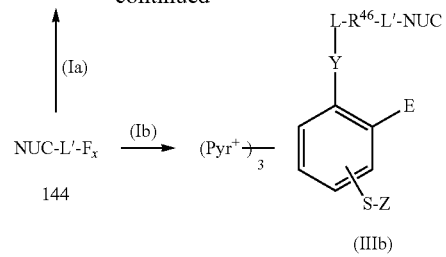

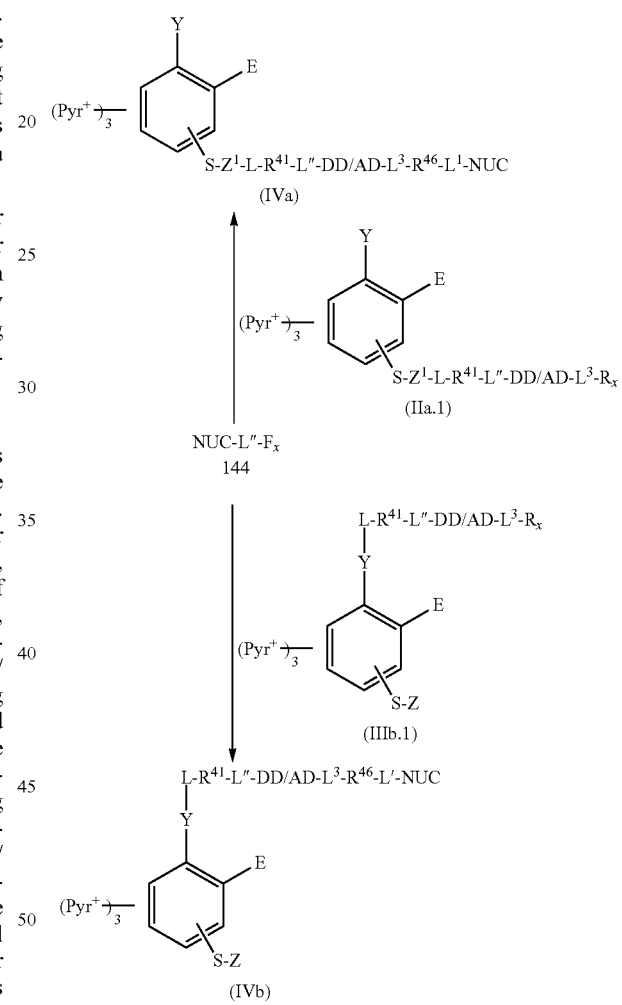

Referring to Schemes VIa and VIb, where for example three pyridinium rings are present and reactive functional group $R_x$ on dyes or energy-transfer dye pairs according to structural formulae (Ia), (Ib), (IIa.1) and/or (IIb.1) and complementary functional group $F_x$ on compound 144 react to form covalent linkage $R^{46}$. Covalent linkage $R^{46}$ is analogous to the previously-described covalent linkage $R^{41}$. Preferred embodiments of $R^{46}$ are the same as the preferred embodiments previously described for $R^{41}$.

Complementary functional group $F_x$ is attached to NUC via linker L'. Complementary functional group $F_x$ may be attached directly to NUC, in which case L' represents a bond, or it may be spaced away from NUC by one or more intervening atoms, in which case L' represents a linker. Any of the linkers L or L" previously described in connection with the rhodamine dye compounds per se and/or the energy-transfer dye pairs per se can be used for linker L'.

Complementary functional group $F_x$ may be attached to NUC at a variety of different positions, e.g., the nucleobase, the sugar and/or the phosphate ester moiety. Nucleosides/tides and nucleoside/tide analogs that are appropriately modified at these various positions such that they can be conjugated with dyes and/or dye pairs according to the invention are known in the art. Preferably, complementary group F, is attached to the nucleobase. When the nucleobase is a 7-deazapurine, L' is usually attached to the C7 position of the nucleobase. When the nucleobase is a pyrimidine, L' is usually attached to the C-5 position of the nucleobase. When the nucleobase is a purine, L' is usually attached to the C-8 position of the nucleobase. Linkers L' useful for covalently conjugating the dyes of the invention to the nucleobase of NUC are described in U.S. Pat. No. 5,821,356, U.S. Pat. No. 5,770,716 and U.S. application Ser. No. 08/833,854 filed Apr. 10, 1997, the disclosures of which are incorporated herein by reference.

Preferred linkers L' for covalently conjugating the dyes of the invention to the nucleobase of NUC include $(C_2-C_{20})$ alkylenos, heteroalkyldiyls and heteroalkylenos, especially $(C_2-C_{20})$ alkynos, $(C_2-C_{20})$ alkenos, heteroalkynos and heteroalkenos. A particularly preferred linker L' is —C≡C—CH$_2$—, where the terminal sp carbon is covalently attached to the nucleobase of NUC and the terminal methylene (sp$^3$) carbon is covalently attached to $R^{46}$ in the compounds of structural formulae (IIIa), (IIIb), (IVa) and (IVb), or to $F_x$ of compound 144.

Additional preferred linkers L' for covalently conjugating the rhodamine dyes or energy-transfer dye pairs of the invention to the nucleobase of NUC include propargylethoxy groups according to structural formula —C≡C—CH$_2$—O—CH$_2$—CH$_2$—NR$^{47}$—R$^{48}$—, wherein R$^{47}$ is hydrogen or (C$_1$-C$_6$) alkyl and R$^{48}$ is selected from the group consisting of —C(O)—(CH$_2$)$_r$—, —C(O)—CHR$^{49}$—, —C(O)—C≡C—CH$_2$— and —C(O)-φ-(CH$_2$)$_r$—, where each r is independently an integer from 1 to 5 and φ represents a C$_6$ aryldiyl or heteroaryldiyl, preferably phena-1,4-diyl

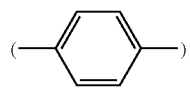

and R$^{49}$ is hydrogen, (C$_1$-C$_6$) alkyl or an amino acid side chain (including side chains of both gene-encoded and non-encoded amino acids). With these linkers L', the terminal sp carbon is attached to the nucleobase of NUC and the other terminal group is attached to R$^{46}$ in the compounds of structural formulae (IIIa), (IIIb), (IVa) and (IVb), or to $F_x$ of compound 144.

In a preferred embodiment, the labeled nucleosides/tide and/or nucleoside/tide analogs according to structural formulae (IIIa), (IIIb), (IVa) and (IVb) are labeled enzymatically-incorporatable nucleotides, labeled enzymatically extendable nucleotides or labeled terminators.

In another preferred embodiment, the labeled nucleosides/tides and nucleoside/tide analogs are those obtained from Schemes (VIa) and (VIb) in which the compounds according to structural formulae (Ia), (Ib) are any of their respective previously-defined preferred embodiments, compounds (IIa.1) and (IIb.1) are any of the previously defined preferred embodiments of compounds (IIa) and (IIb), respectively, and compound 144 is a compound according to structural formula (V):

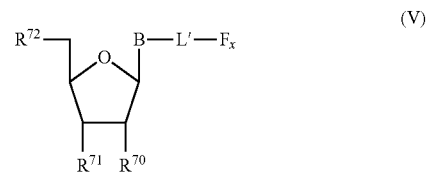

wherein:
B is a nucleobase;
$F_x$ is a complementary functional group as previously described;
L' is one of the preferred linkers described above;
$R_{70}$ and $R_{71}$, when taken alone, are each independently selected from the group consisting of hydrogen, hydroxyl and a moiety which blocks polymerase-mediated template-directed nucleic acid synthesis, or when taken together form a bond such that the illustrated sugar is 2',3'-didehydroribose; and
$R_{72}$ is selected from the group consisting of hydroxyl, a phosphate ester having the formula

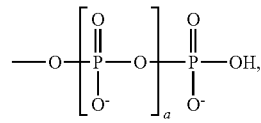

where a is an integer from 0 to 2, and a phosphate ester analog. Typically, $F_x$ is an amino group of the formula —NHR$^{51}$, where R$^{51}$ is hydrogen or (C$_1$-C$_6$)alkyl, but can be any nucleophilic or electrophilic groups.

In a preferred embodiment of structural formula (V), B is a normal nucleobase or a common analog thereof, a 7-deazapurine, 8-aza, 7-deazapurine, a purine or a pyrimidine. In a particularly preferred embodiment, B is a nucleobase selected from the group consisting of 7-deaza-adenine, cytosine, 7-deaza-guanine, thymine and uracil. When the preferred nucleobase B is a purine or a 7-deaza-purine, the pentose moiety is attached to the N$^9$-position of the nucleobase, and when the preferred B is a pyrimidine, the pentose moiety is attached to the N$^1$-position of the nucleobase. Linker L' is attached to nucleobase B as previously described.

In structural formula (V), when both $R_{70}$ and $R_{71}$ are hydroxyl, the resultant compounds produced in Schemes VIa and VIb are labeled ribonucleoside/tides. When $R_{70}$ is hydrogen and $R_{71}$ is hydroxyl, the resultant compounds are labeled 2'-deoxyribonucleoside/tides. When $R_{70}$ and $R_{71}$ are each hydrogen, the resultant compounds are 2',3'-dideoxyribonucleoside/tides. Labeled 2',3'-dideoxyribonucleoside-5'-triphosphates (ddNTPs) find particular use as terminators in Sanger-type DNA sequencing methods utilizing fluorescent detection. Labeled 2'-deoxyribonucleoside-5'-triphosphates (dNTPs) find particular use as means for labeling DNA polymerase extension products, e.g., in the polymerase chain reaction or nick-translation. Labeled ribonucleoside-5'-triphosphates (NTPs) find particular use as means for labeling RNA polymerase extension products.

Referring to Schemes (VIa) and (VIb), supra, the synthesis of alkynylamino-derivatized compounds 144 useful for conjugating the dyes of the invention to nucleosides/tides and/or nucleoside/tide analogs is taught in EP 87305844.0 and Hobbs et al., 1989, J. Org. Chem. 54:3420. The corresponding nucleoside mono-, di- and triphosphates are obtained by standard techniques (see, e.g., the methods described in U.S. Pat. No. 5,821,356, U.S. Pat. No. 5,770,716 and U.S. application Ser. No. 08/833,854 filed Apr. 10, 1997, discussed supra). Methods for synthesizing compound 144 in modified with propargylethoxyamido linkers L' can also be found in these patents and application.

Energy-transfer dye pairs can be conjugated to a nucleotide 5'-triphosphate 144 by linking through a nucleobase amino group to: (i) an activated ester of a energy-transfer dye pair, e.g. 230 NHS ester, or (ii) stepwise coupling to one dye 140, e.g. 4'-protected aminomethyl fluorescein, then coupling the unprotected 4'-aminomethyl to the second dye of the pair, e.g. 196 NHS ester.

Additional synthesis procedures suitable for use in synthesizing compounds according to structural formulae (IIIa), (IIIb), (IVa) and (IVb) are described, for example, in Gibson et al., 1987, Nucl. Acids Res. 15:6455-6467; Gebeyehu et al., 1987, Nucl. Acids Res. 15:4513-4535; Haralambidis et al., 1987, Nucl. Acids Res. 15:4856-4876; Nelson et al., 1986, Nucleosides and Nucleotides. 5(3):233-241; Bergstrom et al., 1989, J. Am. Chem. Soc. 111:374-375; U.S. Pat. No. 4,855,225, U.S. Pat. No. 5,231,191 and U.S. Pat. No. 5,449,767, the disclosures of which are incorporated herein by reference. Any of these methods can be routinely adapted or modified as necessary to synthesize the full range of labeled nucleosides/tides and nucleoside/tide analogs described herein.

5.5.1.1 Poly-nucleotide Conjugates

Yet another preferred class of conjugates of the present invention comprise polynucleotides and/or polynucleotide analogs labeled with the rhodamine dyes or energy-transfer dye pairs of the invention. Such labeled polynucleotides and/or analogs are useful in a number of important contexts, including as DNA sequencing primers, PCR primers, oligonucleotide hybridization probes, oligonucleotide ligation probes, and the like.

In one preferred embodiment, the labeled polynucleotides or polynucleotide analogs of the present invention include multiple dyes located such that fluorescence energy-transfer takes place between a donor dye and an acceptor dye. Such multi-dye-energy-transfer polynucleotides find application as spectrally-tunable sequencing primers as described, for example, in Ju et al., 1995, Proc. Natl. Acad. Sci. USA 92:4347-4351, and as hybridization probes as described, for example, in Lee et al., 1993, Nucl. Acids Res. 21:3761-3766.

Labeled polynucleotides and/or polynucleotide analogs are typically synthesized enzymatically, e.g., using a DNA/RNA polymerase or ligase (see, e.g., Stryer, 1981, *Biochemisty*, Chapter 24, W.H. Freeman and Company) and a labeled enzymatically-incorporatable nucleotide, as previously described. Alternatively, the labels may be introduced subsequent to synthesis via conventional conjugation reactions, as discussed more thoroughly below.

Generally, if the labeled polynucleotide is made using enzymatic synthesis, the following procedure may be used. A target DNA polynucleotide is denatured and an oligonucleotide primer is annealed to the target DNA. A mixture of 2'-deoxyribonucleoside-5'-triphosphates capable of supporting template-directed enzymatic extension of the primed target (e.g., a mixture including dGTP, dATP, dCTP, and dTTP) is added to the primed target. At least a fraction of the deoxynucleotides are labeled with a rhodamine dye or energy-transfer dye pair of the invention as described above. Next, a polymerase enzyme is added to the mixture under conditions where the polymerase enzyme is active. A labeled polynucleotide is formed by the incorporation of the labeled deoxynucleotides during polymerase-mediated strand synthesis. In an alternative enzymatic synthesis method, two primers are used instead of one: one complementary to the plus (+) strand of the target and another complementary to the minus (−) strand of the target, the polymerase is a thermostable polymerase and the reaction temperature is cycled between a denaturation temperature and an extension temperature, thereby exponentially synthesizing a labeled complement to the target sequence by PCR (see, e.g., *PCR Protocols*, 1990, Innis et al. Eds., Academic Press).

Alternatively, the labeled polynucleotide or polynucleotide analog is obtained via post-synthesis conjugation. According to this embodiment, a polynucleotide or polynucleotide analog which includes a complementary functional group $F_x$, typically an amino group, is condensed with a rhodamine dye according to structural formula (IIa) or (IIb) or an energy-transfer dye pair according to structural formula (IIIa) or (IIIb) under conditions wherein $R_x$ and $F_x$ react to form a covalent linkage. The labeled polynucleotides and/or polynucleotide analogs are isolated using conventional means, such as alcohol precipitation, gel electrophoresis, column chromatography, etc.

A variety of reagents for introducing amino groups, or other complementary functional groups such as thiols into enzymatically or chemically synthesized polynucleotides and polynucleotide analogs are known in the art, as are appropriate condensation conditions. For example, methods for labeling polynucleotides at their 5'-terminus are described in *Oligonucleotides and Analogs*, 1991. Eckstein, Ed., Chapter 8, IRL Press; Orgel et al., 1983, Nucl. Acids Res. 11(18): 6513; and U.S. Pat. No. 5,118,800. Methods for labeling polynucleotides at the phosphate ester backbone are described in *Oligonucleotides and Analogs*, 1991. Eckstein, Ed., Chapter 9, IRL Press. Methods for labeling polynucleotides at their 3'-terminus are described in Nelson et al., 1992, Nucl. Acids Res. 20(23):6253-6259; U.S. Pat. No. 5,401,837; and U.S. Pat. No. 5,141,813. For a review of labeling procedures, the reader is referred to Haugland, *In: Excited States of Biopolymers*, 1983, Steiner. Ed., Plenum Press, NY. All of these disclosures are incorporated herein by reference.

5.6 Methods Utilizing the Dyes and Reagents of the Invention

The rhodamine dyes, energy-transfer dye pairs and conjugates incorporating the dyes and energy-transfer dye pairs of the present invention are well suited to any method utilizing fluorescent detection, particularly aqueous applications and methods requiring the simultaneous detection of multiple spatially-overlapping analytes. The various dyes and conjugates of the invention are particularly well suited for identifying classes of polynucleotides that have been subjected to a biochemical separation procedure, such as electrophoresis, or that have been distributed among locations in a spatially-addressable hybridization array.

The various dyes of the invention can be conjugated to peptides, proteins, antibodies, and antigens. Dye-antibody conjugates are awful for sandwich-type immunosorbent assays. Especially preferred are bead-based assays for detection of peptides, cells, and other cellular components where the dyes of the invention are conjugated to antibodies.

In a preferred category of methods referred to herein as "fragment analysis" or "genetic analysis" methods, labeled polynucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography, and, the separated fragments are detected subsequent to the separation, e.g., by laser-induced fluorescence. In a particularly preferred embodiment, multiple classes of polynucleotides are separated simultaneously and the different classes are distinguished by spectrally resolvable labels.

One such fragment analysis method known as amplified fragment length polymorphism detection (AmpFLP) is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphates in the PCR.

In another such fragment analysis method known as nick translation, a reaction is used to replace unlabeled nucleotides in a double-stranded (ds) DNA molecule with labeled nucleotides. Free 3'-hydroxyl groups are created within the dsDNA by "nicks" caused by treatment with deoxyribonuclease I (DNAase I). DNA polymerase I then catalyzes the addition of a labeled nucleotide to the 3'-hydroxyl terminus of the nick. At the same time, the 5' to 3'-exonuclease activity of this enzyme eliminates the nucleotide at the 5'-phosphoryl terminus of the nick. A new nucleotide with a free 3'-OH group is incorporated at the position of the original excised nucleotide, and the nick is shifted along by one nucleotide in the 3' direction. This 3' shift will result in the sequential addition of new labeled nucleotides into the dsDNA. The nick-translated polynucleotide is then analyzed, for example, by using a separation process such as electrophoresis.

Another exemplary fragment analysis method is based on variable numbers of tandem repeats, or VNTRs. VNTRs are regions of double-stranded DNA that contain multiple adjacent copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e.; tandem repeats of DNA characterized by a short (2-4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15-30 repeats per block. Many of these repeat regions are polymorphic in length and can therefore serve as useful genetic markers. Preferably, in VNTR or STR methods, label is introduced into the polynucleotide fragments using a labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes. Such sets are readily assembled from the dyes and energy-transfer dye pairs of the invention by measuring emission and absorption bandwidths with commercially available spectrophotometers. More preferably, the classes arise in the context of the chemical or chain termination methods of DNA sequencing, and most preferably the classes arise in the context of the chain termination methods, i.e., dideoxy DNA sequencing, or Sanger-type sequencing.

Sanger-type sequencing involves the synthesis of a DNA strand by a DNA polymerase in vitro using a single-stranded or double-stranded DNA template whose sequence is to be determined. Synthesis is initiated at a defined site based on where an oligonucleotide primer anneals to the template. The synthesis reaction is terminated by incorporation of a terminator that will not support continued DNA elongation. When proper proportions of dNTPs and a single terminator complementary to A, G, C or T are used, enzyme-catalyzed primer extension will be terminated in a fraction of the extension products at each site where the terminator is incorporated. If labeled primers or labeled terminators are used for each reaction, the sequence information can be detected by fluorescence after separation of the resultant primer extension products by high-resolution electrophoresis. In the chain termination method, dyes or energy-transfer dye pairs of the invention can be attached to either the sequencing primers or terminators. The dyes or energy-transfer dye pairs can be linked to a complementary functionality on the 5'-end of the primer, e.g. following the teaching in Fung et al, U.S. Pat. No. 4,757,141; on the base of a primer; or on the base of a terminator, e.g. via the alkynylamino or other linking groups described above. Concentration ranges for the various enzymes, primers, dNTPs and labeled terminators are those commonly employed in the art.

In each of the above fragment analysis methods, labeled extension products are preferably separated by electrophoretic procedures, e.g. *Gel Electrophoresis of Nucleic Acids: A Practical Approach*, 1981, Rickwood and Hames, Eds., IRL Press Limited, London; Osterman, 1984, *Methods of Protein and Nucleic Acid Research*, Vol. 1 Springer-Verlag, Berlin; or U.S. Pat. Nos. 5,374,527, 5,624,800 and/or 5,552,028. Preferably, the type of electrophoretic matrix is crosslinked or uncrosslinked polyacrylamide having a concentration (weight to volume) of between about 2-20 weight percent. More preferably, the polyacrylamide concentration is between about 4-8 percent. Preferably, in the context of DNA sequencing, the electrophoresis matrix includes a denaturing agent, e.g., urea, formamide, and the like. Detailed procedures for constructing such matrices are given by Maniatis at al., 1980, "Fractionation of Low Molecular Weight DNA and RNA in Polyacrylamide Gels Containing 98% Formamide or 7 M Urea," *Methods in Enzymology* 65:299-305; Maniatis et al., 1975, "Chain Length Determination of Small Double- and Single-Stranded DNA Molecules by Polyacrylamide Gel Electrophoresis," *Biochemistry* 14:3787-3794; Maniatis et al., 1982, *Molecular Cloning: A Laboratory Manual*, Cold Spring Harbor Laboratory, New York, pgs. 179-185; and *ABI PRISM™ 377 DNA Sequencer User's Manual, Rev. A*, January 1995, Chapter 2 (p/n 903433, The Perkin-Elmer Corporation, Foster City, Calif.). The optimal electrophoresis conditions, e.g., polymer concentration, pH, temperature, and concentration of denaturing agent, employed in a particular separation depend on many factors, including among others, the size range of the nucleic acids to be separated, their base compositions, whether they are single stranded or double stranded, and the nature of the classes for which information is sought by electrophoresis. Accordingly, application of the invention may require standard preliminary testing to optimize conditions for particular separations.

Subsequent to electrophoretic separation, the labeled extension products are detected by measuring the fluorescence emission from the labels. To perform such detection, the labeled products are illuminated by standard means, e.g. high intensity mercury vapor lamps, lasers, or the like. The illumination wavelength will depend upon the spectral properties of the particular label, Preferably, the illumination means is a laser having an illumination beam at a wavelength between 400 and 700 nm. More preferably, the illumination means is a laser light generated by an argon ion laser, particularly the 488 and 514 nm emission lines of an argon ion laser, or the 532 emission line of a neodymium solid-state YAG laser or the 633 nm emission line of a helium-neon laser. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g., a photomultiplier tube, a charged coupled device, or the like. Suitable exemplary electrophoresis detection systems are described elsewhere, e.g., U.S. Pat. Nos. 5,543,026; 5,274,240; 4,879,012; 5,091,652 and 4,811,218.

In preferred embodiments, the primer is unlabeled and the sequencing reaction includes, in addition to the polymerase and mixture of dNTPs, a mixture of four different terminators, one complementary to A, one complementary to G, one complementary to C and one complementary to T. Each of the different terminators is labeled with a different, spectrally resolvable dye or energy-transfer dye pair. One of the terminators is labeled with a rhodamine dye or energy-transfer dye pair of the invention. As each of the labeled terminators fluoresces at a different wavelength, following separation based on size, the identity of the 3'-terminal nucleotide of each extension product is identified by the wavelength (or color) of the label. In particularly preferred embodiments, each of the different spectrally resolvable labels can be excited using a single light source. A set of such preferred labeled terminators is provided in the Examples section. Other sets will depend upon the excitation and emission spectral properties of the various labels are readily obtained by routine methods.

The invention having been described, the following examples are provide to illustrate, and not limit, the invention.

6. Example

Synthesis of Rhodamine Dye 190

Rhodamine dye 190 was synthesized as illustrated in Schemes I and II, supra, from the appropriate aminophenol starting materials.

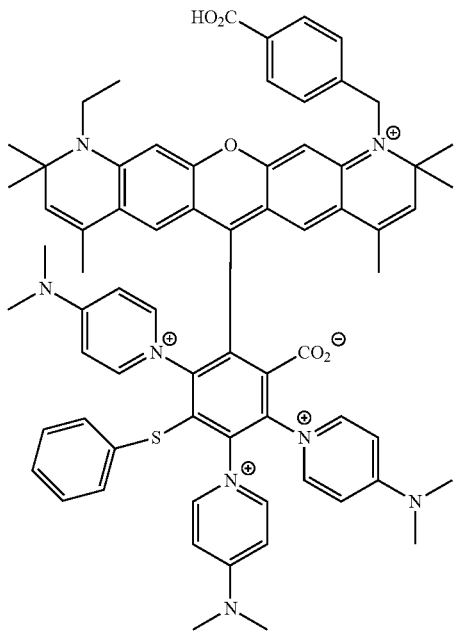

6.1 Synthesis of 202

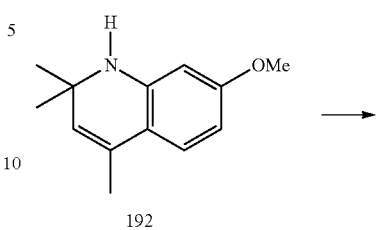

192

200

Amino-phenol compound 200 was synthesized as described in U.S. Pat. No. 5,750,409 by alkylation of 192 with ethyl iodide and sodium bicarbonate in acetonitrile followed by demethylation with boron tribromide in dichloromethane.

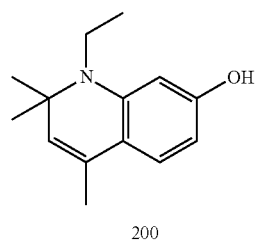

202

A solution of aminophenol 200 (4.8 g, 22 mmol) and tetrafluorophthalic anhydride 114 (4.9 g, 22 mmol; Aldrich) was refluxed in toluene (44 ml) for 3 hr. The solution was cooled to rt and the precipitate collected to yield tetrafluoro ketone 202 (6.8 g, 70%).

6.2 Synthesis of 204

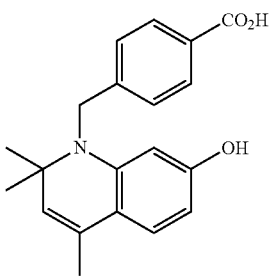

204

A suspension of the tert-butyl ester amine 194, prepared according to U.S. Pat. No. 5,688,808, (5.46 g, 20 mmol), methyl 4-(bromomethyl)benzoate (8.3 g, 36.2 mmol), sodium iodide (3.0 g, 20 mmol) and potassium carbonate (2.8 g, 20 mmol) was refluxed in acetonitrile (20 ml) for 1 hr. TLC (hexane/ethyl acetate 1/1) showed the reaction was complete. Ether was added to the cooled mixture and the solution was decanted from the solids. The solution was washed with water (2 portions of 50 ml), brine (50 ml) and dried over magnesium sulfate. The crude product was purified by chromatography on silica gel (hexane/ethyl acetate 19:1) to give white crystals of the alkylated, tert-butyl ester product (4.3 g, 10 mmol, 50%). The tert-butyl ester was dissolved in a solution of lithium hydroxide monohydrate (1.7 g, 40 mmol) in water (10 ml) and methanol (50 ml), refluxed for 2 hr and then evaporated to dryness under vacuum. The residue was extracted with diethylether (100 ml) and washed with water and brine. The organic layer was dried over magnesium sulfate, filtered and evaporated to give 204 as a tan foam. $^1$H NMR (204, $CD_2Cl_2$) δ 8.03, 2H, d; 7.45, 2H, d; 6.96, 1H, d; 6.04, 1H, d; 5.65, 1H, s; 4.55, 1H, m; 1.38, 3H, s; 1.25, 6H, s.

6.3 Synthesis of 206

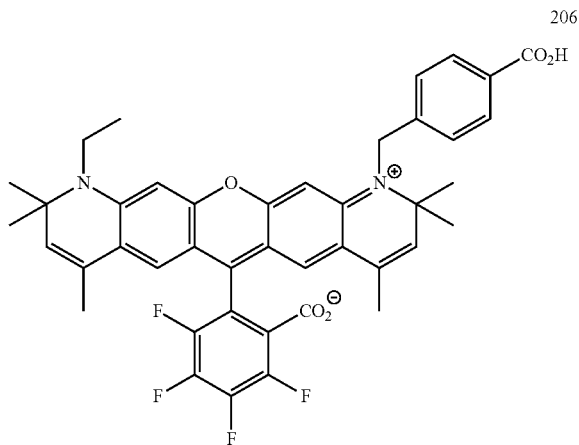

Phosphorous oxytrichloride (2.8 ml, 30 mmol) was added to a suspension of tetrafluoro ketone 202 (4.4 g, 10 mmol) in chloroform (100 ml). The suspension was stirred at rt for 30 min., aminophenol 204 (3.2 g, 10 mmol) was added and the mixture was refluxed for 3 hr. The solution was cooled to rt and the reaction quenched with water (1 ml). The solvent was evaporated and dye 206 was purified by normal phase chromatography (DCM/MeOH/HOAc, 90:10:1). Dye 206 was further purified by C18 reverse phase chromatography (MeOH/0.1 M TEAA, 4:1) to afford a dark green solid (0.65 g, 9%, Abs. max 610 nm, Em. max 632 nm, $H_2O$).

6.4 Synthesis of Dye 190

Dimethylaminopyridine (85 mg) was added to tetrafluoro dye 206 (30 mg) in 0.7 ml of dimethylformamide. After 20 hours at room temperature, TLC analysis ($CH_2Cl_2$:$CH_3OH$:$CH_3CO_2H$ 80:20:16) showed the complete disappearance of starting 206 and the appearance of a new, lower Rf spot, the tetradimethylaminopyridinium adduct. Thiophenol (0.75 ml) was added, and after another 8 hours, TLC showed partial conversion to a higher Rf spot. After concentration under vacuum, 190 was purified by reverse-phase HPLC (C18) by a gradient of 30-50% acetonitrile in 0.1M TEAA. The fractions containing 190 were combined and evaporated to give a blue oil which was precipitated in either to provide pure dye 190 as a blue solid (30 mg, Abs. Max 628 nm, Em. max 650 nm, $H_2O$).

The succinimidyl (NHS) ester of 190 was prepared from a solution of 190 (5 mg) in 100 μl dimethylformamide (DMF). Succinimidyl tetramethyluronium tetrafluoroborate (20 mg) and diisopropylamine (10 μl) were added. After 1 hour at room temperature, TLC analysis (C2-reverse phase plates, $CH_3OH$/0.1M TEAA 1:1) showed the disappearance of starting 190 and a new, lower Rf spot. The NHS ester of 190 was isolated by precipitation as a blue solid.

7. Example

Synthesis of Rhodamine Dye 196

Rhodamine dye 196 was synthesized in a manner analogous to dye 190 from the corresponding tetrafluoro dye 220.

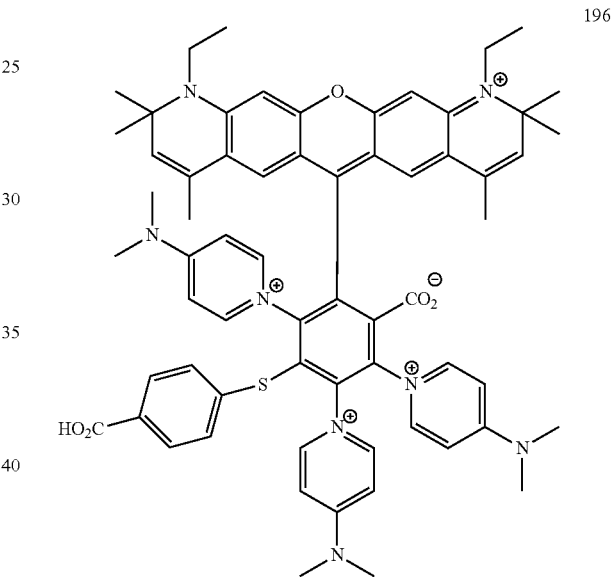

7.1 Synthesis of Tetrafluoro 220

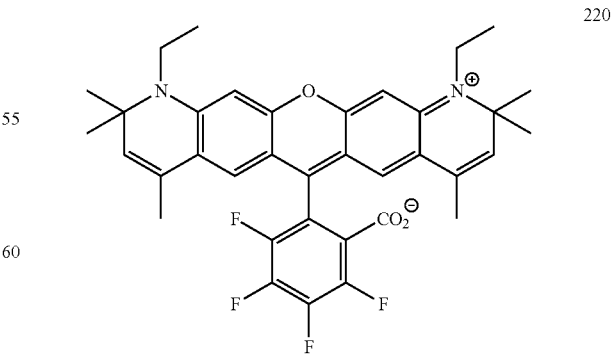

Phosphorous oxytrichloride (2.8 ml, 30 mmol) was added to a suspension of tetrafluoro ketone 202 (4.4 g, 10 mmol) in chloroform (100 ml). The suspension was stirred at rt for 30 min., aminophenol 200 (3.2 g, 10 mmol) was added and the mixture was refluxed for 3 hr. The solution was cooled to rt and the reaction quenched with water (1 ml). The solvent was evaporated and dye 220 was purified by normal phase chromatography (DCM/MeOH/HOAc, 90:10:1). Dye 220 was further purified by C18 reverse phase chromatography (CH$_3$OH: 0.1M TEAA, 4:1) to afford a dark green solid (0.65 g, 9%, Abs. max 613 nm, Em. max 643 nm, H$_2$O).

7.2 Synthesis of Rhodamine Dye 196

To a solution of 220 (100 mg) in dimethylformamide (1.5 mL) was added 4-(dimethylamino)pyridine (150 mg). Thin-layer chromatography (TLC) on silica gel eluting with 80:20:16 dichloromethane:methanol:acetic acid could distinguish tetrafluoro 220 (Rf=1) from the tetra-dimethylaminopyridinium adduct (Rf=0). After 40 hr, analysis by thin-layer chromatography showed complete conversion to the SymJAZ adduct.

To this solution, 4-carboxythiobenzene (50 mg) was added. After 10 min, TLC analysis showed conversion to rhodamine dye 196 (Rf=0.1). Purification of 196 was accomplished on C18 silica gel with stepwise elution with 20-70% methanol vs. 0.1 M triethylammonium acetate. The dye 196 eluted between 30% and 50% methanol. The solvent was evaporated and the residual blue oil was precipitated with ether to provide the dye 196 as a blue solid (85 mg, Abs. max 636 nm, Em. max 661 nm, H$_2$O).

7.3 Synthesis of Tetrafluoro 198

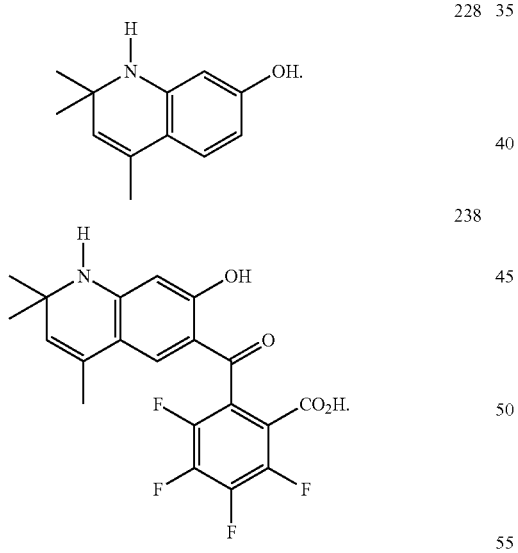

Amino-phenol compound 228 was synthesized as described in U.S. Pat. No. 5,750,409 and cyclized with tetrafluorophthalic anhydride 114 as in Example 6.1 supra to give 238 (lambda max 384 nm). The mixture of 2.6 mmole 238 and 2.6 mmole 228 in 1.2 gm phosphorus oxytrichloride and 10 ml acetonitrile was refluxed for 12 hours. The solvent was evaporated under vacuum, dissolved in several milliliters of dichloromethane and chromatographed on silica gel, eluting with dichloromethane and methanol. The product fractions were combined, evaporated and further purified by reverse-phase preparative HPLC and precipitation in 1% HCl to give 35 mg 198 as a red solid. $^1$H NMR (198, CD$_3$OD) δ 6.82, 2H, s; 6.59, 2H, s; 5.63, 2H, s; 1.9, 6H, br s; 1.4, 12H, br s.

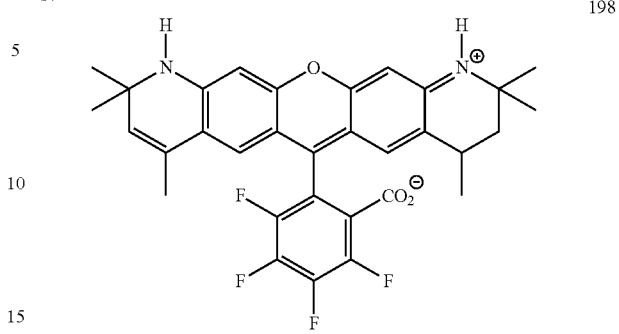

7.4 Synthesis of Tetrafluoro 290

Tetrafluoro 240 was synthesized by the method and corresponding methylated intermediates of Example 7.3. Mass spectroscopy 240: Exact Mass=662.22 (Molecular Wt.=662.67) Ex. max 624 nm, Em. max 644 nm (8M urea).

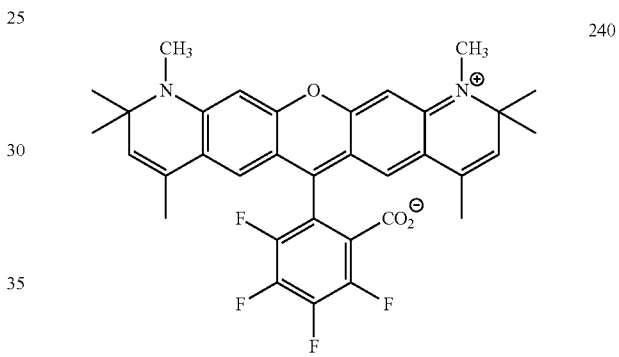

8. Example

Synthesis of Rhodamine Dye 232

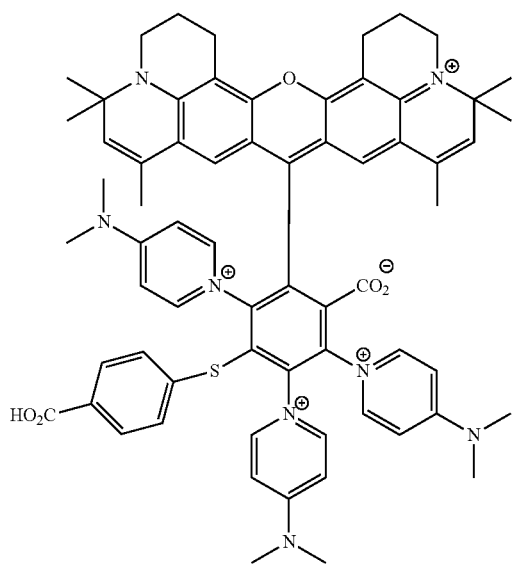

Rhodamine dye 232 was synthesized as illustrated in Schemes (I) and (II), supra, from the appropriate aminophenol starting materials.

8.1 Synthesis of Tricyclic Amine-Phenol 208

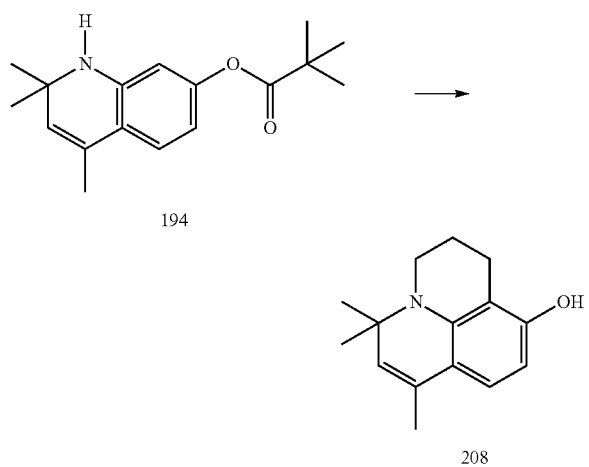

A suspension of the tert-butyl ester amine 194, prepared according to U.S. Pat. No. 5,688,808, (12.8 g, 47 mmol), 1-bromo-3-chloropropane (29.3 g, 187 mmol), sodium iodide (56.4 g, 376 mmol) and sodium bicarbonate (7.9 g, 94 mmol) was refluxed in acetonitrile (150 ml) for 18 hr. The mixture was cooled to room temperature, filtered by suction filtration and evaporated to leave a residue. The filter cake was washed with hexane (300 ml) and the filtrate was combined with the residue and washed with water (2 portions of 50 ml), brine (50 ml) and dried over magnesium sulfate. The crude cyclized product was purified by chromatography on silica gel (hexane/ethyl acetate 20:1) to leave the intermediate tricyclic pivalate ester as a pale yellow oil (9.5 g, 30 mmol, 64%). The cyclized ester was dissolved in a solution of lithium hydroxide monohydrate (2.6 g, 60 mmol) in water (15 ml) and methanol (120 ml). The solution was stirred at room temperature for 1 hr and then evaporated to dryness under vacuum. The residue was treated with 1 M HCl (30 ml) and extracted with diethylether (3 portions of 100 ml). The combined extracts were washed with 200 mM pH 7 phosphate buffer (50 ml), dried over magnesium sulfate, filtered and evaporated to give tricyclic amine-phenol 208 as a brown solid, used crude in subsequent steps.

8.2 Synthesis of Tetrafluoro Ketone 210

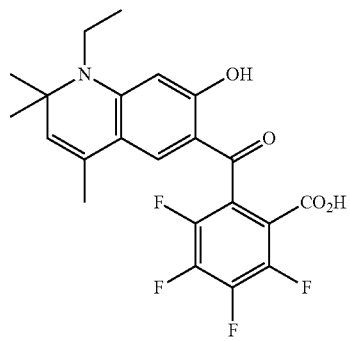

A solution of aminophenol 208 (0.67 g, 2.9 mmol) and tetrafluorophthalic anhydride (0.64 g, 2.9 mmol) was refluxed in toluene (10 ml) for 3 hr. The solution was cooled to rt and the precipitate collected, yielding tetrafluoro ketone 210 (0.92 g, 71%).

8.3 Synthesis of Tetrafluoro 212

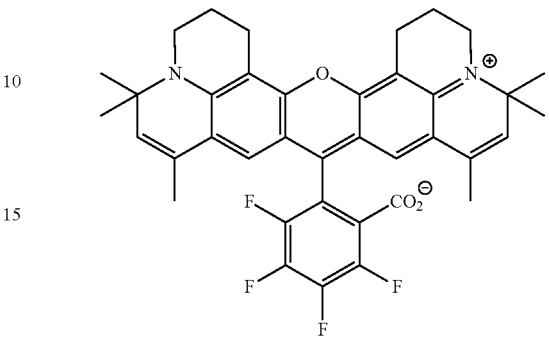

Phosphorous oxytrichloride (0.56 ml, 6 mmol) was added to a solution of F4 RAZ ketone 210 (0.91 g, 2 mmol) in chloroform (20 ml). The solution was stirred for 15 min, aminophenol 208 (0.46 g, 2 mmol) was added and the mixture was refluxed for 3 hr. The solution was cooled to rt and the reaction quenched with water (0.5 ml). Tetrafluoro dye 212 was purified by normal phase chromatography (DCM/MeOH, 20:1) and further purified by C18 reverse phase chromatography (MeOH/0.1 M TEAA, 9:1) to afford 212 as a metallic green solid (0.39 g, 30%, Abs. max 630 nm, Em. max 655 nm, 8M urea).

8.4 Synthesis of Rhodamine Dye 232

Rhodamine dye 232 was synthesized from tetrafluoro dye 212 with 4-(dimethylamino)pyridine and 4-carboxythiobenzene, as described in Section 7.2, supra, and purified by C-8 reverse phase HPLC, eluting with an acetonitrile/0.1 M TEAA gradient (Em. max 665 nm, $H_2O$).

9. Example

Synthesis of Rhodamine Dye 234

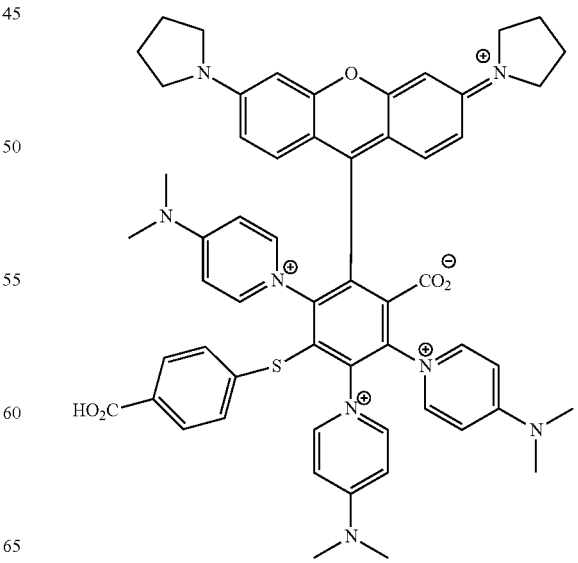

Rhodamine dye 234 was synthesized as illustrated in Schemes (I) and (II) from the appropriate aminophenol starting materials.

9.1 Synthesis of Pyrrolidinyl Phenol 214

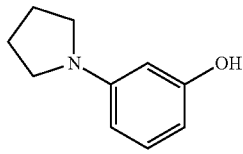

A solution of m-aminophenol (12.6 g, 115 mmol) was heated in 1,4-dibromobutane (50 g, 230 mmol) at 130° C. for 18 hr. The mixtures was cooled to room temperature and the gum was triturated with ether and then ethyl acetate. The gum was dissolved in 120 ml of 1 M NaOH and extracted with ethyl acetate (100 ml). The layers were separated and the organic phase was washed with water twice and then brine. After drying over magnesium sulfate, the crude product was purified by silica gel chromatography (DCM/methanol 100:1) to give a pale yellow solid. The solid was refluxed in toluene (500 ml) and triethylamine (16 ml, 115 mmol) for 2 hr., cooled to room temperature, and washed with water. The solvent was evaporated to leave pyrrolidinyl phenol 214 as a white solid (11 g, 60%). $^1$H NMR (214, d6-DMSO) δ 8.98, 1H, s; 6.90, 1H, t; 5.95, 3H, m; 3.18, 4H, m; 1.95, 4H, m.

9.2 Synthesis of Pyrrolidinyl Ketone 216

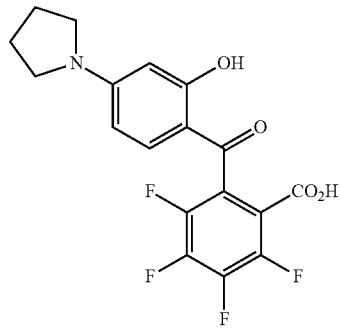

A solution of aminophenol 214 (0.74 g, 4.6 mmol) and tetrafluorophthalic anhydride (1 g, 4.6 mmol) was refluxed in toluene (5 ml) for 3 hr. The solution was cooled to rt and the precipitated collected to yield pyrrolidinyl ketone 216 (1.3 g, 77%).

9.3 Synthesis of Tetrafluoro 218

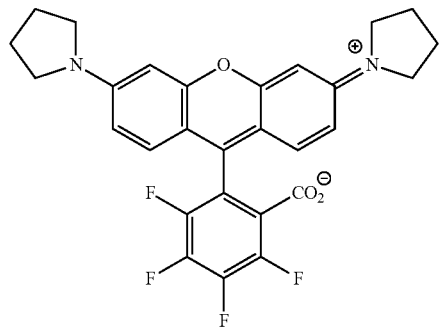

Phosphorous oxytrichloride (1 ml, 10 mmol) was added to a solution of pyrrolidinyl ketone 216 (1.3 g, 3.5 mmol) in chloroform (10 ml). The solution was stirred for 15 min., aminophenol 214 (0.56 g. 3.5 mmol) was added and the solution was refluxed for 4 hr. The solution was cooled to rt and the reaction quenched with water (0.5 ml). Tetrafluoro 218 was purified by C18 reverse phase chromatography (MeOH/0.1 M TEAA, 4:1) to afford metallic green solid (0.73 g, 41%, Abs. max. 576 nm, Em. max 594 nm, $CH_3OH$).

9.4 Synthesis of Rhodamine Dye 234

Rhodamine dye 234 (Abs. max 590 nm, Em. max 606 nm, $CH_3OH$; Em. max 61.1 nm, $H_2O$) was synthesized from 218 as described in Section 7.2, supra, and purified by C-8 reverse phase HPLC, eluting with an acetonitrile/0.1 M TEAA gradient.

10. Example

Synthesis of Rhodamine Dye 236

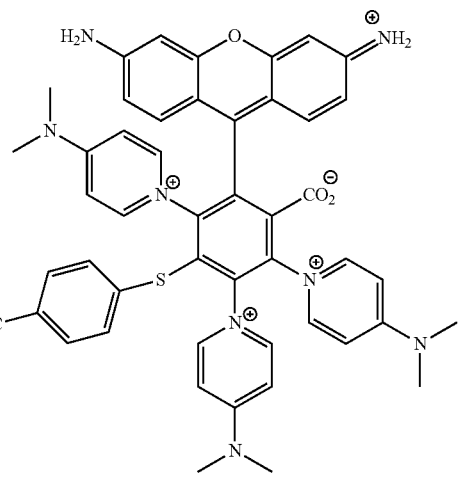

Rhodamine dye 236 was synthesized from 3-(bisbenzylamino)phenol and tetrafluorophthalic anhydride 114 as illustrated in Schemes I and II.

10.1 Synthesis of Bis-Benzyl Tetrafluoro Ketone 222

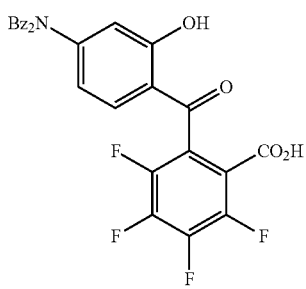

A solution of 3-(bisbenzylamino)phenol (14.5 g, 50 mmol) and tetrafluorophthalic anhydride (11 g, 50 mmol) were refluxed in toluene (50 ml) for 18 hr. The solvent was evaporated and the residue purified by C18 reverse phase chromatography (MeOH/water, 7:3) to afford bis-benzyl tetrafluoro ketone 222 as a white solid (6.5 g, 25%).

10.2 Synthesis of Tetra-Benzyl Tetrafluoro 224

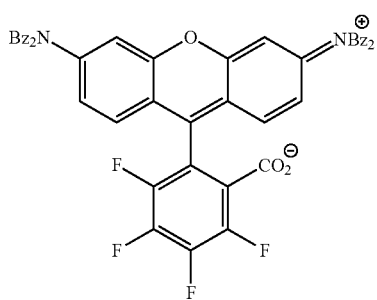

Phosphorous oxytrichloride (3.3 ml, 35 mmol) was added to a solution of bis-benzyl ketone 222 (6.0 g, 12 mmol) in chloroform (60 ml). The solution was stirred for 15 min., 3-(bisbenzylamino)phenol (3.4 g, 12 mmol) was added and the mixture was refluxed for 3 hr. The solution was cooled to room temperature and the reaction was quenched with water (1 ml). The solvent was evaporated and the residue purified by C18 reverse phase chromatography (MeOH/0.1 M TEAA, 9:1) to afford tetra-benzyl tetrafluoro dye 224 as a dark red solid (0.62 g, 7%, Abs. max 566 nm).

10.3 Synthesis of Tetrafluoro 226

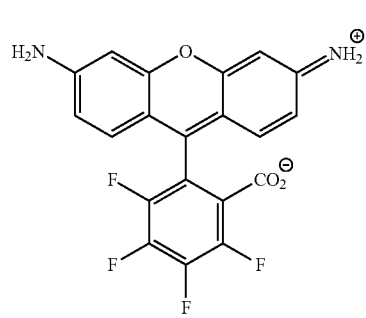

A suspension of dye 224 (0.62 g, 0.8 mmol) was heated in conc. HBr (20 ml) to 110° C. for 45 min. The reaction mixture was poured into ice-water and the precipitated was collected and purified by C18 reverse phase chromatography ($CH_2OH$: 0.1M TEAA, 3:2) to afford debenzylated dye 226 as a metallic green solid (100 mg, 31%, Abs. max 521 nm).

10.4 Synthesis of Rhodamine Dye 236

Rhodamine dye 236 was synthesized from 226 as described in Section 7.2, supra. Purification of 236 was accomplished on C18 silica gel with stepwise elution with 20-70% methanol vs. 0.1 M triethylammonium acetate. The dye 236 eluted between 30% and 50% methanol. The solvent was evaporated and the residual blue oil was precipitated with ether to provide the title dye as a blue solid (85 mg; Em. max 545 nm, $H_2O$).

11. Example

Synthesis of FRET Dye 230

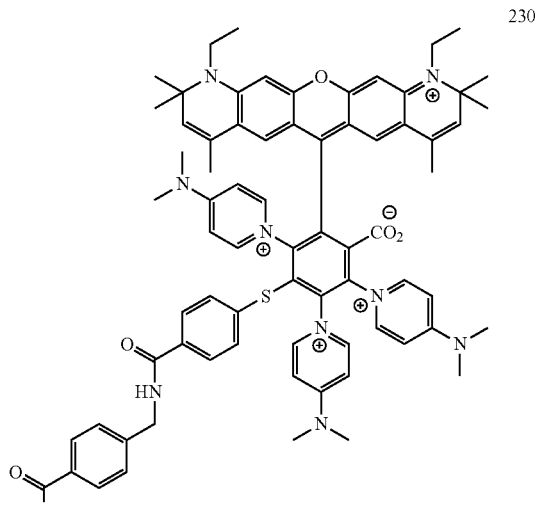

-continued

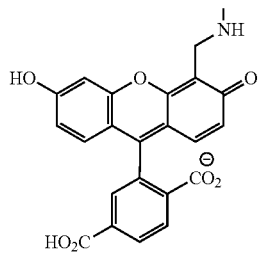

11.1 Synthesis of Succinimidyl (NHS) Ester of 196

To a solution of dye 196 (5 mg) in DMF (100 μl) was added succinimidyl tetramethyluronium tetrafluoroborate (20 mg) and diisopropylamine (10 μL). TLC analysis on C2-reverse phase silica gel eluting with 1:1 methanol:0.1 M triethylammonium acetate could distinguish dye 196 (Rf=0.2) from 196 succinimidyl ester (Rf=0). After 1 hr, the reaction appeared to be complete and was partitioned between 5% HCl and dichloromethane. The organic layer was dried over $Na_2SO_4$ and the solvent evaporated to yield the 196 NHS ester as a blue solid.

11.2 Synthesis of FRET Dye 230

Energy-transfer (FRET) dye 230 is prepared by coupling 196 NHS ester and 4-aminomethylbenzoic acid and 4'-aminomethyl-6-carboxyfluorescein (Molecular Probes Inc., Eugene, Oreg.), according to methods described in U.S. Pat. No. 5,863,727. For example, 1 mmole of 196 NHS dissolved in 250 μl of DMSO is added to a solution of 2 μmole 4'-aminomethyl-6-carboxyfluorescein in 100 μl DMSO and 20 μl triethylamine. After mixing the solution is let stand for about 12 hours, monitoring the progress of coupling by reverse phase HPLC.

12. Example

Synthesis of FRET Dye 230-ddATP

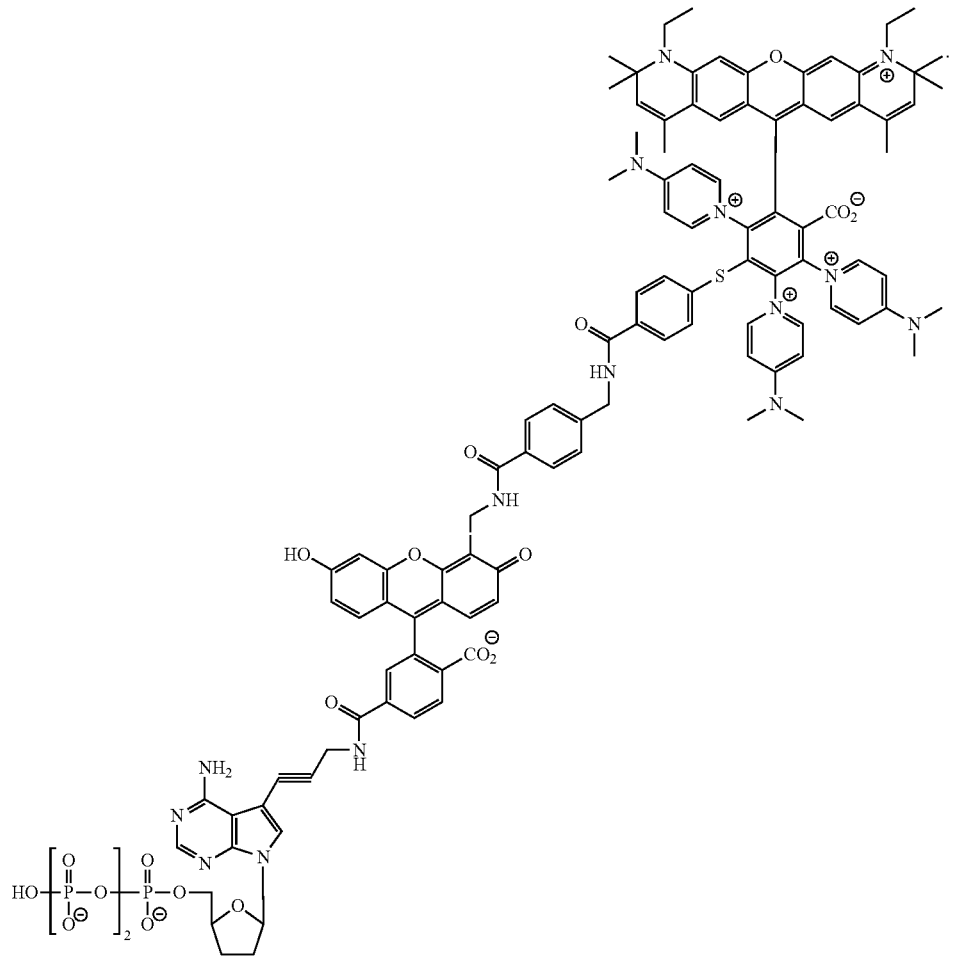

FRET dye 230 is activated as the NHS ester by the method of Example supra 11.1 and coupled to 7-deaza-7-aminopropargyl, 2'-3' dideoxyadenosine-5'-triphosphate according to the methods in U.S. Pat. Nos. 5,821,356 and 5,770,716 to give FRET dye 230-ddATP. Alternatively, 4'-trifluoroacetamidomethyl 6-carboxyfluorescein NHS ester is coupled with 7-deaza-7-aminopropargyl, 2'-3' dideoxyadenosine-5'-triphosphate to give the intermediate dye-nucleotide. The trifluoroacetyl protecting group is removed under basic conditions and the intermediate dye nucleotide is coupled with 230 NHS ester to give FRET dye 230-ddATP by a two-step method of conjugating the energy-transfer dye to a nucleotide.

13. Example

Sanger-Type Sequencing Using an Energy Transfer Dye

Following the methods described in U.S. Pat. Nos. 5,821,356 and 5,366,860, Sanger-type terminator sequencing was performed on pGEM (PE Biosystems, Foster City, Calif.) using Taq FS polymerase (PE Biosystems, Foster City, Calif.), a mixture of four dNTPs, an unlabeled sequencing primer and a single labeled terminator (6-FAM-230-ddATP). A plot of the resultant sequencing data, obtained on an ABI PRISM Model 310 instrument (PE Biosystems, Foster City, Calif.) is provided in FIG. 1.

14. Example

Four-Color Sanger-Type Sequencing

Following the methods described in U.S. Pat. Nos. 5,821,356 and 5,366,860, four-color Sanger-type terminator sequencing was performed on pGEM1 (PE Biosystems, Foster City, Calif.) using Taq FS polymerase (PE Biosystems, Foster City, Calif.), a mixture of four dNTPs, an unlabeled sequencing primer and a mixture of four, 3'-fluoro, spectrally-resolvable labeled terminators (6-FAM-230-ddATP; 5-FAM-236-7-deaza-ddGTP; 6-FAM-JON-ddTTP; 6-FAM-ROX-ddCTP). A plot of the resultant sequencing data, obtained on an ABI PRISM Model 310 instrument (PE Biosystems, Foster City, Calif.) is provided in FIG. 2.

As can be seen in FIG. 2, all of the dye-labeled polynucleotides exhibit significant fluorescence intensity. Moreover, the different dye-labeled polynucleotide exhibit sufficiently similar mobilities, resulting in good resolution.

15. Example

Anti-Human Antibody-Dye Conjugate Detection

Anti-Human Il-8 Antibody-Dye-196 Conjugate

Polyclonal anti-human IL-8 antibody (R&D Systems, Minneapolis, Minn.; 0.5 mg in 0.5 ml PBS) was incubated with 50 µl of 1 M $Na_2CO_3$ and 105 µg of dye 196 for 1 hour at room temperature, in the dark. The antibody-dye-196 conjugate (Abs. max 666 nm, $H_2O$) was separated from the free dye using a sephadex G-50 (fine) size exclusion column. The conjugate was passed through a 0.2µ filter and stored at 4° C. in PBS. The concentration of the antibody was determined according to the following equation: $[A_{280}-(0.82 \times A_{640})]/170,000$, where $0.82=A_{280}/A_{640}$ of the free dye and 170,000 is the extinction coefficient for the antibody. The concentration of the dye was determined according to the following equation: $A_{640}/120,000$, where 120,000 is the extinction coefficient for dye 196. The dye 196-labeled polyclonal anti-human IL-8 antibody concentration was 0.18 mg/ml with an F/P ratio of 2.3/1.

Preparation of Monoclonal Anti-Human IL-8 Antibody Coated Beads

Goat anti-mouse IgG (Fc) polystyrene beads (200 ml of 0.5% w/v; 6 µm bead diameter; Spherotech) were first washed 3 times by centrifugation and resuspension of the bead pellet with 1 ml PBS. 4 µg of monoclonal anti-human IL-8 antibodies (R&D Systems) was added to the bead suspension for a final volume of 1 ml. After incubation for 16 hrs at room temperature with gentle mixing, the monoclonal antibody-coated beads were washed 2 times as described above and resuspended in 1 ml PBS. The final bead concentration was 0.1% w/v or $8 \times 10^6$ beads/ml. The monoclonal antibody-coated beads were stable for approximately 1 month when stored at 4° C.

Fluorescent-Linked Immunosorbant Assay (FLISA)

To generate a standard curve, a two-fold serial dilution of human IL-8 peptide (R&D Systems) in 50 µl FLISA buffer (PBS containing 1 mg/ml BSA, 0.35 M NaCl, 0.1% Tween 20, and 0.01% $NaN_3$) were aliquoted into a 96-well plate (Corning Costar No. 3904). Subsequently, 50 µl of a mixture containing monoclonal anti-human IL-8 antibody-coated beads and dye 196-labeled polyclonal anti-human IL-8 antibodies in FLISA buffer was then added to each well. The final concentrations in a total volume of 100 µl per well were 64,000 antibody-coated beads/ml and 0.11 µg/ml of dye 196-labeled polyclonal anti-human IL-8 antibodies. The serial dilution for IL-8 peptide ranged from 2,000-2.0 pg/ml. The assay contained eight replicates, and control wells containing no peptide were included. After incubating overnight at room temperature in the dark, the 96-well plate was scanned using the FMAT 8100 HTS System (PE Biosystems, Foster City, Calif.), a macroconfocal imaging system equipped with a 633-nm HeNe laser and 2-channel fluorescence detection (FL1: 650-685 nm, FL2: 685-720 nm). A 1 $mm^2$ area of each well is raster scanned at a depth of focus of 100 µm and at a rate of 1 sec/well, with 256 scan lines generated. The fluorescence intensity associated with each bead is then obtained from the digitized images and the average fluorescence intensity per bead is calculated per well. A log vs log graph of the average fluorescence intensity in FL1 vs pg/ml of the IL-8 peptide is shown in FIG. 4. The linear dynamic range of the assay is 250-3.9 pg/ml IL-8.

While the present invention has been described by reference to the preferred embodiments and examples detailed above, it is to be understood that these examples are intended in an illustrative, rather than limiting, sense. It is contemplated that modifications that do not depart from the spirit of the invention will readily occur to those of skill in the art. Any such modifications are intended to fall within the scope of the appended claims.

All of the references, publications and patents cited in the specification are incorporated herein by reference to the same extent as if each reference were individually incorporated by reference.

We claim:

1. A rhodamine dye or a salt thereof, comprising a rhodamine-type parent xanthene ring having attached to the xanthene C9 carbon a phenyl group that is further substituted with an ortho carboxy or ortho sulfonate group or a salt thereof, one to three substituted or unsubstituted aminopyridinium groups and a substituted or unsubstituted alkylthio, arylthio or heteroarylthio group, wherein the rhodamine dye comprises the structure:

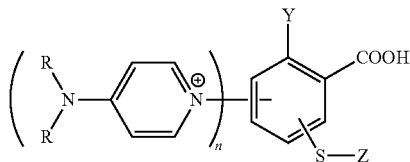

wherein:

n is an integer selected from the group consisting of 1, 2, and 3;

Y is a rhodamine-type parent xanthene ring attached to the illustrated phenyl group at the xanthene C9 carbon;

each R is independently selected from the group consisting of a $(C_1-C_6)$ alkyl or heteroalkyl, a $(C_5-C_{20})$ aryl or heteroaryl, a $(C_6-C_{26})$ arylalkyl or heteroalkyl and a $(C_5-C_{20})$ arylalkyl or heteroaryl-heteroalkyl, or when taken together, both R form a moiety selected from the group consisting of a $(C_4-C_{10})$ alkyldiyl, a $(C_4-C_{10})$ alkyleno, a heteroalkyldiyl and a heteroalkyleno;

S is sulfur;

Z is selected from the group consisting of a $(C_1-C_{12})$ alkyl, a $(C_1-C_{12})$ alkyl substituted with one or more of the same or different $W^1$ groups, a $(C_5-C_{20})$ aryl or heteroaryl and a $(C_5-C_{20})$ aryl or heteroaryl substituted with one or more of the same or different $W^2$ groups;

$W^1$ is selected from the group consisting of —X, —R, =O, —OR, —SR, =S, —NRR, =NR, —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR;

$W^2$ is selected from the group consisting of —R, —OR, —SR, —NRR, —S(O)$_2$O$^-$, —S(O)$_2$OH, —S(O)$_2$R, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR;

each X is independently a halogen; and

Y or Z is optionally substituted with L, wherein L is a bond or a linker selected from the group consisting of a hydrophobic moiety, a charged group, a member of a pair of specific binding molecules, a photo-activatable group and a reactive functional group.

2. The rhodamine dye of claim 1, wherein Z has the form $Z^1$-L-R$_x$, or a salt thereof, wherein:

$Z^1$ is selected from the group consisting of a $(C_1-C_{12})$ alkyldiyl, a $(C_1-C_{12})$ alkyldiyl independently substituted with one or more of the same or different $W^1$ groups, a $(C_5-C_{14})$ aryldiyl or heterodiyl and a $(C_5-C_{14})$ aryldiyl or heterodiyl independently substituted with one or more of the same or different $W^2$ groups;

L is selected from the group consisting of a bond and a linker; and

R$_x$ is a reactive functional group.

3. The rhodamine dye of claim 2, in which Y is selected from the group consisting of:

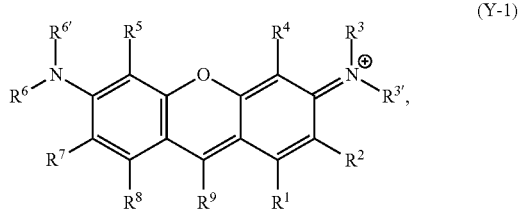

(Y-1)

-continued

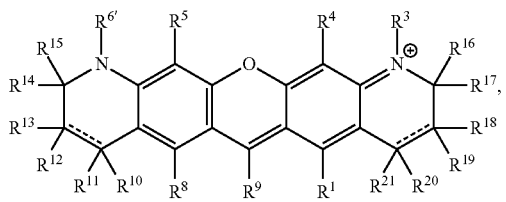
(Y-2)

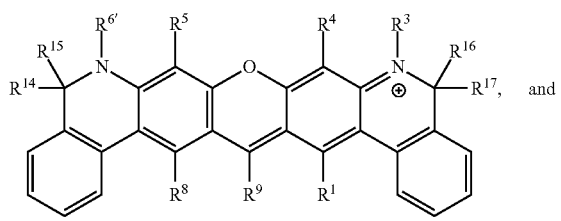
(Y-3)

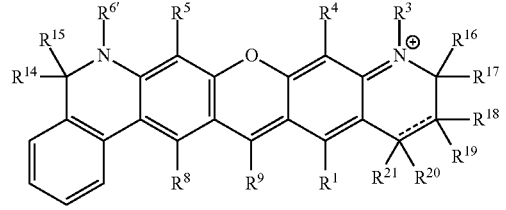
(Y-4)

and a salt thereof, wherein:
   each of $R^1$ and $R^2$ when taken alone, is independently selected from the group consisting of hydrogen and a $(C_1-C_6)$ alkyl;
   each of $R^3$ and $R^{3'}$ when taken alone, is independently selected from the group consisting of hydrogen, a $(C_1-C_6)$ alkyl, a $(C_5-C_{14})$ aryl and an arylaryl, or when taken together are a $(C_4-C_6)$ alkyldiyl or an alkyleno, or when individually taken together with $R^2$ or $R^4$ is a $(C_2-C_6)$ alkyldiyl and a $(C_2-C_6)$ alkyleno;
   $R^4$, when taken alone, is selected from the group consisting of hydrogen and a $(C_1-C_6)$ alkyl, or when taken together with $R^3$ or $R^{3'}$ is selected from the group consisting of a $(C_2-C_6)$ alkyldiyl and an alkyleno;
   $R^5$, when taken alone, is selected from the group consisting of hydrogen and a $(C_1-C_6)$ alkyl, or when taken together with $R^6$ or $R^{6'}$ is selected from the group consisting of a $(C_2-C_6)$ alkyldiyl and an alkyleno;
   each of $R^6$ and $R^{6'}$ when taken alone, is independently selected from the group consisting of hydrogen, a $(C_1-C_6)$ alkyl, a $(C_5-C_{14})$ aryl and an arylaryl, or when taken together are a $(C_4-C_6)$ alkyldiyl or an alkyleno, or when individually taken together with $R^5$ or $R^7$ is a $(C_2-C_6)$ alkyldiyl or an alkyleno;
   $R^7$, when taken alone, is selected from the group consisting of hydrogen and a $(C_1-C_6)$ alkyl, or when taken together with $R^6$ or $R^{6'}$ is a $(C_2-C_6)$ alkyldiyl or an alkyleno;
   $R^8$, when taken alone, is selected from the group consisting of hydrogen and a $(C_1-C_6)$ alkyl;
   $R^9$ indicates the point of attachment to the ortho-carboxyphenyl bottom ring; and
   each of $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ is independently selected from the group consisting of hydrogen and a $(C_1-C_6)$ alkyl, or
   $R^{10}$, $R^{11}$, $R^{12}$ and $R^{13}$ taken together are a $(C_5-C_{14})$ aryleno or a $(C_5-C_{14})$ aryleno substituted with one or more of the same or different $(C_1-C_6)$ alkyl(s), or
   $R^{18}$, $R^{19}$, $R^{20}$ and $R^{21}$ taken together are a $(C_5-C_{14})$ aryleno or an aryleno substituted with one or more of the same or different $(C_1-C_6)$ alkyl(s).

4. The rhodamine dye of claim 3, wherein $R^2$, when taken together with $R^3$ or $R^{3'}$ is a $(C_2-C_6)$ alkyldiyl or an alkyleno.

5. The rhodamine dye of claim 4, wherein:
   alkyl is selected from the group consisting of methyl, ethyl and a propyl;
   aryl is selected from the group consisting of phenyl and naphthyl;
   arylaryl is biphenyl;
   alkyldiyl or alkyleno bridges formed by taking $R^2$ together with $R^3$ or $R^{3'}$, $R^7$ together with $R^6$ or $R^{6'}$, or $R^4$ together with $R^3$ or $R^{3'}$, are selected from the group consisting of ethano, a propano, 1,1-dimethylethano, 1,1-dimethylpropano and 1,1,3-trimethylpropano;
   aryleno bridges formed by taking $R^1$ together with $R^2$ are selected from the group consisting of benzo and naphtho;
   alkyldiyl or alkyleno bridge formed by taking $R^3$ together with $R^{3'}$, or $R^6$ together with $R^{6'}$, is a butano;
   alkyldiyl or alkyleno bridges formed by taking $R^5$ together with $R^6$ or $R^{6'}$ are selected from the group consisting of ethano, a propano, 1,1-dimethylethano, 1,1-dimethylpropano and 1,1,3-trimethylpropano; and
   aryleno bridge formed by taking $R^{10}$, $R^{11}$, $R^{12}$ and $R^{13}$ together, or $R^{18}$, $R^{19}$, $R^{20}$ and $R^{21}$ together, is benzo.

6. The rhodamine dye of claim 4, wherein L is a bond.

7. The rhodamine dye of claim 2, wherein $R_x$ is selected from the group consisting of carboxyl, carboxylate, an ester and an activated ester.

8. The rhodamine dye of claim 2, wherein $Z^1$ is selected from the group consisting of a $(C_1-C_{12})$ alkyleno, a $(C_1-C_{12})$ alkano, a $(C_5-C_{10})$ aryldiyl or heteroaryldiyl, phenyldiyl, phena-1,4-diyl, naphthadiyl, naphtha-2,6-diyl, pyridindiyl and purindiyl.

9. The rhodamine dye of claim 2, wherein Y is selected from the group consisting of:

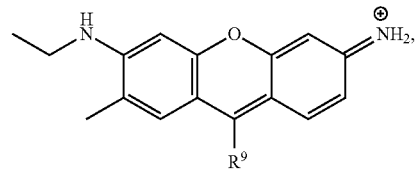
(Y-20a)

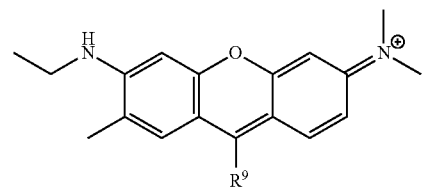
(Y-21a)

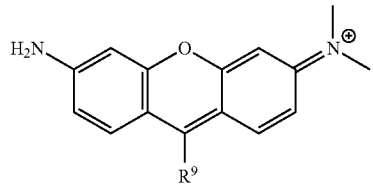
(Y-22a)

(Y-23a), (Y-24a), (Y-25a), (Y-31a), (Y-34a), (Y-35a), (Y-36a), (Y-39a), (Y-41a), (Y-42a), (Y-43a), (Y-44a), (Y-45a), and -continued

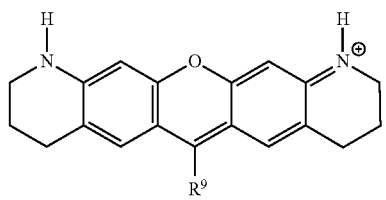
(Y-46a)

10. The rhodamine dye of claim 2, wherein L is a bond.

11. The rhodamine dye of claim 2 which comprises the structure:

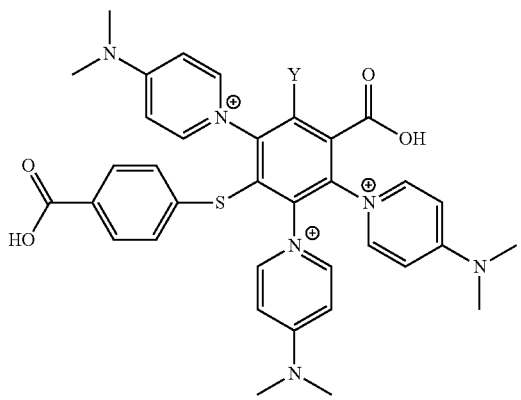

or a salt thereof.

12. The rhodamine dye of claim 11, wherein Y is selected from the group consisting of Y-1, Y-2, Y-3 and Y-4.

13. The rhodamine dye of claim 11, wherein Y is selected from the group consisting of Y-20a, Y-21a, Y-22a, Y-23a, Y-24a, Y-25a, Y-31a, Y-34a, Y-35a, Y-36a, Y-39a, Y-41a, Y-42a, Y-43a, Y-44a, Y-45a and Y-46a.

14. The rhodamine dye of claim 1 having the structure:

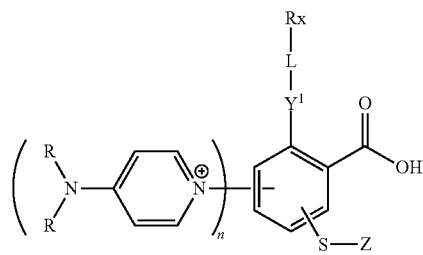

wherein:
- $Y^1$ is a rhodamine-type parent xanthene ring attached to the illustrated phenyl group at the xanthene C9 carbon;
- L is a bond or linker attached to a xanthene nitrogen atom or a xanthene C4 carbon; and
- $R_x$ is a reactive functional group.

15. The rhodamine dye of claim 14, wherein $Y^1$ is selected from the group consisting of:

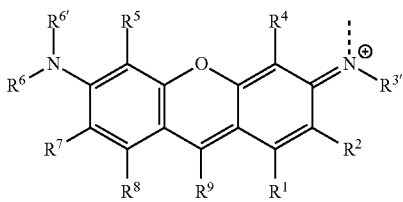
(Y-1b)

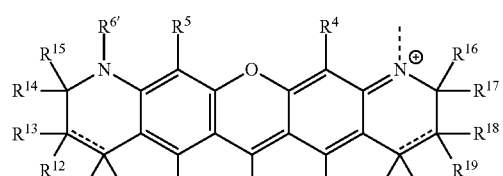
(Y-2b)

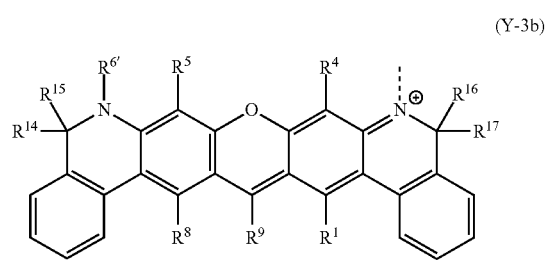
(Y-3b)

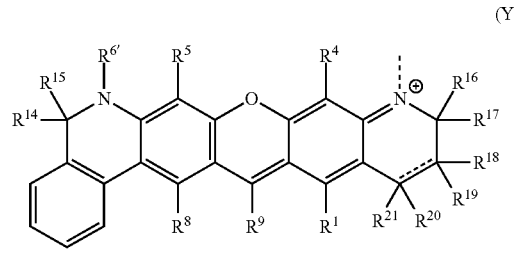
(Y-4b)

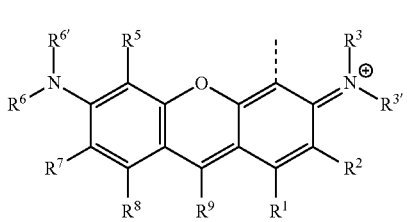
(Y-1c)

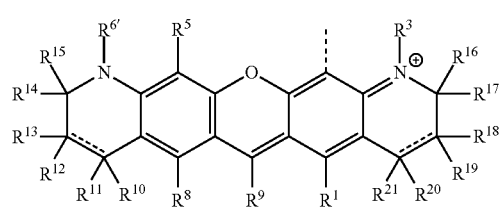
(Y-2c)

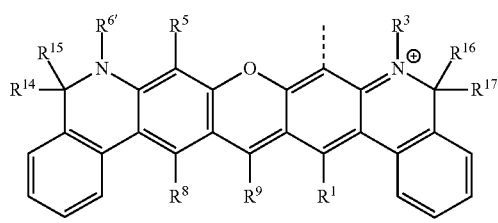
(Y-3c)

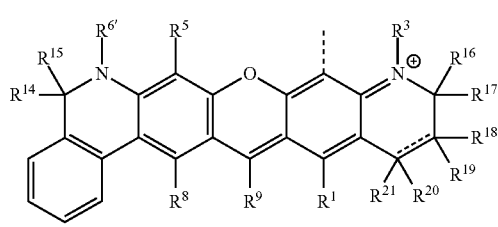
(Y-4c)

wherein the dashed line at the nitrogen or C4 atom indicates the point of attachment of L.

16. The rhodamine dye of claim 15, wherein:

alkyl is selected from the group consisting of methanyl, ethanyl and propanyl;

aryl is selected from the group consisting of phenyl and naphthyl;

arylaryl is biphenyl;

alkyldiyl or alkyleno bridges formed by taking $R^2$ together with $R^3$ or $R^{3'}$, $R^7$ together with $R^6$ or $R^{6'}$, or $R^4$ together with $R^3$ or $R^{3'}$, are selected from the group consisting of ethano, a propano, 1,1-dimethylethano, 1,1-dimethylpropano and 1,1,3-trimethylpropano;

aryleno bridges formed by taking $R^{10}$, $R^{11}$, $R^{12}$ and $R^{13}$ together or $R^{18}$, $R^{19}$, $R^{20}$ and $R^{21}$ together are benzo.

17. The rhodamine dye of claim 14, wherein L is selected from the group consisting of a $(C_1-C_6)$ alkyldiyl, a $(C_1-C_6)$ alkano, a $(C_5-C_{20})$ aryldiyl, phenyldiyl, phena-1,4-diyl, naphthyldiyl, naphtha-2,6-diyl, naphtha-2,7-diyl, a $(C_6-C_{26})$ arylalkyldiyl, —$(CH_2)_i$-φ- and —$(CH_2)_i$-Ψ-, where each i is independently an integer having the value between 1 and 6, φ is selected from the group consisting of a $(C_5-C_{20})$ aryldiyl, phenyldiyl and phena-1,4-diyl and Ψ is selected from the group consisting of naphthyldiyl, naphtha-2,6-diyl and naphtha-2,7-diyl.

18. The rhodamine dye of claim 14, wherein $R_x$ is selected from the group consisting of carboxyl, carboxylate, an ester and an activated ester.

19. The rhodamine dye of claim 14, wherein Z is selected from the group consisting of a $(C_1-C_{12})$ alkyl, a $(C_1-C_{12})$ alkanyl, a $(C_5-C_{10})$ aryl or heteroaryl, phenyl, naphthyl, naphth-1-yl, naphth-2-yl, pyridyl and purinyl.

20. The rhodamine dye of claim 14, wherein $Y^1$ is selected from the group consisting of:

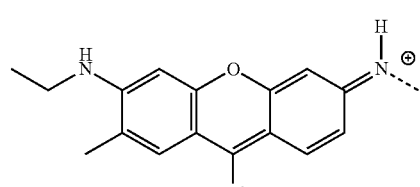
(Y-20b)

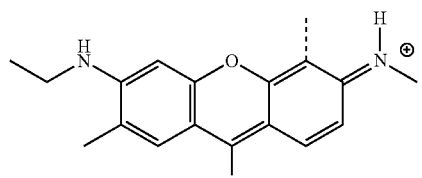
(Y-20c)

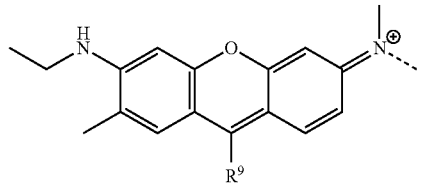
(Y-21b)

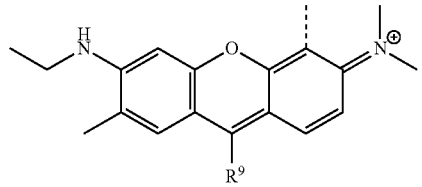
(Y-21c)

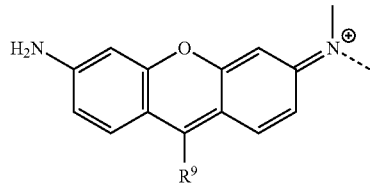
(Y-22b)

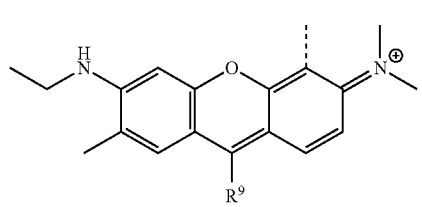
(Y-22c)

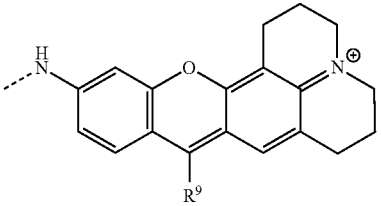
(Y-23b)

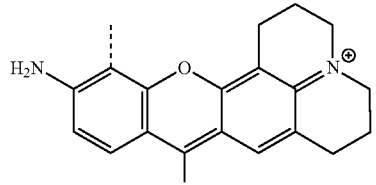
(Y-23c)

-continued
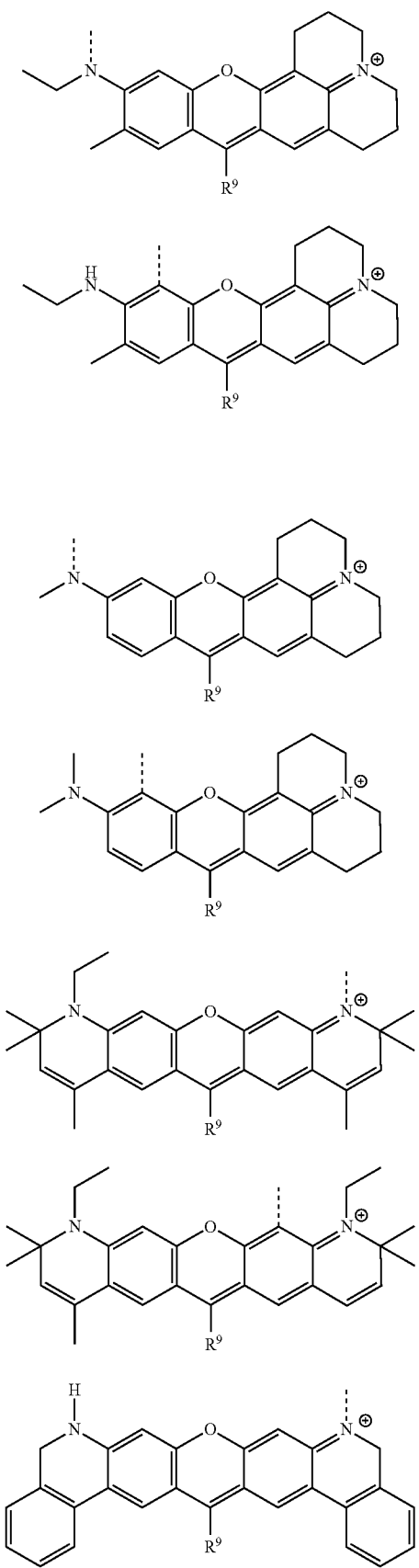
(Y-24b)
(Y-24c)
(Y-25b)
(Y-25c)
(Y-31b)
(Y-31c)
(Y-34b)
-continued
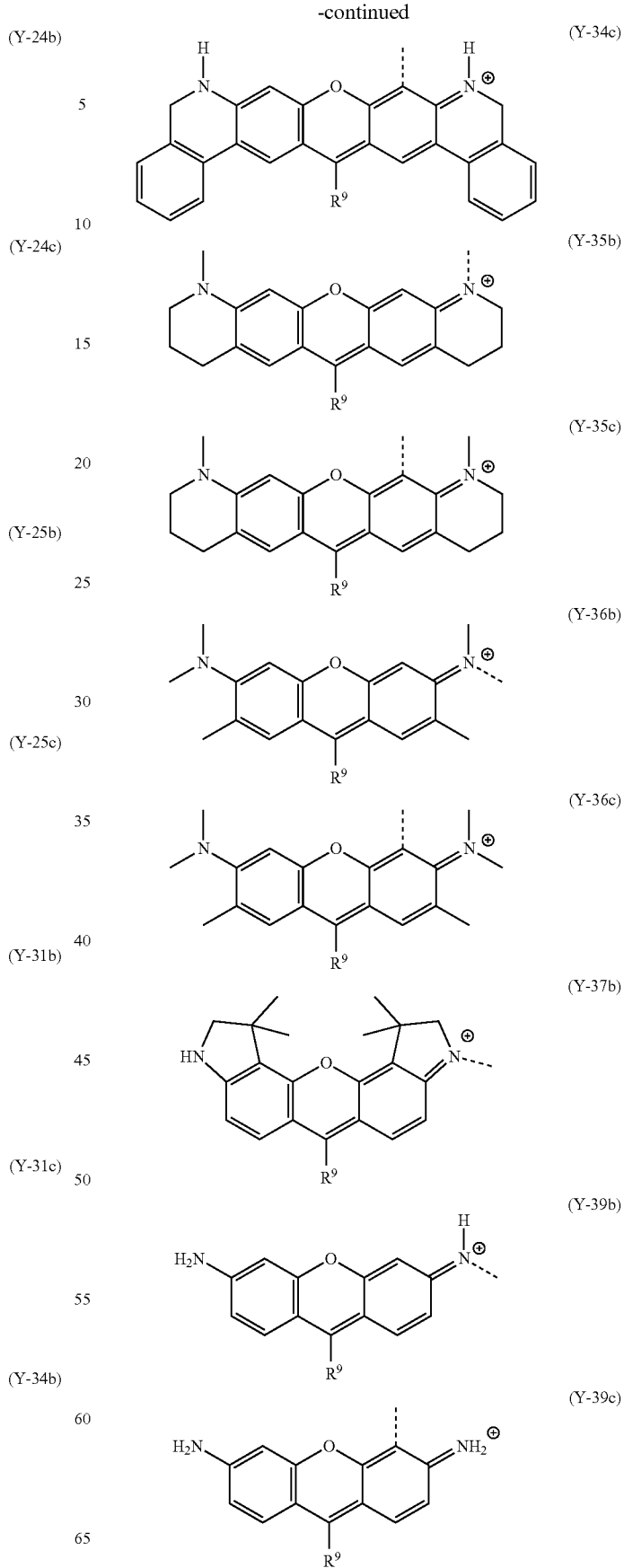
(Y-34c)
(Y-35b)
(Y-35c)
(Y-36b)
(Y-36c)
(Y-37b)
(Y-39b)
(Y-39c)

-continued (Y-41c)
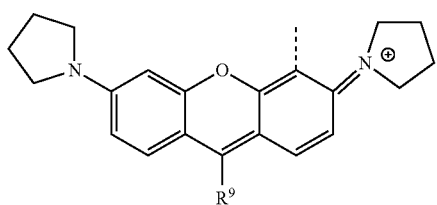

(Y-42b)
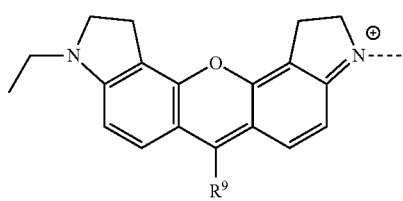

(Y43b)
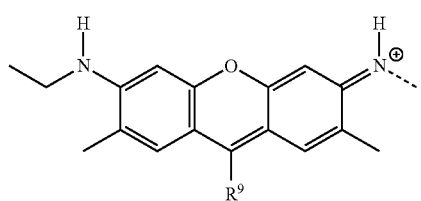

(Y-43c)
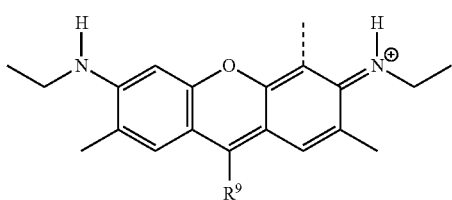

(Y-46b)
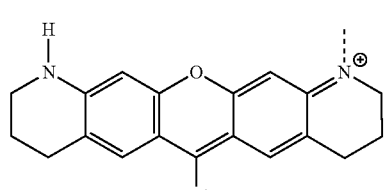

(Y-46c)
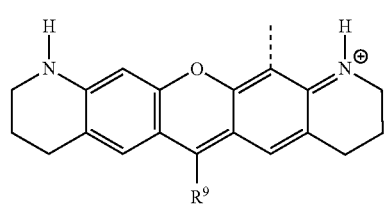

wherein the dash at the nitrogen or C4 atom indicates the point of attachment of L.

21. The rhodamine dye of claim 14 having the structure:

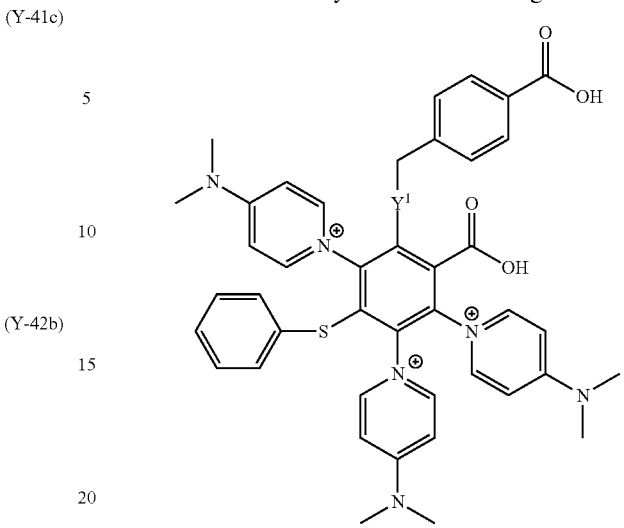

or a salt thereof.

22. The rhodamine dye of claim 21, wherein $Y^1$ is selected from the group consisting of Y-1b, Y-2b, Y-3b, Y-4-b, Y-1c, Y-2c, Y-3c and Y-4-c.

23. The rhodamine dye of claim 21, wherein $Y^1$ is selected from the group consisting of Y-20b, Y-20c, Y-21b, Y-21c, Y-22b, Y-22c, Y-23b, Y-23c, Y-24b, Y-24c, Y-25b, Y-25c, Y-31b, Y-31c, Y-34b, Y-34c, Y-35b, Y-35c, Y-36b, Y-36c, Y-37b, Y-39b, Y-39c, Y-41c, Y-42b, Y-43b, Y-43c, Y-46b and Y-46c.

24. An energy-transfer dye pair comprising a donor dye linked to an acceptor dye, wherein the donor dye or the acceptor dye is a compound according to claim 1 and either or both of said donor and acceptor dyes include an optional linking moiety.

25. The dye pair of claim 24 having the structure:

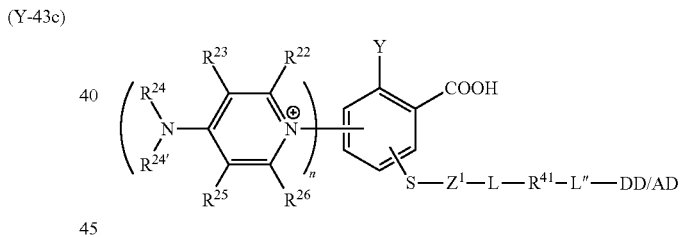

or a salt thereof, wherein:
R$^{41}$ is a covalent linkage formed upon reaction between a nucleophile and an electrophile;
L" is selected from the group consisting of a bond and a linker;
n is an integer selected from the group consisting of 1, 2, and 3; and
DD/AD is a donor dye or an acceptor dye which includes a linking moiety.

26. The dye pair of claim 25, wherein Y is selected from the group consisting of Y-1, Y-2, Y-3, Y-4, Y-20a, Y-21a, Y-22a, Y-23a, Y-24a, Y-25a, Y-31a, Y-34a, Y-35a, Y-36a, Y-39a, Y-41a, Y-42a, Y-43a, Y-44a, Y-45a and Y-46a.

27. The dye pair of claim 25, wherein L is a bond.

28. The dye pair of claim 25, wherein R$^{41}$ has the formula —C(O)NR$^{45}$—, wherein R$^{45}$ is selected from the group consisting of hydrogen and a (C$_1$-C$_6$) alkyl.

29. The dye pair of claim 25, wherein Z$^1$ is selected from the group consisting of a (C$_1$-C$_{12}$) alkyleno, a (C$_1$-C$_{12}$) alkano, a (C$_5$-C$_{10}$) aryldiyl or heteroaryldiyl, phenyldiyl, phena-1,4-diyl, naphthadiyl, naphtha-2,6-diyl, pyridindiyl and purindiyl.

30. The dye pair of claim 25, wherein L" is —$R^{43}$—$Z^3$—C(O)—$R^{44}$—$R^{45}$—, wherein $R^{43}$ is a ($C_1$-$C_6$) alkyldiyl, and is bonded to $R^{42}$, wherein $R^{42}$ is selected from the group consisting of O, S and NH; $Z^3$ is selected from the group consisting of a 5-6 membered cyclic alkenyldiyl or heteroalkenyldiyl and a ($C_5$-$C_{14}$) aryldiyl or heteroaryldiyl; $R^{44}$ is selected from the group consisting of O, S and NH; and $R^{45}$ is a ($C_1$-$C_6$) alkyldiyl.

31. The dye pair of claim 25, wherein DD/AD is a fluorescein dye in which the linking moiety is a reactive functional group, and wherein L" is attached to the fluorescein dye at the xanthene C4 carbon.

32. The dye pair of claim 25 having the structure:

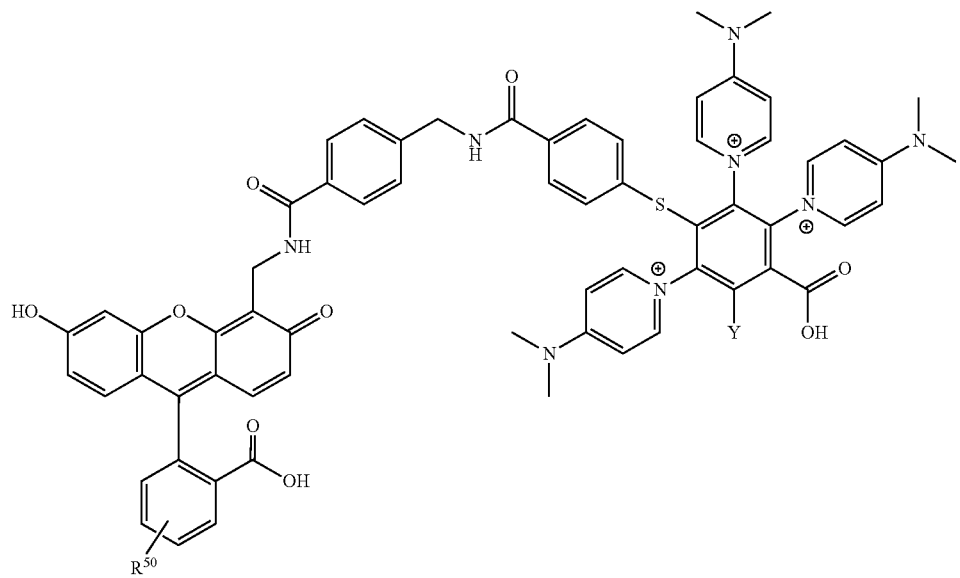

wherein $R^{50}$ is carboxyl, a salt, an ester or an activated ester thereof.

33. The dye pair of claim 32, wherein Y is selected from the group consisting of Y-1, Y-2, Y-3, Y-4, Y-20a, Y-21a, Y-22a, Y-23a, Y-24a, Y-25a, Y-31a, Y-34a, Y-35a, Y-36a, Y-39a, Y-41a, Y-42a, Y-43a, Y-44a, Y-45a and Y-46a.

34. The dye pair of claim 24 having the structure:

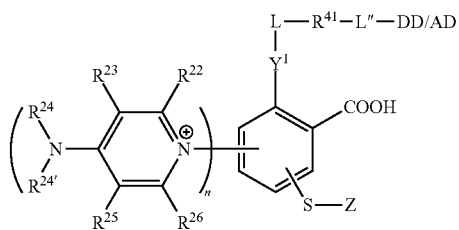

wherein:

$R^{41}$ is a covalent linkage formed upon reaction between a nucleophile and an electrophile;

L" is selected from the group consisting of a bond and a linker;

n is an integer selected from the group consisting of 1, 2, and 3; and

DD/AD is a donor dye or an acceptor dye which includes a linking moiety.

35. The dye pair of claim 34, wherein $Y^1$ is selected from the group consisting of Y-1b, Y-2b, Y-3b, Y-4-b, Y-1c, Y-2c, Y-3c, Y-4-c, Y-20b, Y-20c, Y-21b, Y-21c, Y-22b, Y-22c, Y-23b, Y-23c, Y-24b, Y-24c, Y-25b, Y-25c, Y-31b, Y-31c, Y-34b, Y-34c, Y-35b, Y-35c, Y-36b, Y-36c, Y-37b, Y-39b, Y-39c, Y-41c, Y-42b, Y-43b, Y-43c, Y-46b and Y-46c.

36. The dye pair of claim 34, wherein L is selected from the group consisting of a ($C_1$-$C_6$) alkyldiyl and a ($C_1$-$C_3$) alkano.

37. The dye pair of claim 34, wherein $R^{41}$ is an amide of the formula —C(O)$NR^{45}$—, wherein $R^{45}$ is selected from the group consisting of hydrogen and a ($C_1$-$C_6$) alkyl.

38. The dye pair of claim 34, wherein Z is selected from the group consisting of a ($C_1$-$C_{12}$) alkyl, a ($C_1$-$C_{12}$) alkanyl, a ($C_5$-$C_{10}$) aryl or heteroaryl, phenyl, naphthyl, naphth-1yl, naphth-2-yl, pyridyl and purinyl.

39. The dye pair of claim 34, wherein L" is —$R^{43}$—$Z^3$—C(O)—$R^{44}$—$R^{45}$—, wherein $R^{43}$ is a ($C_1$-$C_6$) alkyldiyl and is bonded to $R^{42}$, wherein $R^{42}$ is selected from the group consisting of O, S and NH; $Z^3$ is selected from the group consisting of a 5-6 membered cyclic alkenyldiyl or heteroalkenyldiyl and a ($C_5$-$C_{14}$) aryldiyl or heteroaryldiyl; $R^{44}$ is selected from the group consisting of O, S and NH; and $R^{45}$ is a ($C_1$-$C_6$) alkyldiyl.

40. The dye pair of claim 34, wherein DD/AD is a fluorescein dye in which the linking moiety is a reactive group $R_x$ and wherein L" is attached to the fluorescein dye at the xanthene C5 carbon.

41. The dye pair of claim 34 having the structure:

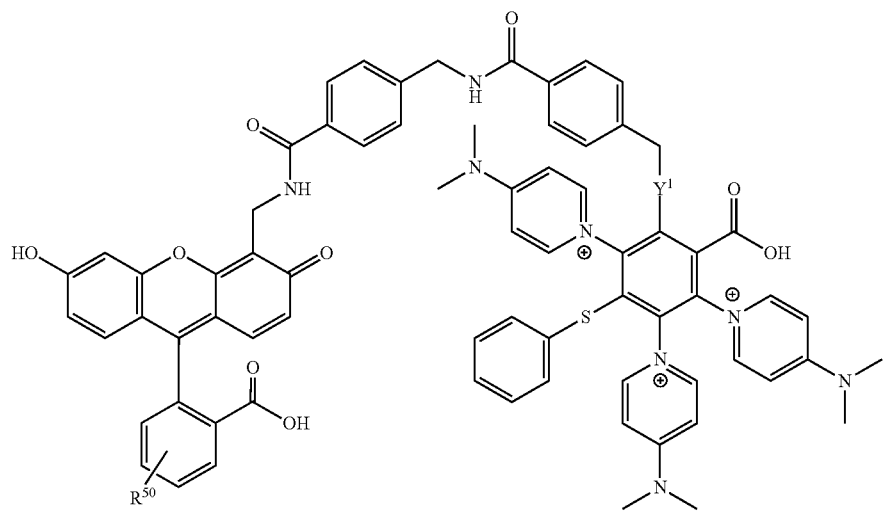

wherein:
 $Y^1$ is selected from the group consisting of Y-20b, Y-20c, Y-21b, Y-21c, Y-22b, Y-22c, Y-23b, Y-23c, Y-24b, Y-24c, Y-25b, Y-25c, Y-31b, Y-31c, Y-34b, Y-34c, Y-35b, Y-35c, Y-36b, Y-36c, Y-37b, Y-39b, Y-39c, Y-41c, Y-42b, Y-43b, Y-43c, Y-46b and Y-46c and
 $R^{50}$ is carboxyl, a salt, an ester or an activated ester thereof.

42. The dye pair of claim 35, wherein $Y^1$ is selected from the group consisting of Y-1b, Y-2b, Y-3b, Y-4-b, Y-1c, Y-2c, Y-3c, Y-4-c, Y-20b, Y-20c, Y-21b, Y-21c, Y-22b, Y-22c, Y-23b, Y-23c, Y-24b, Y-24c, Y-25b, Y-25c, Y-31b, Y-31c, Y-34b, Y-34c, Y-35b, Y-35c, Y-36b, Y-36c, Y-37b, Y-39b, Y-39c, Y-41c, Y-42b, Y-43b, Y-43c, Y-46b and Y-46c.

43. A polynucleotide labeled with a rhodamine dye according to claim 2 or an energy-transfer dye pair according to claim 28.

44. A method of generating a labeled primer extension product, comprising the step of enzymatically extending a primer-target hybrid in the presence of a mixture of enzymatically-extendable nucleotides capable of supporting continuous primer extension and a terminator, wherein said primer or said terminator is labeled with a rhodamine dye according to claim 2 or an energy-transfer dye pair according to claim 28.

45. The method of claim 44, wherein the terminator has the structure:

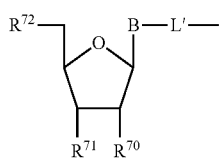

wherein each of $R^{70}$ and $R^{71}$, when taken alone, is independently selected from the group consisting of hydrogen, a halide and any moiety which blocks polymerase-mediated template-directed polymerization.

46. The method of claim 44, wherein the terminator is a mixture of four different terminators, one which terminates at a template A, one which terminates at a template G, one which terminates at a template C and one which terminates at a template T or U.

47. The method of claim 44, wherein each of the four different terminators is labeled with a different, spectrally-resolvable fluorophore.

* * * * *

UNITED STATES PATENT AND TRADEMARK OFFICE
CERTIFICATE OF CORRECTION

| | | |
|---|---|---|
| PATENT NO. | : 8,030,096 B2 | Page 1 of 1 |
| APPLICATION NO. | : 12/855649 | |
| DATED | : October 4, 2011 | |
| INVENTOR(S) | : Linda G. Lee et al. | |

It is certified that error appears in the above-identified patent and that said Letters Patent is hereby corrected as shown below:

Claims 43 and 44 should read as follows:

Column 91, Lines 65-67
Claim 43. A polynucleotide labeled with a rhodamine dye according to claim 1 or an energy-transfer dye pair according to claim 24.

Column 92, Lines 1-5
Claim 44. A method of generating a labeled primer extension product, comprising the step of enzymatically extending a primer-target hybrid in the presence of a mixture of enzymatically-extendale nucleotides capable of supporting continuous primer extension and a terminator, wherein said primer or said terminator is labeled with a rhodamine dye according to claim 1 or an energy-transfer dye pair according to claim 24.

Signed and Sealed this
Third Day of July, 2012

David J. Kappos
*Director of the United States Patent and Trademark Office*